(12) United States Patent
Berglund et al.

(10) Patent No.: US 10,865,229 B2
(45) Date of Patent: Dec. 15, 2020

(54) SYNTHETIC MBNL PROTEINS FOR TREATMENT OF REPEAT EXPANSION DISEASE

(71) Applicant: University of Florida Research Foundation, Incorporated, Gainesville, FL (US)

(72) Inventors: John A. Berglund, Gainesville, FL (US); Melissa Hale, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/308,098

(22) PCT Filed: Jun. 8, 2017

(86) PCT No.: PCT/US2017/036646
§ 371 (c)(1),
(2) Date: Dec. 7, 2018

(87) PCT Pub. No.: WO2017/214459
PCT Pub. Date: Dec. 14, 2017

(65) Prior Publication Data
US 2019/0177380 A1    Jun. 13, 2019

Related U.S. Application Data

(60) Provisional application No. 62/473,447, filed on Mar. 19, 2017, provisional application No. 62/347,573, filed on Jun. 8, 2016.

(51) Int. Cl.
*C07K 14/47* (2006.01)
*A61K 38/17* (2006.01)
*A61P 21/00* (2006.01)
*C07K 16/44* (2006.01)
*A61K 38/00* (2006.01)

(52) U.S. Cl.
CPC ............ *C07K 14/471* (2013.01); *A61K 38/17* (2013.01); *A61P 21/00* (2018.01); *C07K 14/4702* (2013.01); *C07K 14/4705* (2013.01); *C07K 16/44* (2013.01); *A61K 38/00* (2013.01); *C07K 2317/56* (2013.01); *C07K 2319/09* (2013.01); *C07K 2319/10* (2013.01); *C07K 2319/40* (2013.01); *C07K 2319/60* (2013.01); *C07K 2319/81* (2013.01); *C07K 2319/85* (2013.01)

(58) Field of Classification Search
CPC .............. C07K 14/471; C07K 14/4702; C07K 14/4705; C07K 16/44; C07K 2317/56; C07K 2319/09; C07K 2319/10; C07K 2319/40; C07K 2319/60; C07K 2319/81; C07K 2319/85; A61K 38/17; A61K 38/00; A61P 21/00
See application file for complete search history.

(56) References Cited

U.S. PATENT DOCUMENTS

| | | | |
|---|---|---|---|
| 2014/0178377 | A1 | 6/2014 | Armstrong |
| 2014/0288080 | A1 | 9/2014 | Zimmermann et al. |
| 2015/0064181 | A1 | 3/2015 | Armstrong |

FOREIGN PATENT DOCUMENTS

| | | |
|---|---|---|
| CA | 2248233 A1 | 9/1997 |
| WO | WO 2014/087023 A1 | 6/2014 |

OTHER PUBLICATIONS

PCT/US2017/036646, Sep. 6, 2017, International Search Report and Written Report.
PCT/US2017/036646, Dec. 20, 2018, International Preliminary Report on Patentability.
International Search Report and Written Opinion for Application No. PCT/US2017/036646 dated Sep. 6, 2017.
International Preliminary Report on Patentability for Application No. PCT/US2017/036646 dated Dec. 20, 2018.
[No Author Listed] CPPsite 2.0: Database of Cell-Penetrating Peptides. Retrieved from the Internet <http://crdd.osdd.net/raghava/cppsite/> on Feb. 12, 2019. 2 pages.
Batra et al., Loss of MBNL leads to disruption of developmentally regulated alternative polyadenylation in RNA-mediated disease. Mol Cell. Oct. 23, 2014;56(2):311-322. doi: 10.1016/j.molcel.2014.08.027. Epub Sep. 25, 2014.
Blech-Hermoni et al., RNA binding proteins in the regulation of heart development. Int J Biochem Cell Biol. Nov. 2013;45(11):2467-78. doi: 10.1016/j.bioce1.2013.08.008. Epub Aug. 20, 2013. Erratum in: Int J Biochem Cell Biol. Oct. 2014;55:348. Author manuscript.
Brook et al., Molecular basis of myotonic dystrophy: expansion of a trinucleotide (CTG) repeat at the 3' end of a transcript encoding a protein kinase family member. Cell. Feb. 21, 1992;68(4):799-808. Erratum in Molecular basis of myotonic dystrophy: expansion of a trinucleotide (CTG) repeat at the 3' end of a transcript encoding a protein kinase family member. [Cell. 1992].
Cass et al., The four Zn fingers of MBNL1 provide a flexible platform for recognition of its RNA binding elements. BMC Mol Biol. May 6, 2011;12:20. doi: 10.1186/1471-2199-12-20.

(Continued)

*Primary Examiner* — Gregory S Emch
(74) *Attorney, Agent, or Firm* — Wolf, Greenfield & Sacks, P.C.

(57) ABSTRACT

Provided herein are compositions and methods related to treating repeat expansion diseases that feature the sequestration of Muscleblind-like (MBNL) proteins by the toxic repeat RNA transcripts within distinct nuclear foci that are expressed from the expanded repeat tracts. Certain compositions of synthetic MBLN proteins can be used to displace endogenous MBNL from the toxic RNAs or replace endogenous MBNL within the cell for normal function.

15 Claims, 41 Drawing Sheets
Specification includes a Sequence Listing.

(56) References Cited

OTHER PUBLICATIONS

Chamberlain et al., Mouse model of muscleblind-like 1 overexpression: skeletal muscle effects and therapeutic promise. Hum Mol Genet. Nov. 1, 2012;21(21):4645-54. doi: 10.1093/hmg/dds306. Epub Jul. 30, 2012.
Chau et al., Developmental insights into the pathology of and therapeutic strategies for DM1: Back to the basics. Dev Dyn. Mar. 2015;244(3):377-90. doi: 10.1002/dvdy.24240. Epub Jan. 13, 2015.
Chen et al., Engineering RNA-binding proteins for biology. FEBS J. Aug. 2013;280(16):3734-54. doi: 10.1111/febs.12375. Epub Jul. 5, 2013.
Cummings et al., Fourteen and counting: unraveling trinucleotide repeat diseases. Hum Mol Genet. Apr. 12, 2000;9(6):909-16.
Daughters et al., RNA gain-of-function in spinocerebellar ataxia type 8. PLoS Genet. Aug. 2009;5(8):e1000600. doi: 10.1371/journal.pgen.1000600. Epub Aug. 14, 2009.
Dixon et al., Loss of muscleblind-like 1 results in cardiac pathology and persistence of embryonic splice isoforms. Sci Rep. Mar. 12, 2015;5:9042. doi: 10.1038/srep09042.
Du et al., Aberrant alternative splicing and extracellular matrix gene expression in mouse models of myotonic dystrophy. Nat Struct Mol Biol. Feb. 2010;17(2):187-93. doi: 10.1038/nsmb.1720. Epub Jan. 24, 2010. Author manuscript.
Du et al., RNA toxicity and missplicing in the common eye disease fuchs endothelial corneal dystrophy. J Biol Chem. Mar. 6, 2015;290(10):5979-90. doi: 10.1074/jbc.M114.621607. Epub Jan. 15, 2015.
Edgar, Muscle: multiple sequence alignment with high accuracy and high throughput. Nucleic Acids Res. Mar. 19, 2004;32(5):1792-7. Print 2004.
Edge et al., Dissecting domains necessary for activation and repression of splicing by Muscleblind-like protein 1. BMC Mol Biol. Dec. 27, 2013;14:29. doi: 10.1186/1471-2199-14-29.
Fardaei et al., in vivo co-localisation of MBNL protein with DMPK expanded-repeat transcripts. Nucleic Acids Res. Jul. 1, 2001;29(13):2766-71.
Fardaei et al., Three proteins, MBNL, MBLL and MBXL, co-localize in vivo with nuclear foci of expanded-repeat transcripts in DM1 and DM2 cells. Hum Mol Genet. Apr. 1, 2002;11(7):805-14.
Fernandez-Costa et al., Alternative splicing regulation by Muscleblind proteins: from development to disease. Biol Rev Camb Philos Soc. Nov. 2011;86(4):947-58. doi: 10.1111/j.1469-185X.2011.00180.x. Epub Apr. 13, 2011.
Fu et al., Context-dependent control of alternative splicing by RNA-binding proteins. Nat Rev Genet. Oct. 2014;15(10):689-701. doi: 10.1038/nrg3778. Epub Aug. 12, 2014. Author manuscript.
Fu et al., MBNL1-RNA recognition: contributions of MBNL1 sequence and RNA conformation. Chembiochem. Jan. 2, 2012;13(1):112-9. doi: 10.1002/cbic.201100487. Epub Nov. 22, 2011. Author manuscript.
Gates et al., Autoregulated splicing of muscleblind-like 1 (MBNL1) Pre-mRNA. J Biol Chem. Sep. 30, 2011;286(39):34224-33. doi: 10.1074/jbc.M111.236547. Epub Aug. 9, 2011.
Gautam et al., CPPsite: a curated database of cell penetrating peptides. Database (Oxford). Mar. 7, 2012;2012:bas015. doi: 10.1093/database/bas015. Print 2012.
Goers et al., MBNL1 binds GC motifs embedded in pyrimidines to regulate alternative splicing. Nucleic Acids Res. Apr. 2010;38(7):2467-84. doi: 10.1093/nar/gkp1209. Epub Jan. 13, 2010.
Grammatikakis et al., Identification of MBNL1 and MBNL3 domains required for splicing activation and repression. Nucleic Acids Res. Apr. 2011;39(7):2769-80. doi: 10.1093/nar/gkq1155. Epub Nov. 24, 2010.
Hino et al., Molecular mechanisms responsible for aberrant splicing of SERCA1 in myotonic dystrophy type 1. Hum Mol Genet. Dec. 1, 2007;16(23):2834-43. Epub Aug. 29, 2007.
Ho et al., Muscleblind proteins regulate alternative splicing. EMBO J. Aug. 4, 2004;23(15):310312. Epub Jul. 15, 2004.
Irion, Drosophila muscleblind codes for proteins with one and two tandem zinc finger motifs. PLoS One. 2012;7(3):e34248. doi: 10.1371/journal.pone.0034248. Epub Mar. 29, 2012.
Jangi et al., Building robust transcriptomes with master splicing factors. Cell. Oct. 23, 2014;159(3):487-98. doi: 10.1016/j.cell.2014.09.054.
Kalsotra et al., A postnatal switch of CELF and MBNL proteins reprograms alternative splicing in the developing heart. Proc Natl Acad Sci U S A. Dec. 23, 2008;105(51):20333-8. doi: 10.1073/pnas.0809045105. Epub Dec. 15, 2008.
Kalsotra et al., Functional consequences of developmentally regulated alternative splicing. Nat Rev Genet. Sep. 16, 2011;12(10):715-29. doi: 10.1038/nrg3052. Author manuscript.
Kanadia et al., Reversal of RNA missplicing and myotonia after muscleblind overexpression in a mouse poly(CUG) model for myotonic dystrophy. Proc Natl Acad Sci U S A. Aug. 1, 2006;103(31):11748-53. Epub Jul. 24, 2006.
Klein et al., Gain of RNA function in pathological cases: Focus on myotonic dystrophy. Biochimie. Nov. 2011;93(11):2006-12. doi: 10.1016/j.biochi.2011.06.028. Epub Jul. 13, 2011.
Kosaki et al., Identification of intron and exon sequences involved in alternative splicing of insulin receptor pre-mRNA. J Biol Chem. Apr. 24, 1998;273(17):10331-7.
La Spada et al., Repeat expansion disease: progress and puzzles in disease pathogenesis. Nat Rev Genet. Apr. 2010;11(4):247-58. doi: 10.1038/nrg2748. Author manuscript.
Lambert et al., RNA Bind-n-Seq: quantitative assessment of the sequence and structural binding specificity of RNA binding proteins. Mol Cell. Jun. 5, 2014;54(5):887-900. doi: 10.1016/j.molcel.2014.04.016. Epub May 15, 2014.
Lee et al., Pathogenic mechanisms of myotonic dystrophy. Biochem Soc Trans. Dec. 2009;37(Pt 6):1281-6. doi: 10.1042/BST0371281. Author manuscript.
Lin et al., Failure of MBNL1-dependent post-natal splicing transitions in myotonic dystrophy. Hum Mol Genet. Jul. 1, 2006;15(13):2087-97. Epub May 22, 2006.
Liquori et al., Myotonic dystrophy type 2 caused by a CCTG expansion in intron 1 of ZNF9. Science. Aug. 3, 2001;293(5531):864-7.
Lunde et al., RNA-binding proteins: modular design for efficient function. Nat Rev Mol Cell Biol. Jun. 2007;8(6):479-90. Author manuscript.
Mackay et al., The prospects for designer single-stranded RNA-binding proteins. Nat Struct Mol Biol. Mar. 2011;18(3):256-61. doi: 10.1038/nsmb.2005. Epub Feb. 27, 2011.
Mankodi et al., Muscleblind localizes to nuclear foci of aberrant RNA in myotonic dystrophy types 1 and 2. Hum Mol Genet. Sep. 15, 2001;10(19):2165-70.
Masuda et al., CUGBP1 and MBNL1 preferentially bind to 3' UTRs and facilitate mRNA decay. Sci Rep. 2012;2:209. doi: 10.1038/srep00209. Epub Jan. 4, 2012.
Meola et al., Myotonic dystrophies: An update on clinical aspects, genetic, pathology, and molecular pathomechanisms. Biochim Biophys Acta. Apr. 2015;1852(4):594-606. doi: 10.1016/j.bbadis.2014.05.019. Epub May 29, 2014.
Mooers et al., The structural basis of myotonic dystrophy from the crystal structure of CUG repeats. Proc Natl Acad Sci U S A. Nov. 15, 2005;102(46):16626-31. Epub Nov. 3, 2005.
Murn et al., Control of a neuronal morphology program by an RNA-binding zinc finger protein, Unkempt. Genes Dev. Mar. 1, 2015;29(5):501-12. doi: 10.1101/gad.258483.115.
Murn et al., Recognition of distinct RNA motifs by the clustered CCCH zinc fingers of neuronal protein Unkempt. Nat Struct Mol Biol. Jan. 2016;23(1):16-23. doi: 10.1038/nsmb.3140. Epub Dec. 7, 2015. Author manuscript.
Oddo et al., Conservation of context-dependent splicing activity in distant Muscleblind homologs. Nucleic Acids Res. Sep. 30, 2016;44(17):8352-62. doi: 10.1093/nar/gkw735. Epub Aug. 23, 2016.
Osborne et al., Transcriptional and post-transcriptional impact of toxic RNA in myotonic dystrophy. Hum Mol Genet. Apr. 15, 2009;18(8):1471-81. doi: 10.1093/hmg/ddp058. Epub Feb. 17, 2009.

(56) References Cited

OTHER PUBLICATIONS

Pan et al., Deep surveying of alternative splicing complexity in the human transcriptome by high-throughput sequencing. Nat Genet. Dec. 2008;40(12):1413-5. doi: 10.1038/ng.259. Epub Nov. 2, 2008.
Pascual et al., The Muscleblind family of proteins: an emerging class of regulators of developmentally programmed alternative splicing. Differentiation. Mar. 2006;74(2-3):65-80.
Purcell et al., Combinatorial mutagenesis of MBNL1 zinc fingers elucidates distinct classes of regulatory events. Mol Cell Biol. Oct. 2012;32(20):4155-67. Epub Aug. 13, 2012.
Rau et al., Misregulation of miR-1 processing is associated with heart defects in myotonic dystrophy. Nat Struct Mol Biol. Jun. 19, 2011;18(7):840-5. doi: 10.1038/nsmb.2067.
Sen et al., Muscleblind-like 1 (Mbnl1) promotes insulin receptor exon 11 inclusion via binding to a downstream evolutionarily conserved intronic enhancer. J Biol Chem. Aug. 13, 2010;285(33):25426-37. doi: 10.1074/jbc.M109.095224. Epub Jun. 2, 2010.
Stewart et al., Cell-penetrating peptides as delivery vehicles for biology and medicine. Org Biomol Chem. Jul. 7, 2008;6(13):2242-55. doi: 10.1039/b719950c. Epub Apr. 15, 2008.
Teplova et al., Structural insights into RNA recognition by the alternative-splicing regulator muscleblind-like MBNL1. Nat Struct Mol Biol. Dec. 2008;15(12):1343-51. doi: 10.1038/nsmb.1519. Epub Nov. 30, 2008. Author manuscript.
Tran et al., Analysis of exonic regions involved in nuclear localization, splicing activity, and dimerization of Muscleblind-like-1 isoforms. J Biol Chem. May 6, 2011;286(18):16435-46. doi: 10.1074/jbc.M110.194928. Epub Mar. 18, 2011.
Vicento-Crespo et al., *Drosophila* muscleblind is involved in troponin T alternative splicing and apoptosis. PLoS One. Feb. 20, 2008;3(2):e1613. doi: 10.1371/journal.pone.0001613.
Wagner et al., Dose-Dependent Regulation of Alternative Splicing by MBNL Proteins Reveals Biomarkers for Myotonic Dystrophy. PLoS Genet. Sep. 28, 2016;12(9):e1006316. doi: 10.1371/journal.pgen.1006316. eCollection Sep. 2016.
Wang et al., Alternative isoform regulation in human tissue transcriptomes. Nature. Nov. 27, 2008;456(7221):470-6. doi: 10.1038/nature07509. Author manuscript.
Wang et al., Antagonistic regulation of mRNA expression and splicing by CELF and MBNL proteins. Genome Res. Jun. 2015;25(6):858-71. doi: 10.1101/gr.184390.114. Epub Apr. 16, 2015.
Wang et al., Transcriptome-wide regulation of pre-mRNA splicing and mRNA localization by muscleblind proteins. Cell. Aug. 17, 2012;150(4):710-24. doi: 10.1016/j.cell.2012.06.041.
Warf et al., MBNL binds similar RNA structures in the CUG repeats of myotonic dystrophy and its pre-mRNA substrate cardiac troponin T. RNA. Dec. 2007;13(12):2238-51. Epub Oct. 17, 2007.

FIG. 2C

>WT-MBNL1 (280 amino acids)
MEYPYDVPDYAGSAVSVTPHLTLEVKGEFQTGQTGTCRAPSKYRGRRPCPRAPSKYRGRRPCPRAPSKYGRRRPCPRAPSK YRGRRPC...
LANAMMPGAPLQPVPMFSVAPSLATNASAAFNPYLGPVSPSLVPPAEHLPTAPMLVTGNPGVYPAAAAAAAQKLMRTQRLEVCREYQRGNCNRGEMDCRFAHPADSTMDTNDH
TVTVCMDYKGRCSREKCKYFHPPAHLQAKIKAAQYQVNQAAA [PKKKRKV]

>MBNL1(1-2,1-2) (296 amino acids)
MEYPYDVPDYAMAVSVTPHLTLEVKGEFQTGQTGTCRAPSKYGRRPCPSKSGRGCKYLHPPAHLACTQLEKGRNWLRCKMWLAQDME
LANAMMPGAPLQPVPMFSVAPSLATNASAAFNPYLGPVSPSLVPPAEILPTAPMLVTGNPGVYPAAAAAAAQKLMRTYAWLTEKRCREFQRGTSCSPDTEQKFAHPEKSCQRE
...ACRYLKQCCSRNKYLHPPAHLQAKIKAAQYQVNQAAA [PKKKRKV]

>MBNL1(3-4,3-4) (262 amino acids)
MEYPYDVPDYAKAVSVTPHLTLEVKGEFQTGQTGTCRAPSKYGRRPCPRAPSKMRTDRLEVCREYQRGNCNRGENDCRFAHPADSTMDTNDHTVTVCMDYKGRCSREKC
VAPSLATNASAAFNPYLGPVSPSLVPPAEILPTAPMLVTGNPGVYPAAAAAAAQKLMRTDRLEVCREYQRGNCNRGENDCRFAHPADSTMDTNDWTVTVCMDYKGRCSREKCMFS
KYFHPPAHLQAKIKAAQYQVNQAAA [PKKKRKV]

Key:
HA Tag
Nuclear Localization Sequence
ZF1-2 domain (93 amino acids)
ZF3-4 domain (76 amino acids)

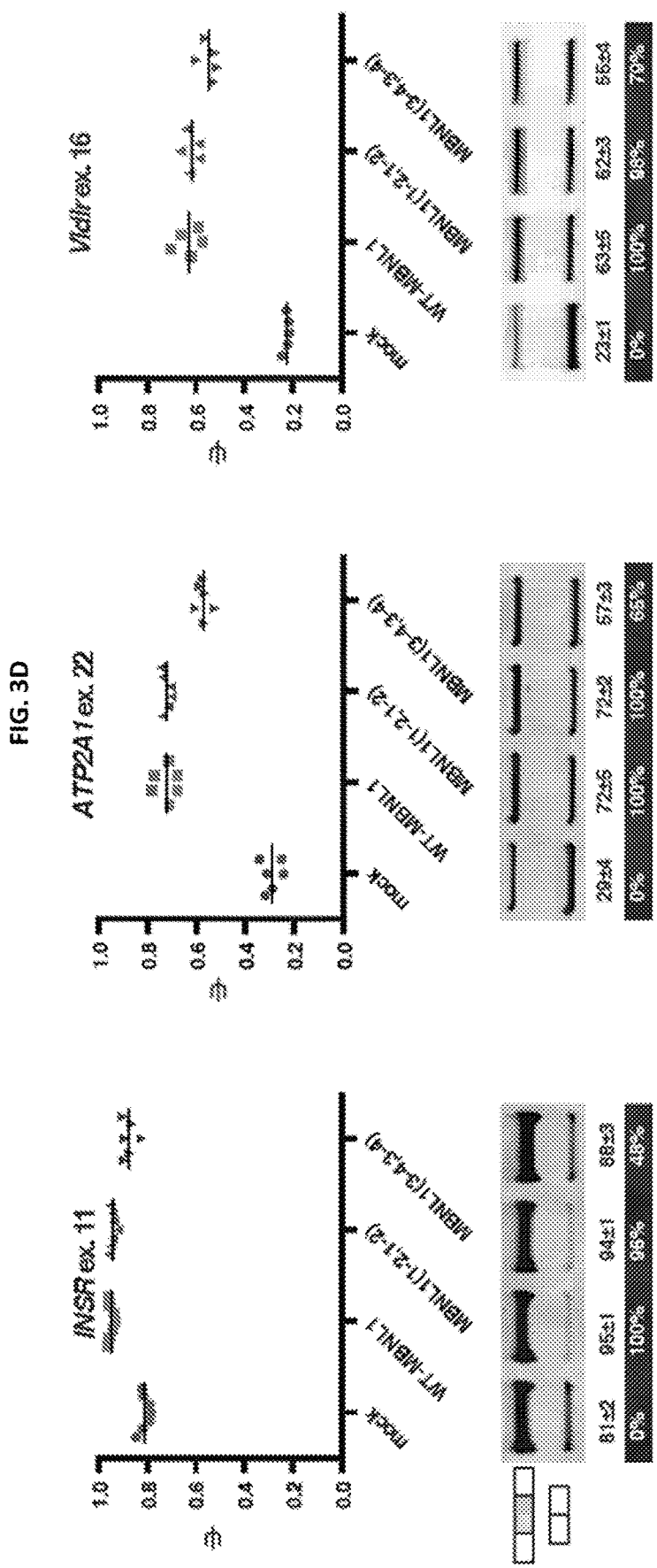

|  | Parameter | WT-MBNL1 | MBNL1(1-2,1-2) | MBNL1(3-4,3-4) |
|---|---|---|---|---|
| MBNL1 | Log(EC$_{50}$) | -0.71 ± 0.04 | -1.44 ± 0.07 | 0.06 ± 0.02 |
|  | Hill Slope | -1.84 ± 0.24 | -1.06 ± 0.21 | -1.35 ± 0.13 |
|  | R$^2$ | 0.97 | 0.96 | 0.96 |

|  | Parameter | WT-MBNL1 | MBNL1(1-2,1-2) | MBNL1(3-4,3-4) |
|---|---|---|---|---|
| ATP2A1 | Log(EC$_{50}$) | -0.48 ± 0.11 | -1.28 ± 0.10 | 0.10 ± 0.04 |
|  | Hill Slope | 1.34 ± 0.29 | 0.93 ± 0.23 | 1.25 ± 0.20 |
|  | R$^2$ | 0.96 | 0.95 | 0.90 |

|  | Parameter | WT-MBNL1 | MBNL1(1-2,1-2) | MBNL1(3-4,3-4) |
|---|---|---|---|---|
| TNNT2 | Log(EC$_{50}$) | -0.54 ± 0.16 | -1.62 ± 0.08 | 1.67 ± 1.18 |
|  | Hill Slope | -1.35 ± 0.48 | -1.14 ± 0.26 | -0.58 ± 0.54 |
|  | R$^2$ | 0.90 | 0.96 | 0.34 |

| RNA | Sequence |
|---|---|
| CUG$_4$ | 5'-GCUGCUGUUCGCUGCUG-3' |
| CAG$_4$ | 5'-GC[AGCA]GUUCGC[AGCA]G-3' |
| NV11 | 5'-UUUUGCUUUUUUUUUUUGCUUUU-3' |
| NV2CC | 5'-UUU[UCCU]UUUUUUUUU[UCCU]UUU-3' |

FIG. 15C

| MBNL1 | Log(EC$_{50}$) | Hill Slope | R$^2$ |
|---|---|---|---|
| WT-MBNL1 | -0.71 ± 0.04 | -1.84 ± 0.24 | 0.97 |
| WT-MBNL1 + CUG$_{960}$ | -0.56 ± 0.02 | -5.06 ± 1.40 | 0.97 |
| MBNL1(1-2,1-2) | -1.44 ± 0.07 | -1.06 ± 0.21 | 0.96 |
| MBNL1(1-2,1-2) + CUG$_{960}$ | -1.29 ± 0.05 | -1.41 ± 0.21 | 0.97 |
| MBNL1(3-4,3-4) | 0.06 ± 0.02 | -1.35 ± 0.13 | 0.96 |
| MBNL1(3-4,3-4) + CUG$_{960}$ | -0.05 ± 0.06 | -1.08 ± 0.20 | 0.86 |

| ATP2A1 | Log(EC$_{50}$) | Hill Slope | R$^2$ |
|---|---|---|---|
| WT-MBNL1 | -0.48 ± 0.11 | 1.34 ± 0.29 | 0.96 |
| WT-MBNL1 + CUG$_{960}$ | -0.49 ± 0.03 | 3.48 ± 0.92 | 0.94 |
| MBNL1(1-2,1-2) | -1.28 ± 0.10 | 0.93 ± 0.23 | 0.95 |
| MBNL1(1-2,1-2) + CUG$_{960}$ | -0.92 ± 0.06 | 1.33 ± 0.20 | 0.98 |
| MBNL1(3-4,3-4) | 0.10 ± 0.04 | 1.25 ± 0.20 | 0.90 |
| MBNL1(3-4,3-4) + CUG$_{960}$ | -0.03 ± 0.05 | 0.95 ± 0.13 | 0.92 |

| Protein | CUG / CCUG Repeats | Single Stranded / Endogenous |
|---|---|---|
| WT-MBNL1 | 100 – 250 nM | 5 – 10 nM |
| MBNL1(1-2,1-2) | 554 nM | 12 nM |
| MBNL1(3-4,3-4) | 182 nM | 104 nM |

SYNTHETIC MBNL PROTEINS FOR TREATMENT OF REPEAT EXPANSION DISEASE

RELATED APPLICATIONS

This application is a national stage filing under 35 U.S.C. § 371 of international application number PCT/US2017/036646, filed Jun. 8, 2017, which claims the benefit under 35 U.S.C. § 119(e) of U.S. Provisional Patent Application No. 62/347,573, filed on Jun. 8, 2016, and U.S. Provisional Patent Application No. 62/473,447, filed on Mar. 19, 2017, entitled "SYNTHETIC MBNL PROTEINS FOR TREATMENT OF REPEAT EXPANSION DISEASE," the entire contents of each of which are incorporated by reference herein.

The invention was made with government support under GM121862 awarded by The National Institutes of Health. The government has certain rights in the invention.

BACKGROUND

Repeat expansion diseases are a set of genetic disorders caused by mutations where polynucleotide repeats in certain genes exceed the normal threshold. Therapeutics for treating repeat expansion diseases, such as myotonic muscular dystrophy types 1 and 2 (DM1 and DM2), Fuchs endothelial corneal dystrophy (FECD) and spinocerebellar ataxia diseases, are needed.

SUMMARY

One of the key features of repeat expansion diseases is the sequestration of Muscleblind-like (MBNL) proteins by the repeat RNA transcripts within distinct nuclear foci that are expressed from the expanded repeat tracts. This sequestration results in depletion of MBNL proteins, and fewer MBNL1 to perform their normal function. MBNL proteins are alternative splicing factors critical for regulating exon use changes during development and across a variety of different tissue types. Depletion of MBNL proteins (e.g., MBNL1, 2, or 3) from the nucleoplasm via sequestration by these toxic RNAs leads to mis-splicing events responsible for many of the patients' symptoms.

Provided herein are compositions of synthetic MBNL proteins for the treatment of repeat expansion diseases that involve sequestration of MBNL proteins by toxic RNA. In some embodiments, the provided compositions of synthetic MBNL proteins can be used to displace endogenous MBNL from the toxic RNAs or replace endogenous MBNL within the cell. Synthetic MBNL proteins, for example, ones that provide the same or better binding to toxic RNA at lower concentrations compared to wild-type (WT) MBNL proteins, and/or any splicing activity can serve as a powerful decoy for toxic RNAs and therapeutic for repeat expansion diseases.

Accordingly, in some aspects, this application provides a composition comprising a synthetic MBNL protein comprising a first zinc finger (ZF) domain comprising a first ZF motif and a second ZF motif. In some embodiments, a synthetic MBNL protein comprises a first zinc finger (ZF) domain comprising a first ZF motif and a second ZF motif and a nuclear localization signal (NLS). In some embodiments, a synthetic MBNL protein comprising a first zinc finger (ZF) domain comprising a first ZF motif and a second ZF motif is linked to an NLS or other signal that results in nuclear localization of the protein by a linker.

In some embodiments, a synthetic MBNL1 protein is provided wherein the synthetic MBNL1 protein comprises: a first zinc finger (ZF) domain comprising a first ZF motif and a second ZF motif, a second ZF domain comprising a third ZF motif and a fourth ZF motif, and a nuclear localization signal (NLS). In some embodiments, the first ZF domain is linked to the second ZF domain by a linker, and the first ZF domain is positioned towards the N-terminal of the synthetic MBNL1 protein relative to the second ZF domain.

In some embodiments, a synthetic MBNL1 protein as provided herein comprises a first zinc finger (ZF) domain comprising a first ZF motif and a second ZF motif, and an RNA binding domain (RBD). In some embodiments, an RBD replaces a second ZF domain comprising a third ZF motif and a fourth ZF motif. In some embodiments, an RBD replaces a second ZF domain comprising a third ZF motif and a fourth ZF motif, and an NLS. In some embodiments, RBDs are non-specific. Some examples of RBDs are RGG boxes (arginine-glycine rich domains), double-stranded RNA binding domains (dsRBDs), RBFOX, RS and HIV nucleocapsid (NC) domains.

In some embodiments, a synthetic MBNL1 protein is truncated at the C-terminus (e.g., comprises a wild-type MBNL1 C-terminal sequence that is truncated at its C-terminus). In some embodiments, the synthetic MBNL1 protein is truncated at the C-terminus by 1-122 amino acids (e.g., by 1-10, 10-25, 25-50, 50-75, 75-100, or 100-122 amino acids).

In some embodiments, the amino acid sequence of the first ZF domain is SEQ ID NO: 1, and the amino acid sequence of the second ZF domain is SEQ ID NO: 2. In some embodiments, the amino acid sequence of the first ZF domain is SEQ ID NO: 1, and the amino acid sequence of the second ZF domain is SEQ ID NO: 1. In some embodiments, the amino acid sequence of the first ZF domain is SEQ ID NO: 2, and the amino acid sequence of the second ZF domain is SEQ ID NO: 2. In some embodiments, the amino acid sequence of the first ZF domain is SEQ ID NO: 2, and the amino acid sequence of the second ZF domain is SEQ ID NO: 79. In some embodiments, the amino acid sequence of the first ZF domain is SEQ ID NO: 79, and the amino acid sequence of the second ZF domain is SEQ ID NO: 2. In some embodiments, the amino acid sequence of the first ZF domain is SEQ ID NO: 79, and the amino acid sequence of the second ZF domain is SEQ ID NO: 79. In some embodiments, the amino acid sequence of the first ZF domain is SEQ ID NO: 1, and the amino acid sequence of the second ZF domain is SEQ ID NO: 79. In some embodiments, the amino acid sequence of the first ZF domain is SEQ ID NO: 79, and the amino acid sequence of the second ZF domain is SEQ ID NO: 1.

Contemplated herein is also a synthetic MBNL protein comprising a first zinc finger (ZF) domain comprising a first ZF motif and a second ZF motif, and a cell penetrating peptide (CPP), or an RNA binding domain (RBD). In some embodiments, the first ZF domain is linked to the CPP or RBD by a linker. In some embodiments, a synthetic MBNL1 protein with only one ZF domain further comprises a NLS. In some embodiments, the first ZF domain of a synthetic MBNL1 protein with only one ZF domain is positioned towards the N-terminal of a CPP or RBD.

In some embodiments, a synthetic MBNL protein comprises both a CPP and RBD.

In some embodiments of a synthetic MBNL1 protein with only one ZF domain, the amino acid sequence of the first ZF domain is SEQ ID NO: 1 or SEQ ID NO: 79, or has at least 80% sequence identity to SEQ ID NO: 1 or SEQ ID NO: 79.

In some embodiments, the linker is 5-100 amino acids long. In some embodiments, the linker is 15-80 amino acids long. In some embodiments, the linker is 100-200 amino acids long.

In some embodiments, the amino acid sequence of the linker comprises SEQ ID NO: 14. In some embodiments, the amino acid sequence of the linker is selected from the group consisting of: SEQ ID NO: 4, SEQ ID NO: 12, SEQ ID NO: 13, and SEQ ID NO: 14.

In some embodiments, the NLS is a monopartite NLS. In some embodiments, the NLS is a bipartite NLS. In some embodiments, the monopartite NLS comprises either at least four consecutive basic amino acids, or three basic amino acids. In some embodiments, the monopartite NLS comprising four consecutive basic amino acids is SV40 large T antigen NLS and comprises the amino acid sequence PKKKRKV (SEQ ID NO: 40). In some embodiments, the monopartite NLS comprising four consecutive basic amino acids is SV40 large T antigen NLS, and comprises the amino acid sequence of SEQ ID NO: 3. In some embodiments, the NLS is positioned at the C-terminal end of the synthetic MBNL1 protein.

In some embodiments, the synthetic MBNL1 protein comprises a tag that is useful for either purification of the protein and/or detection of the protein. In some embodiments, the tag is positioned at the N-terminal end of the synthetic MBNL1 protein, or in the N-terminus end of the protein after 1-10 amino acids. In some embodiments, the tag is positioned at or within the C-terminal end of the synthetic MBNL1 protein. In some embodiments, the tag is a peptide tag or a protein tag. In some embodiments, the peptide tag is selected from the group consisting of: His-tag, HA-tag, c-myc-tag, FLAG-tag, 3×FLAG-tag, strep-tag, E-tag and V5tag. In some embodiments, the protein tag is selected from the group consisting of: glutathione-S-transferase-tag, Fc-tag, thioredoxin-tag, biotin-tag and maltose binding protein-tag. A tag on any one of the synthetic MBNL1 proteins provided herein is not necessary for the function of binding toxic RNA.

In some embodiments, the synthetic MBNL1 protein is fused to a targeting moiety. In some embodiments, the targeting moiety is selected from the group consisting of: a cell penetrating peptide (CPP), a cell surface receptor binding ligand, a cell penetrating antibody, a mutant cell penetrating antibody, and a cell-penetrating antibody fragment. In some embodiments, the targeting moiety comprises an Fv antibody fragment (e.g., an Fv fragment of 3E10 murine anti-DNA autoantibody).

In some embodiments, the composition comprises a pharmaceutically acceptable carrier.

In some embodiments, the composition further comprises a liposome, a lipid, or a lipid complex.

In some aspects, the application provides a method of treating a subject having a repeat expansion disease, the method comprising administering to the subject one or more of the compositions provided herein.

In some embodiments, the repeat expansion disease is caused by repeats in non-coding sequences, or by exonic repeats that code for polyglutamine tracts. In some embodiments, the repeat expansion disease is selected from the group consisting of: myotonic muscular dystrophy type 1 (DM1), myotonic muscular dystrophy type 2 (DM2), Fuchs endothelial corneal dystrophy (FEDC), and spinocerebellar ataxia type 8 (SCA8).

In some embodiments, the composition is administered subcutaneously, intraocularly, intravitreally, subretinally, parenterally, intravenously (IV), intracerebro-ventricularly, intramuscularly, intrathecally (IT), intracisternally, orally, intraperitoneally, topically, by oral or nasal inhalation, or by direct injection to one or more cells, tissues, or organs by direct injection.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 2A-FIG. 2H show ZF domain organization architecture and expression levels of synthetic WT-MBNL1, MBNL1(1-2,1-2) and MBNL1(3-4,3-4) proteins. ZF1-2 is also referred to as 1-2, ZF3-4 is also referred to as 3-4, NLS: Nuclear localization signal. FIG. 2A shows a schematic of wild-type (WT) and synthetic MBNL1 proteins without any tags that shows the organization of zinc finger domains (ZF1-2 and ZF3-4) and location of an nuclear localization signal (NLS). FIG. 2B shows synthetic MBNL1 proteins with a HA-tag at the N-terminus of the proteins. FIG. 2C-FIG. 2E show wild-type and synthetic MBNL1 protein amino acid sequences. FIG. 2C shows sequences of both WT-MBNL1 (SEQ ID NO: 6) and the synthetic MBNL1(1-2,1-2) (SEQ ID NO: 7) and MBNL1(3-4,3-4) (SEQ ID NO: 8) proteins are shown. The ZF1-2 domain, ZF3-4 domain, HA tag, and nuclear localization signal (NLS) are highlighted. FIG. 2D shows sequence alignment of MBNL1 ZF1-2 and ZF3-4 derived using MUSCLE. Amino acid residues shown to contact RNA in the crystal structure of ZF3-4 in complex with RNA are highlighted. The sequences correspond to SEQ ID NOs: 1-2 from top to bottom. FIG. 2E shows sequence alignment of the ZF1-2 and ZF3-4 domains within the three human MBNL1 homologs using MUSCLE. The amino acid residues shown to contact RNA in the crystal structure of ZF3-4 in complex with RNA are highlighted. The protein amino acid sequences correspond to the following NCBI accession numbers: NP_066368, NP_659002, and NP_060858 for MBNL1, MBNL2, and MBNL3, respectively. The sequences correspond to SEQ ID NOs: 1, 32, 33, 2, 34, and 35 from top to bottom, respectively. These sequences are incorporated herein by reference. FIG. 2F-FIG. 2G show subcellular localization and mRNA expression levels are not impacted by ZF domain rearrangement. FIG. 2F shows subcellular protein localization of WT-MBNL1 and synthetic proteins determined using immunofluorescence against the HA tag in transfected HeLa cells. No significant differences in subcellular localization were detected between WT-MBNL1 and the synthetic MBNL1 proteins. FIG. 2G shows real-time qPCR analysis of synthetic MBNL1 RNA levels normalized to GAPDH in transfected HeLa cells. Determination of fold change in expression showed no differences in expression levels of synthetic proteins compared to WT-MBNL1. FIG. 2H shows quantification of protein and RNA levels in HEK-293 cells (n=3) via western blot against the HA tag. Values were normalized to WT-MBNL1 levels.

FIG. 3A shows splicing of exon 11 of insulin receptor (INSR) by WT-MBNL1, MBNL1(1-2,1-2) and MBNL1(3-4,3-4) from an assay using INSR minigene. The panel on the left shows data from a splicing assay in HeLa cells, and the right panel shows a drawing depicting MBNL1 splicing exon 11 of INSR. FIG. 3B shows splicing of exon 5 of human troponin T type 2 (hTNNT2) by WT-MBNL1, MBNL1(1-2,1-2) and MBNL1(3-4,3-4) from an assay using hTNNT2 minigene. The left panel shows data from a splicing assay in HeLa cells, and the right panel shows a drawing depicting MBNL1 splicing exon 5 of hTNNT2. FIG. 3C shows MBNL1 splicing activity for splicing six different minigenes (each represented by a dot on the graph), including INSR and hTNNT2. Data for MBNL1(1-2,1-2) and MBNL1(3-4,3-4) are normalized to WT-MBNL1. FIG. 3D shows that synthetic MBNL1 proteins regulate splicing of minigenes in HeLa cells with different activities. Jitter plot representations of cell-based splicing assays using INSR, ATP2A1, Vldlr, TNNT2, MBNL1, and Nfix minigenes, respectively. HeLa cells were transfected with empty vector (mock) or MBNL1 protein expression plasmids and a single minigene reporter. Percent spliced in (PSI, ψ) (e.g., percent exon inclusion) for each protein treatment was then quantified. Each point is from a single experiment and the line represents the average of all experiments for that condition (at least n=5 for each protein treatment). Average ψ (±standard deviation) and percent splicing activity (displayed in white) are listed below the representative splicing gels. FIG. 3E shows the protein expression levels of WT-MBNL1, MBNL1(1-2,1-2) and MBNL1(3-4,3-4) synthetic proteins in HeLa cells. The bottom graph shows quantification of western blot data of expressed MBNL1 protein. The quantification of synthetic protein levels in HeLa cells via western blot against the HA tag (n=4). Relative levels of each protein were normalized to GAPDH. WT-MBNL1 expression values were then set equal to 1 and MBNL1(1-2,1-2) and MBNL1(3-4,3-4) protein levels normalized. FIG. 3F shows average splicing activity of synthetic MBNL1 proteins across 6 minigene events. Jitter plot representation of average splicing activities for WT-MBNL1 and synthetic proteins in HEK-293 cells. Each point is the splicing activity of each protein for a single minigene event tested (see FIG. 3D and FIG. 3G) and the line represents the average of all splicing activities. WT-MBNL1 was considered to have 100% splicing activity for each event and the values for MBNL1(1-2,1-2) and MBNL1(3-4,3-4) were calculated accordingly. FIG. 3G shows that synthetic MBNL1 proteins regulate splicing of minigenes in HEK-293 cells with different activities. Jitter plot representations of splicing assays using INSR, ATP2A1, Vldlr, TNNT2, MBNL1, and Nfix minigenes, respectively. HEK-293 cells were transfected with empty vector (mock), WT-MBNL1, or synthetic MBNL1 protein-expression plasmids and a single minigene reporter. RNA was isolated from cells, RT-PCR performed, and the DNA products resolved on a native gel. Percent spliced in (PSI, ψ) (e.g., percent exon inclusion) for each protein treatment was then quantified. Each point is from a single experiment and the line represents the average of all experiments for that condition (n=5 for each protein treatment). ψ (±standard deviation) and percent splicing activity (displayed in white) are listed below representative splicing gels.

FIG. 8A shows representative splicing gels for three minigenes tested acquired using the Advanced Analytical Fragment Analyzer. Bands are representative of relative fluorescence units (RFU) for each cDNA product and were used to calculate ψ for each plasmid dose. Average ψ±standard deviation at each plasmid dose are listed below each gel (n=3-5 for each). FIG. 8B shows quantitative parameters ($\log(EC_{50})$ and Hill Slope, ±standard error) generated from the dose-response curves. FIG. 9A-FIG. 9C show plasmid dosing assays for MBNL1 (FIG. 9A), ATP2A1 (FIG. 9B), and TNNT2 (FIG. 9C) minigene events, respectively. Increasing amounts of plasmid expressing WT-MBNL1 or synthetic MBNL1 proteins were transfected into HeLa cells along with a minigene reporter (n=3-5 plasmid dose). ψ values were then quantified, plotted against log [MBNL1] levels, and fit to a four-parameter dose-response curve. Relative MBNL1 expression levels for each protein were determined via western blot (n=3) at each plasmid dose and normalized to GAPDH. Representative immunoblots and splicing gels can be found in FIG. 7 and FIG. 8A, respectively. FIG. 9D shows $\log(EC_{50})$ values and Hill slopes derived from the dose-response curves (table of exact values±standard error are listed in FIG. 8B). Due to ambiguous curve fitting of MBNL1(3-4,3-4), the bottom (MBNL1 and TNNT2) or top (ATP2A1) of the curve was constrained to match the average ψ value of WT-MBNL1 at the highest plasmid dose.

FIG. 10A shows sequence of four RNAs used in EMSAs with synthetic MBNL1 proteins. The sequences correspond to SEQ ID NOs: 36-39 from top to bottom, respectively. The occurrence of specific UGCU motifs (bold and underlined) and mutated non-specific motifs (bold and boxed) within the RNA substrates are noted. FIG. 10B shows representative EMSA gels to $CUG_4$/$CAG_4$ RNA substrates (n=3 for each RNA). FIG. 10C shows binding curves of WT-MBNL1 and synthetic MBNL1 proteins for $CUG_4$. Apparent dissociation constants (Kds) (±standard error) for each MBNL1 are listed. FIG. 10D shows representative EMSA gels for NV11/NV2CC RNA substrates (n=3 for each RNA). FIG. 10E shows binding curves for each MBNL1 protein comparing the differences in affinity between NV11 and the non-specific mutant NV2CC. Kd (±standard error) for each RNA listed below each plot.

FIG. 11A shows scatterplots comparing R values for all kmers (k=7) between WT-MBNL1, MBNL1(1-2,1-2) and MBNL1(3-4,3-4) at three different protein concentrations. FIG. 11B shows scatterplots comparing R values for all kmers between WT-MBNL1 and those identified with MBNL1 in a previous RBNS study at three protein concentrations. FIG. 11C shows area-proportional Venn diagram showing overlap in top 50 kmers for WT-MBNL1 and those identified using MBNL1 in a previous RBNS study. Values listed represent number of kmers within each sub-population.

FIG. 12A-FIG. 12C show RBNS R values for the top four kmers (k=7) as a function of MBNL1 protein concentration for WT-MBNL1 (FIG. 12A), MBNL1(1-2,1-2) (FIG. 12B), and MBNL1(3-4,3-4) (FIG. 12C), respectively. Top four k-mers for each protein are determined based on concentration of protein that shows the greatest R-values (250 nM, 500 nM, and 1000 nM for WT-MBNL1, MBNL1(1-2,1-2), and MBNL1(3-4,3-4), respectively). R-values at all other concentrations for the respective kmers were then determined to create the unimodal enrichment plots shown. FIG. 12D shows the percent nucleotide occurrence within the top 100 kmers for each MBNL1 protein. FIG. 12E shows area-proportional Venn diagram showing overlap in top 50 kmers for each MBNL1 protein. Values listed represent number of kmers within each sub-population.

FIG. 14A and FIG. 14B show plasmid dosing assays performed using the MBNL1 (FIG. 14A) and ATP2A1 (FIG. 14B) minigenes, respectively, in the presence of CUG repeat RNA. HeLa cells were transfected with the same increasing amounts of plasmid to create a gradient of protein expression as done in FIG. 9A-FIG. 9D. Cells were transfected with a minigene reporter and a CTG960 repeat expressing plasmid. ψ values at each plasmid dose were quantified (n=3-4 for each plasmid dose), plotted against log[MBNL1] levels, and fit to a four-parameter dose-response curve. Representative splicing gels can be found in FIG. 13A-FIG. 13B. FIG. 14C shows $\log(EC_{50})$ values and slopes derived from the dose-response curves (table of exact values±standard error are listed in FIG. 15C). Due to ambiguous curve fitting of MBNL1(3-4,3-4), the bottom (MBNL1) or top (ATP2A1) of the curve was constrained to match the average ψ value of WT-MBNL1 at the highest plasmid dose. These values are compared to those determined in the absence of toxic RNA expression (FIG. 9C and FIG. 8B). Comparison of the dose curves in the presence and absence of CUG960 RNA expression can be found in FIG. 15A and FIG. 15B for MBNL1 and ATP2A1, respectively.

FIG. 15A-FIG. 15C show expression of CUG repeat toxic RNA alters the MBNL1 dose-response curve. FIG. 15A and FIG. 15B show a comparison of dose curves with the MBNL1 (FIG. 15A) and ATP2A1 (FIG. 15B) minigene in presence and absence of DMPK-CTG960 transfection for all three MBNL1 proteins tested. FIG. 15C shows quantitative parameters ($\log(EC_{50})$ and Hill Slope, ±standard error) generated from the dose-response curves in the presence and absence of toxic repeat RNA expression. Overall quality of the fit, as represented by $R^2$ values is also listed.

FIG. 17A shows a schematic for ZF1-2-CPP fusion proteins containing both human and D. melanogaster (mbl) domains. FIG. 17B shows a schematic for synthetic MBNL1-Linker synthetic proteins. FIG. 17C shows synthetic proteins comprising ZF1-2 non-specific RBD domains.

FIG. 19A shows binding of an RNA binding domain with the minor groove of A-form double stranded RNA. FIG. 19B shows that a short $CUG_6$ repeat forms these A-form dsRNA structures in vitro (Mooers et al., Proc Natl Acad Sci USA. 2005; 102(46): 16626-31, incorporated herein by reference in its entirety).

FIG. 22A shows that Expression of MBNL1-HIV NC from plasmid in HeLa cells regulates splicing of TNNT2 ex. 5. FIG. 22B shows that Expression of MBNL1-HIV NC from plasmid in HeLa cells regulates splicing of MBNL ex. 5. Mock: plasmid not expressing protein. ZF1-2 linker: same as WT-MBNL1 except ZF3-4 has been truncated.

FIG. 24A shows Inclusion of CLASP1 exon 18 across a broad range of MBNL1 concentrations, with curve fit, slope and EC50. Percent spliced in (Y) of the regulated exon is plotted against log(MBNL1). The log(MBNL1) was estimated by Western across the dox concentrations using GAPDH for normalization. FIG. 24B shows dose response of 3 events known to be mis-spliced in DM1 mouse models. FIG. 24C shows comparison of RNAseq data from no dox and high dox in the MEF and HEK cell lines revealing a strong correlation (Rspearman coefficient of 0.73) in changes in splicing (ΔΨ) between these two cell lines.

DETAILED DESCRIPTION

Figure 1:
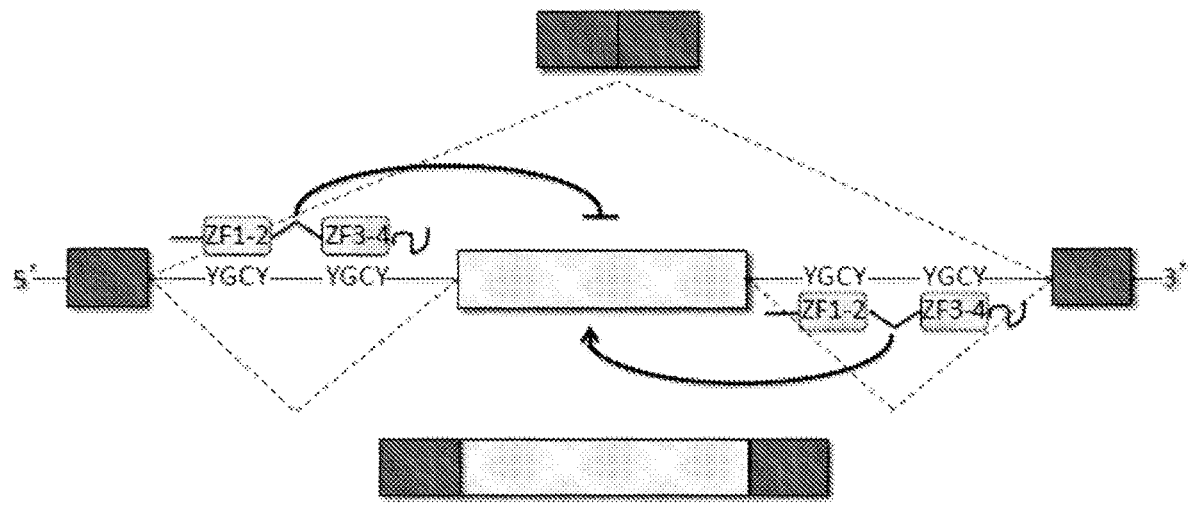
FIG. 1 depicts how the two distinct RNA binding domains of MBNL1, zinc finger (ZF) 1-2 (ZF1-2) and zinc finger 3-4 (ZF3-4), bind to YGCY motifs within pre-mRNA to regulate alternative splicing.

Alternative splicing is a complex and versatile process of post-transcriptional gene regulation whereby exons within a precursor RNA transcript are differentially joined and introns removed to produce a mature mRNA. Alternative splicing generates multiple mRNA isoforms from an individual gene most often resulting in the expression of a diverse set of protein products. Additionally, alternative splicing alters the fate of mRNAs through the inclusion of regions that impact RNA localization, translation, and turnover. More than 90% of human protein coding genes undergo alternative splicing, making regulation of this process critical for proper cellular function. Trans-acting protein factors, including RNA binding proteins (RBPs) can function as regulators of alternative splicing by interacting with specific RNA motifs, or splicing regulatory elements, to enhance or repress the inclusion of alternative exons. RBPs also act in a spatio-temporal and developmentally dependent manner to modulate the overall profile of mRNAs produced within specific cell types, developmental stages, or in response to varying environmental conditions.

Muscleblind-like (MBNL) proteins are a family of highly conserved RBPs that regulate RNA metabolism during tissue-specific development, most notably the activation or repression of alternative exon inclusion. MBNL proteins have been specifically implicated in regulating fetal to adult mRNA isoform transitions in heart and muscle tissue. In addition, MBNL proteins have also been linked to the regulation of other RNA metabolic processes including localization, turnover, gene expression, alternative polyadenylation, and micro-RNA processing.

MBNL proteins, particularly MBNL1, have been the focus of intense study for the past 15 years due to their prominent role in the pathogenesis of myotonic dystrophy (DM). DM is a multi-systemic neuromuscular disorder caused by expression of CTG or CCTG repeat expansions within the 3' untranslated region of DMPK (DM Type 1) or intron 1 of CNBP (DM Type 2), respectively. Once transcribed into RNA, these expanded CUG or CCUG repeats sequester MBNL proteins into discrete nuclear RNA-protein aggregates called foci. Sequestration of MBNL by these toxic, expanded RNAs leads to dysregulation of MBNL-mediated alternative splicing linked as causative of some disease symptoms. Although most commonly associated with DM, loss of MBNL1 function has also been associated with other disorders, specifically spinocerebellar ataxia type 8 (SCA8) and Fuchs Endothelial Corneal Dystrophy (FECD).

In order to regulate specific splicing events, MBNL1 acts as an enhancer or repressor in a transcript dependent manner. In general, if MBNL1 binds upstream of a regulated exon it suppresses inclusion and if it binds downstream it enhances inclusion. RNA binding by MBNL1 is mediated via four highly conserved CCCH(SEQ ID NO: 80)-type (CX7CX4-6CX3H) zinc finger (ZF) motifs that fold into two tandem RNA binding domains commonly referred to as ZF1-2 and ZF3-4. These two domains are located within the N-terminal region of the protein and are separated by a flexible linker that is predicted to mediate MBNL1 binding to a wide variety of RNAs. Studies have shown that MBNL proteins bind YGCY (Y=C or U) motifs within their RNA targets. Crosslinking immunoprecipitation (CLIP)-seq and RNA Bind-n-seq (RBNS) experiments have identified several additional related motifs. The expanded CUG/CCUG repeat RNA in DM patients contain many YGCY motifs, providing a sink for MBNL and the subsequent dysregulation of RNA processing events mediated by MBNL proteins.

Repeat expansion diseases are caused by genetic mutations wherein a subject has polynucleotide repeats in certain genes that exceed the normal threshold number of repeats. A consequence of polynucleotide repeat expansions is sequestration and depletion of MBNL proteins that can perform their normal function. All three MBNL proteins regulate splicing. MBNL1 and its paralogs act as a splicing enhancer or repressor in a transcript dependent manner where, in general, if MBNL1 binds upstream of an exon it suppresses inclusion and if it binds downstream it enhances inclusion (FIG. 1). MBNL1 contains four zinc finger (ZF) RNA binding motifs commonly referred to as ZF1, ZF2, ZF3, and ZF4 (FIG. 1). The first two ZFs fold into one domain (ZF1-2) located at the N-terminus and the second set of ZFs fold into another domain (ZF3-4) in the middle of the protein. ZF1-2 and ZF3-4 are also herein referred to as 1-2 and 3-4, respectively. These tandem sets of ZF pairs form two distinct RNA binding domains separated by a flexible amino acid linker. Each ZF pair binds YGCY motifs within its RNA targets. For example, the CUG/CCUG repeat RNA in myotonic muscular dystrophy (DM) patients is enriched with these YGCY motifs, providing a high-affinity platform for MBNL proteins binding and subsequent depletion from the nucleoplasm for normal function.

Figure 2A:
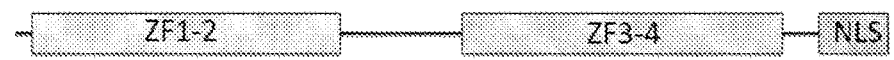
Figure 2A:
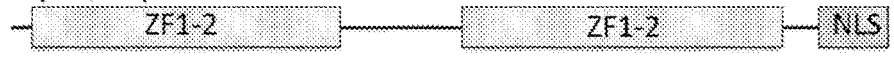
Figure 2A:
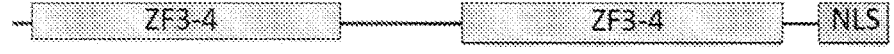
Figure 2B:
Figure 2B:
Figure 2B:
Figure 2D:
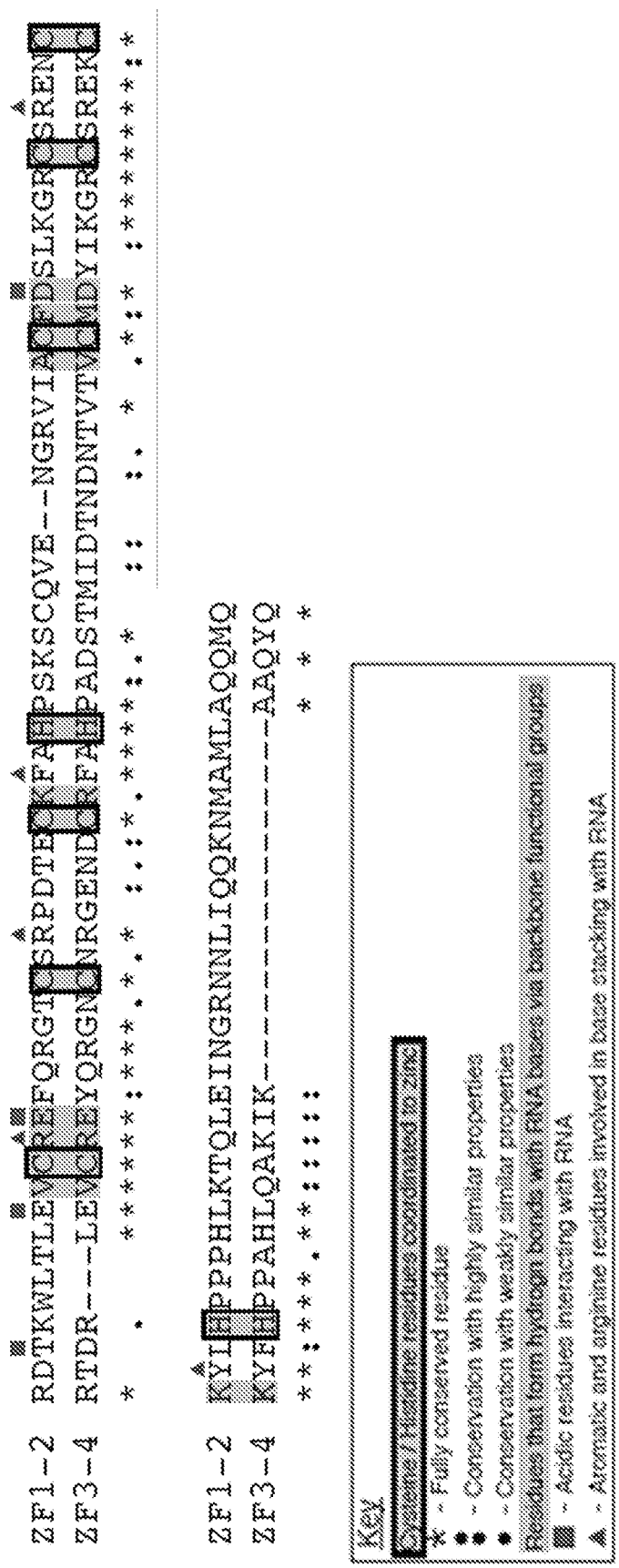

Sequence alignment and secondary structural overlay of the two ZF domains show that ZF1/ZF3 and ZF2/ZF4 have high sequence similarity and nearly identical structures. The major differences between the domains is an extended α-helix at the C-terminus of ZF2 and an interdomain linker that is two amino acids shorter in the ZF1-2 pair (FIG. 2D). Due to the high degree of similarity between the two domains as well as their physical separation via the linker, it has been predicted that the ZF domains have the same or similar RNA binding activities and may be functionally redundant. The hypothesis of functional redundancy is further supported by studies with the D. melanogaster and C. elegans orthologs of the MBNL1 gene, muscleblind (mbl). Mbl from these organisms contains only a single ZF domain orthologous to the human ZF1-2 yet is able to regulate splicing of many MBNL1 target transcripts in mammalian cell culture. Any one of the embodiments of a synthetic MBNL protein may contain a domain from a non-human species (e.g., D. melanogaster and C. elegans) that is orthologous or homologous to any of the ZF domains described herein (e.g., ZF1-2 or ZF3-4). For example, in some embodiments, a synthetic MBNL protein comprises one or more mbl domains from D. melanogaster.

Despite the similarity between these domains, combinatorial mutagenic analysis of the four ZFs found that ZF1-2 and ZF3-4 are not functionally equivalent. Using this approach it was discovered that a MBNL1 protein with a single functional ZF1-2 bound with higher affinity to all tested RNA substrates compared to a MBNL1 with only a functional ZF3-4. Additionally, a MBNL1 with only an active ZF1-2 retained approximately 80% of WT-MBNL1 splicing activity while the MBNL1 mutant with only a active ZF3-4 retained 50% splicing regulation. Despite these observations it still remained unclear if the ZF pairs truly act as independent domains. Additionally, the function of the individual ZF domains and whether they cooperate in some manner through higher-order interactions to achieve alternative splicing regulation remains ambiguous.

Figure 17A:
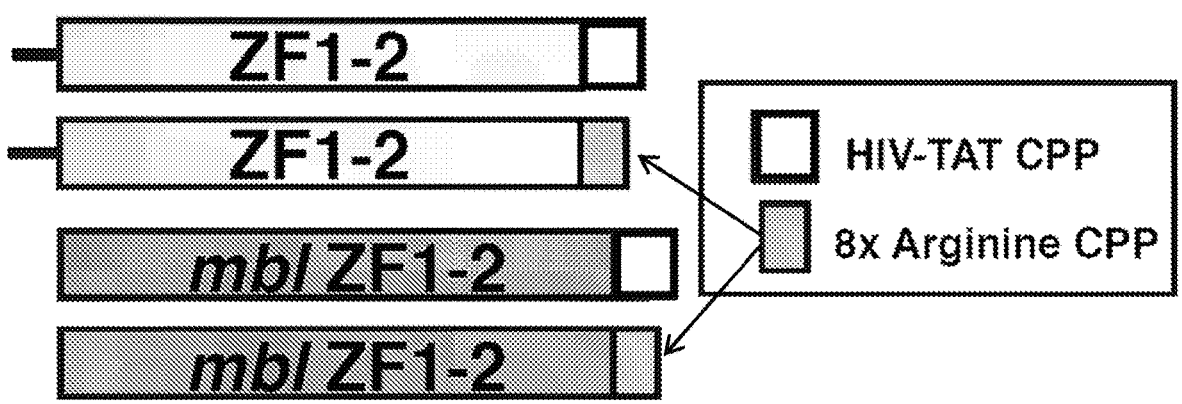
FIG. 17A-FIG. 17C show schematics for minimal MBNL1 proteins.
Figure 17B:
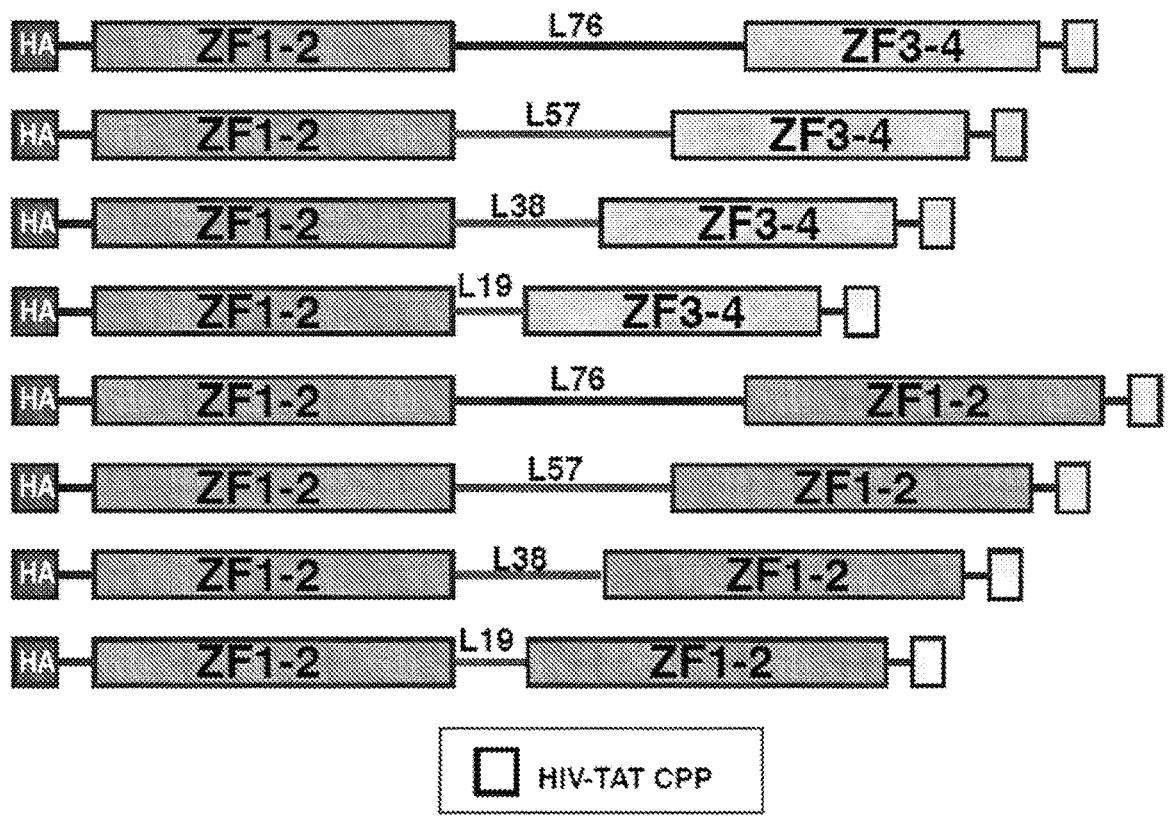
Figure 17C:
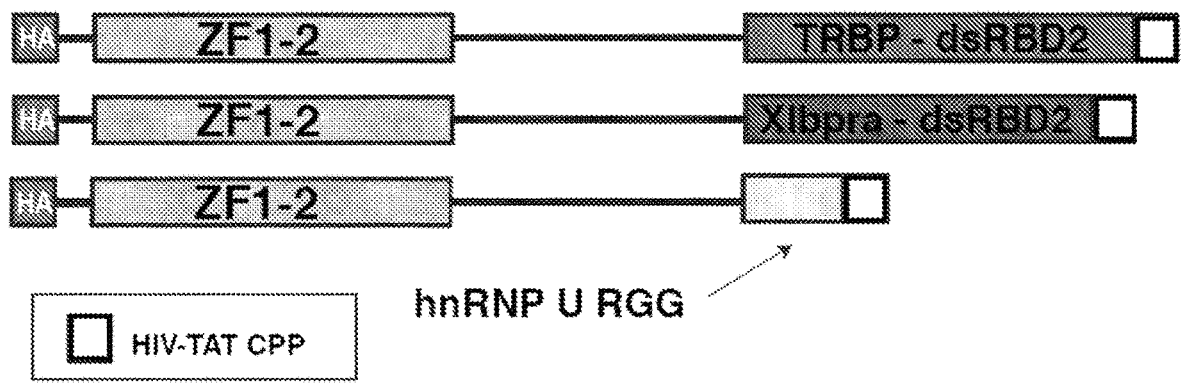

In order to address these questions, a synthetic biology approach was utilized to generate chimeric MBNL1 proteins with novel ZF domain organization. Specifically, it was contemplated that a synthetic MBNL1 protein with higher RNA binding affinity and subsequent splicing activity could be engineered by replacing ZF3-4 with a second ZF1-2 (FIG. 2A). Accordingly, synthetic MBNL1 constructs were engineered with duplicate ZF domains: (i) a MBNL1 in which the ZF3-4 domain is replaced with a ZF1-2 to create a MBNL1(1-2,1-2) and (ii) a MBNL1(3-4,3-4) in which the ZF1-2 domain is substituted with a ZF3-4. Other synthetic MBNL1 proteins as shown in FIG. 17A-17C were also contemplated and provided herein.

It was discovered that ZF1-2 and ZF3-4 domains act as independent units with distinct characteristics, most notably different RNA binding specificities. It was also shown that the ZF domains can be organized in novel ways to produce synthetic MBNL1 proteins with different activities as assayed by alternative splicing and RNA binding assays. The provided synthetic proteins are useful as therapeutics in DM and other microsatellite diseases.

Earlier studies reveal that ZF1-2 and ZF3-4 have different splicing as well as RNA binding properties (Purcell et al., Mol Cell Biol, 2012, 32:4155). Herein are provided compositions and methods for use in the treatment of repeat expansion diseases, the compositions comprising synthetic MBNL1 protein with alternative configurations of ZF domains and truncations that result in better properties for RNA binding, splicing activity and better solubility properties that enable more efficient and convenient protein preparation methods and dosing. It is expected that results provided for MBNL1 herein can be applied to MBNL2 and MBNL3. Accordingly, in some embodiments synthetic protein configurations described in the context of MBNL1 can be provided using one or more MBNL2, MBNL3, or combinations of one or more MBNL1, MBNL2, and/or MBNL3 motifs or domains or variants thereof.

In some aspects, a composition is provided that comprises a synthetic MBNL1 protein, wherein the synthetic MBNL1 protein comprises: a first zinc finger (ZF) domain comprising a first ZF motif and a second ZF motif, a second ZF domain comprising a third ZF motif and a fourth ZF motif, and nuclear localization signal (NLS). In some embodiments, the first ZF domain is linked to the second ZF domain by a linker, and the first ZF domain is positioned towards the N-terminal of the synthetic MBNL1 protein relative to the second ZF domain.

In some embodiments, the synthetic MBNL1 protein is truncated at the C-terminus. SEQ ID NO: 15 shows the amino acid sequence of full-length human MBNL1 protein. In some embodiments, a synthetic MBNL1 protein is truncated at the C-terminus by 1-122 amino acids (e.g., by about 1, 10, 50, 80, 100 or 122 amino acids), 1-129 amino acids (e.g., by about 1, 10, 50, 122, or 129 amino acids), 100-129 amino acids (e.g., by about 100, 110, 122 or 129 amino acids), 1-50 amino acids (e.g., by about 1, 10, 30 or 50 amino acids), or 50-100 amino acids (e.g., by about 50, 80 or 100 amino acids). In some embodiments, truncation of the C-terminus of MBNL1 protein results in better solubility of the protein.

An Example of an Amino Acid Sequence of Full-Length MBNL1 Protein:

```
                                        (SEQ ID NO: 15)
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVPMFSVAPSLATNASAAAFNPYLGPVSPSLVPAEIL

PTAPMLVTGNPGVPVPAAAAAAAQKLMRTDRLEVCREYQRGNCNRGENDC

RFAHPADSTMIDTNDNTVTVCMDYIKGRCSREKCKYFHPPAHLQAKIKAA

QYQVNQAAAAQAAATAAAMTQSAVKSLKRPLEATFDLGIPQAVLPPLPKR
```

-continued
```
PALEKTNGATAVFNTGIFQYQQALANMQLQQHTAFLPPVPMVHGATPATV

SAATTSATSVPFAATATANQIPIISAEHLTSHKYVTQM
```

In some embodiments, a synthetic MBNL1 protein comprises a first ZF domain that is ZF1-2 and a second ZF domain that is ZF 3-4. Accordingly, in some embodiments, the amino acid sequence of the first ZF domain is SEQ ID NO: 1 or a variant thereof and the amino acid sequence of the second ZF domain is SEQ ID NO: 2 or a variant thereof. In some embodiments, the amino acid sequence of the first ZF domain is a fraction (e.g., 99.9%, 90%, 80%, 60%, 50%, 20% or 10%) of SEQ ID NO: 1 that has the same or higher RNA binding and/or splicing activity as SEQ ID NO: 1. In some embodiments, the amino acid sequence of the second ZF domain is a fraction (e.g., 99.9%, 90%, 80%, 60%, 50%, 20% or 10%) of SEQ ID NO: 2 that has the same or higher RNA binding and/or splicing activity as SEQ ID NO: 2. In some embodiments, the amino acid sequence of the first ZF domain is a fraction (e.g., 99.9%, 90%, 80%, 60%, 50%, 20% or 10%) of SEQ ID NO: 1 that has a lower (e.g., 50-100%) RNA binding and/or splicing activity as SEQ ID NO: 1. In some embodiments, the amino acid sequence of the second ZF domain is a fraction (e.g., 99.9%, 90%, 80%, 60%, 50%, 20% or 10%) of SEQ ID NO: 2 that has a lower (e.g., 50-100%) RNA binding and/or splicing activity as SEQ ID NO: 2. In some embodiments, the amino acid sequence of the first ZF domain is or has at least 80% (e.g., 80, 85, 90, 95, 98, 99, 99.9% or more) sequence identity to SEQ ID NO: 1. In some embodiments, the amino acid sequence of the second ZF domain is or has at least 80% (e.g., 80, 85, 90, 95, 98, 99, 99.9% or more) sequence identity to SEQ ID NO: 2.

In some embodiments, the amino acid sequence of the first ZF domain is SEQ ID NO: 1 or a variant thereof and the amino acid sequence of the second ZF domain is SEQ ID NO: 1 or a variant thereof. In some embodiments, amino acid sequence of the first ZF domain is a fraction (e.g., 99.9%, 90%, 80%, 60%, 50%, 20% or 10%) of SEQ ID NO: 1 that has the same or higher RNA binding and/or splicing activity as SEQ ID NO: 1. In some embodiments, the amino acid sequence of the second ZF domain is a fraction (e.g., 99.9%, 90%, 80%, 60%, 50%, 20% or 10%) of SEQ ID NO: 1 that has the same or higher RNA binding and/or splicing activity as SEQ ID NO: 1. In some embodiments, the amino acid sequence of the first ZF domain is a fraction (e.g., 99.9%, 90%, 80%, 60%, 50%, 20% or 10%) of SEQ ID NO: 1 that has a lower (e.g., 50-100%) RNA binding and/or splicing activity as SEQ ID NO: 1. In some embodiments, the amino acid sequence of the second ZF domain is a fraction (e.g., 99.9%, 90%, 80%, 60%, 50%, 20% or 10%) of SEQ ID NO: 1 that has a lower (e.g., 50-100%) RNA binding and/or splicing activity as SEQ ID NO: 1. In some embodiments, the amino acid sequence of the first ZF domain is or has at least 80% (e.g., 80, 85, 90, 95, 98, 99, 99.9% or more) sequence identity to SEQ ID NO: 1. In some embodiments, the amino acid sequence of the second ZF domain is or has at least 80% (e.g., 80, 85, 90, 95, 98, 99, 99.9% or more) sequence identity to SEQ ID NO: 1

In some embodiments, the amino acid sequence of the first ZF domain is SEQ ID NO: 2 or a variant thereof and amino acid sequence of the second ZF domain is SEQ ID NO: 2 or a variant thereof. In some embodiments, amino acid sequence of the first ZF domain is a fraction (e.g., 99.9%, 90%, 80%, 60%, 50%, 20% or 10%) of SEQ ID NO: 2 that has the same or higher RNA binding and/or splicing activity as SEQ ID NO: 2. In some embodiments, the amino acid sequence of the second ZF domain is a fraction (e.g., 99.9%, 90%, 80%, 60%, 50%, 20% or 10%) of SEQ ID NO: 2 that has the same or higher RNA binding and/or splicing activity as SEQ ID NO: 2. In some embodiments, the amino acid sequence of the first ZF domain is a fraction (e.g., 99.9%, 90%, 80%, 60%, 50%, 20% or 10%) of SEQ ID NO: 2 that has a lower (e.g., 50-100%) RNA binding and/or splicing activity as SEQ ID NO: 2. In some embodiments, the amino acid sequence of the second ZF domain is a fraction (e.g., 99.9%, 90%, 80%, 60%, 50%, 20% or 10%) of SEQ ID NO: 2 that has a lower (e.g., 50-100%) RNA binding and/or splicing activity as SEQ ID NO: 2. In some embodiments, the amino acid sequence of the first ZF domain is or has at least 80% (e.g., 80, 85, 90, 95, 98, 99, 99.9% or more) sequence identity to SEQ ID NO: 2. In some embodiments, the amino acid sequence of the second ZF domain is or has at least 80% (e.g., 80, 85, 90, 95, 98, 99, 99.9% or more) sequence identity to SEQ ID NO: 2.

In some embodiments, the amino acid sequence of the first ZF domain is SEQ ID NO: 2 or a variant thereof and amino acid sequence of the second ZF domain is SEQ ID NO: 1 or a variant thereof. In some embodiments, the amino acid sequence of the first ZF domain is a fraction (e.g., 99.9%, 90%, 80%, 60%, 50%, 20% or 10%) of SEQ ID NO: 2 that has the same or higher RNA binding and/or splicing activity as SEQ ID NO: 2. In some embodiments, the amino acid sequence of the second ZF domain is a fraction (e.g., 99.9%, 90%, 80%, 60%, 50%, 20% or 10%) of SEQ ID NO: 1 that has the same or higher RNA binding and/or splicing activity as SEQ ID NO: 1. In some embodiments, the amino acid sequence of the first ZF domain is a fraction (e.g., 99.9%, 90%, 80%, 60%, 50%, 20% or 10%) of SEQ ID NO: 2 that has a lower (e.g., 50-100%) RNA binding and/or splicing activity as SEQ ID NO: 2. In some embodiments, the amino acid sequence of the second ZF domain is a fraction (e.g., 99.9%, 90%, 80%, 60%, 50%, 20% or 10%) of SEQ ID NO: 1 that has a lower (e.g., 50-100%) RNA binding and/or splicing activity as SEQ ID NO: 1. In some embodiments, the amino acid sequence of the first ZF domain is or has at least 80% (e.g., 80, 85, 90, 95, 98, 99, 99.9% or more) sequence identity to SEQ ID NO: 2. In some embodiments, the amino acid sequence of the second ZF domain is or has at least 80% (e.g., 80, 85, 90, 95, 98, 99, 99.9% or more) sequence identity to SEQ ID NO: 1.

In some embodiments, the RNA binding and splicing activity properties of a fragment of a ZF domain diverge compared to full length sequences as defined by SEQ ID NOs: 1-3. In some embodiments, the RNA binding and/or splicing activity of a fragment of ZF domain as defined by SEQ ID NOs: 1-3 are higher than the RNA binding and/or splicing activity of full-length sequences defined by SEQ ID NOs: 1-3 by 1.1-fold to 200-fold (e.g., 1.1-fold, 2-fold, 5-fold, 50-fold, 100-fold or 200-fold). In some embodiments, ZF domain sequences comprise mutations that result in synthetic MBNL1 proteins of the same or higher RNA binding and/or splicing activity as a non-mutant ZF domain.

In some embodiments, a ZF domain of a synthetic MBNL1 protein has an amino acid sequence that has at least 80% (e.g., 80, 85, 90, 95, 98, 99, 99.9% or more) identity of SEQ ID NO: 1 or SEQ ID NO: 2. In some embodiments, a ZF domain of a synthetic MBNL1 protein has an amino acid sequence of SEQ ID NO: 1, with 75 or less (e.g., 75, 50, 30, 10, 5 or 1) amino acids, 50 or less (e.g., 50, 30, 10, 5 or 1) amino acids, 30 or less (e.g., 30, 10, 5 or 1) amino acids, 10 or less (e.g., 10, 5 or 1) amino acids, or 5 or less (e.g., 5, 4, 3, 2 or 1) amino acids that are changed. In some embodiments, a ZF domain of a synthetic MBNL1 protein has an amino acid sequence of SEQ ID NO: 2, with 75 or less (e.g., 75, 50, 30, 10, 5 or 1) amino acids, 50 or less (e.g., 50, 30, 10, 5 or 1) amino acids, 30 or less (e.g., 30, 10, 5 or 1) amino acids, 10 or less (e.g., 10, 5 or 1) amino acids, or 5 or less (e.g., 5, 4, 3, 2 or 1) amino acids that are changed. In some embodiments, an amino acid change is conservative (e.g., hydrophilic amino acid for another hydrophilic amino acid, or a hydrophobic amino acid for another hydrophobic amino acid). In some embodiments, an amino acid change is not conservative (e.g., a hydrophilic amino acid for a hydrophobic amino acid).

An Example of an Amino Acid Sequence of ZF1-2 (Underlined Amino Acids Represent Coordinating Amino Acids of Zinc Fingers):

```
                                        (SEQ ID NO: 1)
RDTKWLTLEVCREFQRGTCSRPDTECKFAHPSKSCQVENGRVIACFDSLK
GRCSRENCKYLHPPPHLKTQLEINGRNNLIQQKNMAMLAQQMQ
```

An Example of a Nucleotide Sequence of ZF1-2:

```
                                       (SEQ ID NO: 16)
cgggacacaaaatggctaacactggaagtatgtagagagttccagagggg gacttgctcacggccagacacggaatgtaaatttgcacatccttcgaaaa gctgccaagttgaaaatggacgagtaatcgcctgctttgattcattgaaa ggccgttgctccagggagaactgcaaatatcttcatccaccccacattt aaaaacgcagttggagataaatggacgcaataacttgattcagcagaaga acatggccatgttggcccagcaaatgcaa
```

An Example of an Amino Acid Sequence of ZF3-4 (Underlined Amino Acids Represent Coordinating Amino Acids of Zinc Fingers):

```
                                        (SEQ ID NO: 2)
RTDRLEVCREYQRGNCNRGENDCRFAHPADSTMIDTNDNTVTVCMDYIK
GRCSREKCKYFHPPAHLQAKIKAAQYQ
```

An Example of a Nucleotide Sequence of ZF3-4:

```
                                       (SEQ ID NO: 17)
cgaacagacagacttgaggtatgtcgagagtaccaacgtggcaattgcaa ccgaggagaaaatgattgtcggtttgctcatcctgctgacagcacaatga ttgacaccaatgacaacacagtcactgtgtgtatggattacatcaaaggg agatgctctcgggaaaagtgcaaatactttcatccccctgcacatttaca agccaagatcaaggctgcccaataccag
```

In some embodiments, a synthetic MBNL1 protein comprises a linker that has the sequence of WT MBNL1 and is SEQ ID NO: 4. In some embodiments, a linker is truncated. In some embodiments truncation of a linker of MBNL1 protein results in better solubility of the protein. In some embodiments, an amino acid sequence of a linker is selected from the group consisting of: SEQ ID NOs: 4, 12, 13 and 14 or variants thereof. In some embodiments, the linker of a synthetic MBNNL1 protein is truncated and has the sequence of SEQ ID NO: 12. In some embodiments, the linker of a synthetic MBNNL1 protein is truncated and has the sequence of SEQ ID NO: 13. In some embodiments, the linker of a synthetic MBNNL1 protein is truncated and has the sequence of SEQ ID NO: 14. In some embodiments, amino acid sequence of the linker is or has at least 80% (e.g., 80, 85, 90, 95, 98, 99, 99.9% or more) sequence identity to a sequence selected from the group consisting of: SEQ ID NO: 4, SEQ ID NO: 12, SEQ ID NO: 13, and SEQ ID NO: 14. In some embodiments, the linker of a synthetic MBNL1 protein comprises the sequence of SEQ ID NO. 14. In some embodiments, a linker is 5-200 amino acids (e.g., about 5, 10, 19, 38, 57, 76, 100, 114, 152 or 200 amino acids), 5-50 amino acids (e.g., about 5, 25 or 50 amino acids), 50-100 amino acids (e.g., about 50, 80 or 100 amino acids), or 100-200 amino acids (e.g., about 100, 150 or 200 amino acids) long. In some embodiments, a linker is 15-80 amino acids long (e.g., 19, 38 or 76 amino acids long). In some embodiments, a linker is 100-200 amino acids long (e.g., 100, 114, 152, 180 or 200 amino acids long). In some embodiments, a linker comprises multiple copies of any of the sequences SEQ ID NOs: 4, 12, 13 and 14. For example a linker may comprise two copies of the sequence of SEQ ID NO: 14. In some embodiments, a linker comprises 1-18 of the 19 amino acids (e.g., 1, 2, 3, 4, 5, 6, 7, 8, 9, 10, 11, 12, 13, 14, 15, 16, 17 or 18 amino acids) of SEQ ID NO: 14.

An Example of an Amino Acid Sequence of Full-Length MBNL1 Linker (76 Amino Acids):

```
                                            (SEQ ID NO: 4)
LANAMMPGAPLQPVPMFSVAPSLATNASAAAFNPYLGPVSPSLVPAEILP
TAPMLVTGNPGVPVPAAAAAAAQKLM
```

An Example of a Nucleotide Sequence of Full-Length MBNL1 Linker:

```
                                           (SEQ ID NO: 18)
ctagccaatgccatgatgcctggtgcccattacaacccgtgccaatgtt ttcagttgcaccaagcttagccaccaatgcatcagcagccgcctttaatc cctatctgggacctgtttctccaagcctggtcccggcagagatcttgccg actgcaccaatgttggttacagggaatccgggtgtccctgtacctgcagc tgctgcagctgctgcacagaaattaatg
```

An Example of an Amino Acid Sequence of Truncated MBNL1 Linker L57 (57 Amino Acids):

```
                                           (SEQ ID NO: 12)
LANAMMPGAPLQPVPMFSVAPSLATNASILPTAPMLVTGNPGVPVPAAAA
AAAQKLM
```

An Example of an Amino Acid Sequence of Truncated MBNL1 Linker L38 (38 Amino Acids):

```
                                           (SEQ ID NO: 13)
LANAMMPGAPLQPVPMFSVGNPGVPVPAAAAAAAQKLM
```

An Example of an Amino Acid Sequence of Truncated MBNL1 Linker L19 (19 Amino Acids):

```
                                           (SEQ ID NO: 14)
LANAMMPGAAAAAAAQKLM
```

In some embodiments, a synthetic MBNL1 protein has a nuclear localization signal (NLS). In some embodiments, a NLS signal is positioned at the C-terminus end of a synthetic MBNL1 protein. In some embodiments, a NLS is monopartite. Monopartite NLSs have a single cluster of basic amino acid residues. In some embodiment, a NLS in a synthetic MBNL1 protein is bipartite. Bipartite NLSs have two clusters of basic amino acids separated by an acid linker. In some embodiments, a linker between the two clusters of basic amino acid clusters of a bipartite NLS is 5-15 amino acids long. In some embodiments, a linker between the two clusters of basic amino acid clusters of a bipartite NLS is 10-12 amino acids long. In some embodiments, a monopartite NLS has at least four consecutive basic amino acids. An example of a monopartite NLS with at least four consecutive basic amino acids is SV40 large T antigen NLS. In some embodiments, an SV40 large T antigen NLS has the amino acid sequence: PKKKRKV (SEQ ID NO: 40). In some embodiments, an SV40 large T antigen NLS has the amino acid sequence of SEQ ID NO: 3.

An Example of a NLS SV40 Large T Antigen NLS has the Amino Acid Sequence:

```
                                            (SEQ ID NO: 3)
PKKKRKVE
```

In some embodiments, a monopartite NLS having only three basic amino acids is represented by amino acid sequence: K(K/R)X(K/R). An example of a monopartite NLS having only three basic amino acids is c-Myc NLS with an amino acid sequence: PAAKRVKLD (SEQ ID NO: 31).

In some embodiments, a synthetic MBNL1 protein comprises a tag. In some embodiments, a synthetic MBNL1 protein comprises a tag in the N-terminus end of the protein. In some embodiments, a synthetic MBNL1 protein comprises a tag in the N-terminus end of the protein after 1-10 amino acids (e.g., 1, 2, 5, 8 or 10 amino acids). In some embodiments, a synthetic MBNL1 protein comprises more than one tag (e.g., two, three or four tags). In some embodiments, multiple tags comprised in a synthetic MBNL1 protein are the same. In some embodiments, multiple tags comprised in a synthetic MBNL1 protein are different. For example, a synthetic MBNL1 protein can comprise an HA tag and a GST tag. In some embodiments, a tag is a peptide tag. Some examples of peptide tags are His-tag (SEQ ID NO: 5), HA-tag, c-myc-tag, FLAG-tag, 3×FLAG-tag, streptag, E-tag and V5tag. In some embodiments, a tag is a protein tag. Some examples of peptide tags are glutathione-S-transferase-tag (GST), Fc-tag, thioredoxin-tag, biotin-tag and maltose binding protein-tag.

An Example of an Amino Acid Sequence of HA-Tag:

```
                                            (SEQ ID NO: 5)
YPYDVPDYA
```

The following are some examples of sequences (SEQ ID NOs: 6-11 and 19-24) of synthetic MBNL1 proteins that have truncated C-termini and that comprise ZF1-2 and/or ZF3-4, a linker, a NLS in the C-terminus and an HA-tag in the N-terminus. NLS sequences are in the C-terminus, and HA-tag sequences in the N-terminus are bolded. The first ZF domain is underlined and the second ZF domain is double underlined. Linker sequences are represented by the italicized amino acids between the first and second ZF domains. It is to be understood that, compared to the WT MBNL1 sequence or the following sequences, sequences that comprise minor amino acid differences to enable cloning (e.g., altering amino acids to incorporate cleavage sites by restriction enzymes) are also disclosed herein. In some embodiments, a synthetic MBNL1 protein does not include an N-terminal tag.

An Example of an Amino Acid Sequence of WT-MBNL1, (280aa):

```
                                            (SEQ ID NO: 6)
MEYPYDVPDYAGSAVSVTPIRDTKWLTLEVCREFQRGTCSRPDTECKFA

HPSKSCQVENGRVIACFDSLKGRCSRENCKYLHPPPHLKTQLEINGRNN

LIQQKNMAMLAQQMQ*LANAMMPGAPLQPVPMFSVAPSLATNASAAAFNP*

*YLGPVSPSLVPAEILPTAPMLVTGNPGVPVPAAAAAAAQKLM*RTDRLEV

CREYQRGNCNRGENDCRFAHPADSTMIDTNDNTVTVCMDYIKGRCSREK

CKYFHPPAHLQAKIKAAQYQVNQAAAAPKKKRKVE
```

An Example of a Nucleic Acid Sequence of WT-MBNL1:

(SEQ ID NO: 19)

ATGgagtacccatacgacgtaccagattacgctggatccgctgttagtgtcacaccaattcgggacacaaaatggctaacactggaagtatgtagagagttccagagggggacttgctcacggccagacacggaatgtaaatttgcacatccttcgaaaagctgccaagttgaaaatggacgagtaatcgcctgctttgattcattgaaaggccgttgctccagggagaactgcaaatatcttcatccaccccacatttaaaaacgcagttggagataaatggacgcaataacttgattcagcagaagaacatggccatgttggcccagcaaatgcaactagccaatgccatgatgcctggtgccccattacaacccgtgccaatgtttcagttgcaccaagcttagccaccaatgcatcagcagccgcctttaatccctatctgggacctgtttctccaagcctggtcccggcagagatcttgccgactgcaccaatgttggttacagggaatccgggtgtccctgtacctgcagctgctgcagctgctgcacagaaattaatgcgaacagacagacttgaggtatgtcgagagtaccaacgtggcaattgcaaccgaggagaaaatgattgtcggtttgctcatcctgctgacagcacaatgattgacaccaatgacaacacagtcactgtgtgtatggattacatcaaagggagatgctctcgggaaaagtgcaaatactttcatcccctgcacatttacaagccaagatcaaggctgcccaataccaggtcaaccaggctgcagctgcaCAAAAAAGAAGAGAAAGGTCGAA_TGA_

An Example of an Amino Acid Sequence of MBNL1(1-2, 1-2), (296aa):

(SEQ ID NO: 7)

MEYPYDVPDYAMAVSVTPI<u>RDTKWLTLEVCREFQRGTCSRPDTECKFAH PSKSCQVENGRVIACFDSLKGRCSRENCKYLHPPPHLKTQLEINGRNNL IQQKNMAMLAQQMQ</u>LANAMMPGAPLQPVPMFSVAPSLATNASAAAFNPY LGPVSPSLVPAEILPTAPMLVTGNPGVPVPAAAAAAAQKLM<u>RDTKWLTL EVCREFQRGTCSRPDTECKFAHPSKSCQVENGRVIACFDSLKGRCSREN CKYLHPPPHLKTQLEINGRNNLIQQKNMAMLAQQMQ</u>VNQAAAAPKKKRK VE

An Example of a Nucleic Acid Sequence of MBNL1(1-2, 1-2):

(SEQ ID NO: 20)

ATGgagtacccatacgacgtaccagattacgctatggctgttagtgtcacaccaattcgggacacaaaatggctaacactggaagtatgtagagagttccagagggggacttgctcacggccagacacggaatgtaaatttgcacatccttcgaaaagctgccaagttgaaaatggacgagtaatcgcctgctttgattcattgaaaggccgttgctccagggagaactgcaaatatcttcatccaccccacatttaaaaacgcagttggagataaatggacgcaataacttgattcagcagaagaacatggccatgttggcccagcaaatgcaa*ctagccaatgccatgatgcctggtgcccattacaacccgtgccaatgttttcagttgcaccaagcttagccaccaatgcatcagcagccgcctttaatccctatctgggacctgtttctccaagcctggtcccggcagagatcttgccgactgcaccaatgttggttacagggaatccgggtgtccctgtacctgcagctgctgca*gctgctgcacagaaattaatgcgggacacaaaatggctaacactggaagtatgtagagagttccagagggggacttgctcacggccagacacggaatgtaaatttgcacatccttcgaaaagctgccaagttgaaaatggacgagtaatcgcctgctttgattcattgaaaggccgttgctccagggagaactgcaaatatcttcatccaccccacatttaaaaacgcagttggagataaatggacgcaataacttgattcagcagaagaacatggccatgttggcccagcaaatgcaagtcaaccaggctgcagctgcaCCAAAAAAGAAGAGAAAGGTCGAA_TGA_

An Example of an Amino Acid Sequence of MBNL1(3-4, 3-4), (262aa):

(SEQ ID NO: 8)
MEYPYDVPDYAMAVSVTPIRTDRLEVCREYQRGNCNRGENDCRFAHPAD
STMIDTNDNTVTVCMDYIKGRCSREKCKYFHPPAHLQAKIKAAQYQLAN
AMMPGAPLQPVPMFSVAPSLATNASAAAFNPYLGPVSPSLVPAEILPTA
PMLVTGNPGVPVPAAAAAAAQKLMRTDRLEVCREYQRGNCNRGENDCRF
AHPADSTMIDTNDNTVTVCMDYIKGRCSREKCKYFHPPAHLQAKIKAAQ
YQVNQAAAAPKKKRKVE

An Example of a Nucleic Acid Sequence of MBNL1(3-4, 3-4):

(SEQ ID NO: 21)
ATGgagtacccatacgacgtaccagattacgctatggctgttagtgtcac accaattcgaacagacagacttgaggtatgtcgagagtaccaacgtggca
attgcaaccgaggagaaaatgattgtcggtttgctcatcctgctgacagc
acaatgattgacaccaatgacaacacagtcactgtgtgtatggattacat
caaagggagatgctctcgggaaaagtgcaaatactttcatcccctgcac
atttacaagccaagatcaaggctgcccaataccagctagccaatgccatg
atgcctggtgcccattacaacccgtgccaatgttttcagttgcaccaag
cttagccaccaatgcatcagcagccgcctttaatccctatctgggacctg
tttctccaagcctggtcccggcagagatcttgccgactgcaccaatgttg
gttacagggaatccgggtgtccctgtacctgcagctgctgcagctgctgc
acagaaattaatgcgaacagacagacttgaggtatgtcgagagtaccaac
gtggcaattgcaaccgaggagaaaatgattgtcggtttgctcatcctgc
tgacagcacaatgattgacaccaatgacaacacagtc
actgtgtgtatggattacatcaaagggagatgctctcgggaaaagtgca
aatactttcatcccctgcacatttacaagccaagatcaaggct gcccaataccaggtcaaccaggctgcagctgcaCCAAAAAAGAAGA
GAAAGGTCGAATGA An Example of an Amino Acid Sequence of WT-MBNL1-L57, (261aa, Amino Acids Long):

(SEQ ID NO: 9)
MEYPYDVPDYAGSAVSVTPIRDTKWLTLEVCREFQRGTCSRPDTECKFAH
PSKSCQVENGRVIACFDSLKGRCSRENCKYLHPPPHLKTQLEINGRNNLI
QQKNMAMLAQQMQLANAMMPGAPLQPVPMFSVAPSLATNASILPTAPMLV
TGNPGVPVPAAAAAAAQKLMRTDRLEVCREYQRGNCNRGENDCRFAHPAD
STMIDTNDNTVTVCMDYIKGRCSREKCKYFHPPAHLQAKIKAAQYQVNQA
AAAPKKKRKVE

An Example of a Nucleic Acid Sequence of WT-MBNL1-L57:

(SEQ ID NO: 22)
ATGgagtacccatacgacgtaccagattacgctggatccgctgttagtgtcacaccaattcgggacacaaaatggctaacactggaag tatgtagagagttccagaggggggacttgctcacggccagacacggaatgtaaatttgcacatccttcgaaaagctgccaagttgaaaatgg acgagtaatcgcctgctttgattcattgaaaggccgttgctccagggagaactgcaaatatcttcatccaccccacatttaaaaacgcagttg gagataaatggacgcaataacttgattcagcagaagaacatggccatgttggcccagcaaatgcaactagccaatgccatgatgcctggt gccccattacaacccgtgccaatgttttcagttgcaccaagcttagccaccaatgcatcaatcttgccgactgcaccaatgttggttacag ggaatccgggtgtccctgtacctgcagctgctgcagctgctgcacagaaattaatgcgaacagacagacttgaggtatgtcgagagtac caacgtggcaattgcaaccgaggagaaaatgattgtcggtttgctcatcctgctgacagcacaatgattgacaccaatgacaacacagtcac tgtgtgtatggattacatcaaagggagatgctctcgggaaaagtgcaaatactttcatcccctgcacatttacaagccaagatcaaggctgc ccaataccaggtcaaccaggctgcagctgcaCCAAAAAAGAAGAGAAAGGTCGAATGA An Example of an Amino Acid Sequence of WT-MBNL1-L38, (242aa, Liner 38 Amino Acids Long):

(SEQ ID NO: 10)
MEYPYDVPDYAGSAVSVTPIRDTKWLTLEVCREFQRGTCSRPDTECKFAH
PSKSCQVENGRVIACFDSLKGRCSRENCKYLHPPPHLKTQLEINGRNNLI
QQKNMAMLAQQMQLANAMMPGAPLQPVPMFSVGNPGVPVPAAAAAAAQKL
MRTDRLEVCREYQRGNCNRGENDCRFAHPADSTMIDTNDNTVTVCMDYIK
GRCSREKCKYFHPPAHLQAKIKAAQYQVNQAAAAPKKKRKVE

An Example of a Nucleic Acid Sequence of WT-MBNL1-L38:

(SEQ ID NO: 23)

ATGgagtacccatacgacgtaccagattacgctggatccgctgttagtgtcacaccaattcgggacacaaaatggctaacactggaag tatgtagagagttccagaggggacttgctcacggccagacacggaatgtaaatttgcacatccttcgaaaagctgccaagttgaaaatgg acgagtaatcgcctgctttgattcattgaaaggccgttgctccagggagaactgcaaatatcttcatccaccccacatttaaaaacgcagttg gagataaatggacgcaataacttgattcagcagaagaacatggccatgttggcccagcaaatgcaactagccaatgccatgatgcctggt gccccattacaacccgtgccaatgttttcagttgggaatccgggtgtccctgtacctgcagctgctgcagctgctgcacagaaattaatg cgaacagacagacttgaggtatgtcgagagtaccaacgtggcaattgcaaccgaggagaaaatgattgtcggtttgctcatcctgctgaca gcacaatgattgacaccaatgacaacacagtcactgtgtgtatggattacatcaaagggagatgctctcgggaaaagtgcaaatactttcatc cccctgcacatttacaagccaagatcaaggctgcccaataccaggtcaaccaggctgcagctgcaCCAAAAAAGAAGAG

AAAGGTCGAATGA

An Example of an Amino Acid Sequence of WT-MBNL1-L19, (223aa, Liner 19 Amino Acids Long):

(SEQ ID NO: 11)
MEYPYDVPDYAGSAVSVTPIRDTKWLTLEVCREFQRGTCSRPDTECKFAH

PSKSCQVENGRVIACFDSLKGRCSRENCKYLHPPPHLKTQLEINGRNNLI

QQKNMAMLAQQMQLANAMMPGAAAAAAAQKLMRTDRLEVCREYQRGNCN

RGENDCRFAHPADSTMIDTNDNTVTVCMDYIKGRCSREKCKYFHPPAHLQ

AKIKAAQYQVNQAAAAPKKKRKVE

An Example of a Nucleic Acid Sequence of WT-MBNL1-L19:

(SEQ ID NO: 24)

ATGgagtacccatacgacgtaccagattacgctggatccgctgttagtgtcacaccaattcgggacacaaaatggctaacactggaag tatgtagagagttccagaggggacttgctcacggccagacacggaatgtaaatttgcacatccttcgaaaagctgccaagttgaaaatgg acgagtaatcgcctgctttgattcattgaaaggccgttgctccagggagaactgcaaatatcttcatccaccccacatttaaaaacgcagttg gagataaatggacgcaataacttgattcagcagaagaacatggccatgttggcccagcaaatgcaactagccaatgccatgatgcctggt gccgctgctgcagctgctgcacagaaattaatgcgaacagacagacttgaggtatgtcgagagtaccaacgtggcaattgcaaccgagg agaaaatgattgtcggtttgctcatcctgctgacagcacaatgattgacaccaatgacaacacagtcactgtgtgtatggattacatcaaagg gagatgctctcgggaaaagtgcaaatactttcatcccctgcacatttacaagccaagatcaaggctgcccaataccaggtcaaccaggct gcagctgcaCCAAAAAAGAAGAGAAAGGTCGAATGA Synthetic MBNL proteins that have cell penetrating capabilities are also contemplated herein. In some embodiments, such synthetic proteins are fused to cell-penetrating peptides (CPPs). Several CPPs are known in the art, any one of which can be used herein. Examples of CCPs are HIV-TAT CPP and 8× Arginine CPP. FIG. 17A shows example configurations of synthetic MBNL proteins that are fused to CPPs. SEQ ID NOs: 75 and 76 provide example amino acid sequences for HIV-TAT and 8× Arginine CPPs, respectively. An Example of an Amino Acid Sequence of HIV-TAT CPP:

(SEQ ID NO: 75)
YGRKKRRQRRR

An Example of an Amino Acid Sequence of 8× Arginine CPP:

(SEQ ID NO: 76)
RRRRRRRR

Synthetic MBNL proteins with shorter linkers are also contemplated herein. Linkers can be of up to 76 amino acids in length, e.g., 19, 38, 57 or 76 amino acids. FIG. 17B provides examples of synthetic MBNL proteins with shorter linkers. In some embodiments, In some embodiments, the strategy to engineer synthetic MBNL proteins focuses on replacement of the ZF3-4 general RNA binding domain with other non-specific RNA binding domains (RBDs). These may include RGG boxes (arginine-glycine rich domains) and double-stranded RNA binding domains (dsRBDs). RDBs may also include RBFOX, RS or HIV nucleocapsid (NC) domains. RS domains contain repeating arginines and serines important in splicing regulation. HIV nucleocapsid (HIV NC) domain is a ZF domain that binds RNA with low specificity and has chaperone (RNA folding) activity.

RGG boxes act as non-specific RBDs in many proteins throughout the human genome, including hnRNP U. dsRBDs bind double-stranded RNA in a sequence independent manner. Fusion of dsRBDs from (examples here include human TRBP and Xenopus laevis Xlbpra) could improve targeting of MBNL1 to the toxic CUG/CCUG repeat RNA expressed in DM1 and DM2. These RNAs are predicted to form double-stranded RNA structures in the cell. Targeting of a ZF1-2-dsRBD fusion to the repeat RNA could displace endogenous MBNL1 in patient cells.

Figure 21:
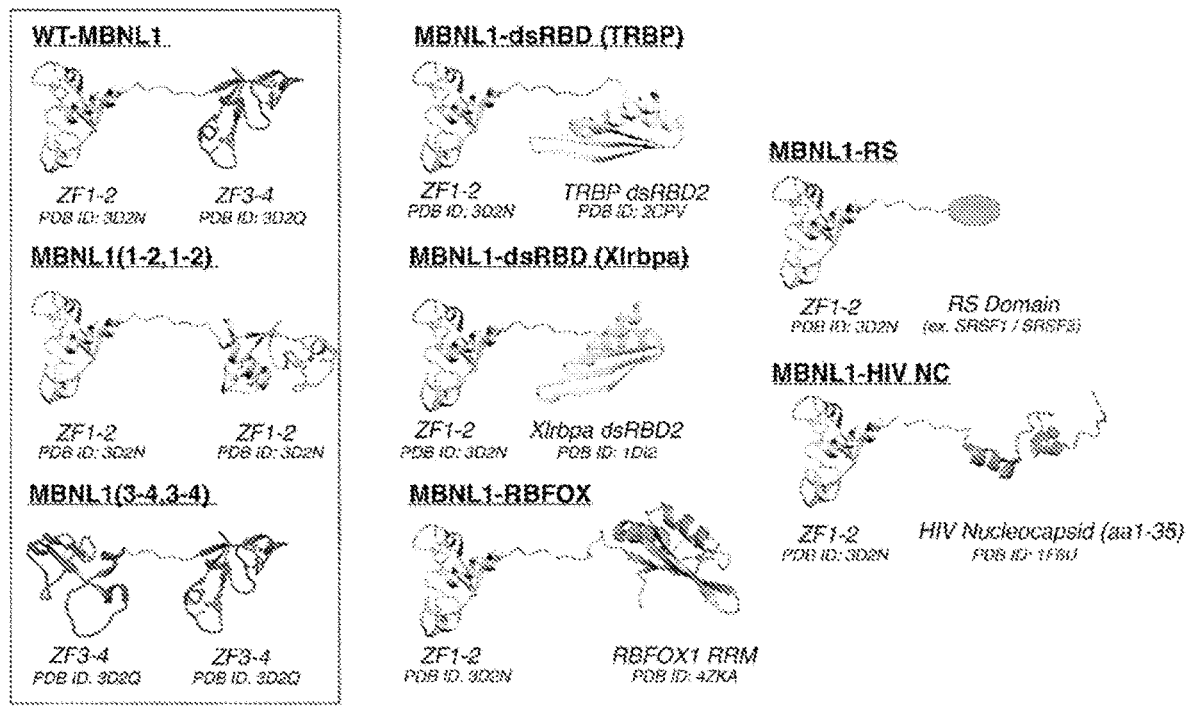
FIG. 21 provides a depiction of either crystal or NMR structures for NA binding domains, and as such provides size for each synthetic protein.

FIG. 17C and FIG. 21 provide examples of synthetic MBNL proteins with RBD. SEQ ID NOs: 77 and 78 provide example amino acid sequences for TRBP-dsRBD2 and Xlbpra-dsRBD2, respectively. In some embodiments, an RDB is hnRNP U RGG. SEQ ID NOs: 81-83 provide examples of nucleic acid sequences that encode HIV NC, RBFOX and an RS domains, respectively. SEQ ID NOs: 87-89 provide examples of amino acid sequences for HIV NC, RBFOX and an RS domains, respectively.

An Example of an Amino Acid Sequence of TRBP-dsRBD2:

(SEQ ID NO: 77)
SPQQSECNPVGALQELVVQKGWRLPEYTVTQESGPAHRKEFTMTCRVERF
IEIGSGTSKKLAKRNAAAKMLLRVHTVPLDARDG

An Example of an Amino Acid Sequence of Xlbpra-dsRBD2:

(SEQ ID NO: 78)
QENPVGSLQELAVQKGWRLPEYTVAQESGPPHKREFTITCRVETFVETGS
GTSKQVAKRVAAEKLLTKFKTIS

An Example of a Nucleic Acid Sequence Encoding HIV NC:

(SEQ ID NO: 81)
ATTCAAAAAGGGAACTTCAGGAACCAACGGAAAACTGTCAAATGCTTTAA
TTGTGGAAAGGAAGGCCATATAGCAAAAAATTGTAGAGCACCAAGAAAAA
AGGGG

An Example of an Amino Acid Sequence of HIV NC (1-35aa):

(SEQ ID NO: 87)
IQKGNFRNQRKTVKCFNCGKEGHIAKNCRAPRKKG

An Example of a Nucleic Acid Sequence Encoding RBFOX RNA Recognition Domain (RRM):

(SEQ ID NO: 82)
AACACGGAAAACAAGTCTCAGCCCAAGCGGCTGCATGTCTCCAATATCCC

CTTCAGGTTCCGGGATCCGGACCTCAGACAAATGTTTGGTCAATTTGGTA

AAATCTTAGATGTTGAAATTATTTTTAATGAGCGAGGCTCAAAGGGATTT

GGTTTCGTAACTTTCGAAAATAGTGCCGATGCGGACAGGGCGAGGGAGAA

ATTACACGGCACCGTGGTAGAGGGCCGTAAAATCGAGGTAAATAATGCCA

CAGCACGTGTAATGACAAATAAAAAGACCGTCAACCCTTATACAAATGGC

An Example of an Amino Acid Sequence of RBFOX RNA Recognition Domain (RRM):

(SEQ ID NO: 88)
NTENKSQPKRLHVSNIPFRFRDPDLRQMFGQFGKILDVEIIFNERGSKGF
GFVTFENSADADRAREKLHGTVVEGRKIEVNNATARVMTNKKTVNPYTNG

An Example of a Nucleic Acid Sequence Encoding SRSF3 RS Domain:

(SEQ ID NO: 83)
AGAAGTAGAAATCGTGGCCCACCTCCCTCTTGGGGTCGTCGCCCTCGAGA

TGATTATCGTAGGAGGAGTCCTCCACCTCGTCGCAGATCTCCAAGAAGGA

GAAGCTTCTCTCGCAGCCGGAGCAGGTCCCTTTCTAGAGATAGGAGAAGA

GAGAGATCGCTGTCTCGGGAGAGAAATCACAAGCCGTCCCGATCCTTCTC

TAGGTCTCGTAGTCGATCTAGGTCAAATGAAAGGAAA

An Example of an Amino Acid Sequence of SRSF3 RS Domain:

(SEQ ID NO: 89)
RSRNRGPPPSWGRRPRDDYRRRSPPPRRRSPRRRSFSRSRSRSLSRDRRR
ERSLSRERNHKPSRSFSRSRSRSRSNERK

The following are some examples of sequences (SEQ ID NOs: 25-30) of synthetic minimal MBNL1 proteins that contain ZF1-2-CPP fusions, MBNL1-Linkers, and ZF1-2 non-specific RBD fusion proteins. The HA-tag is represented by the italicized amino acids and the His-tag corresponds to the bold amino acids (HHHHHH, SEQ ID NO: 74). The ZF1-2 domain sequence is in underlined and bolded. The mblZF1-2 domain sequence is double underlined. The sequences for RNA binding domains (RBDs) are in italics and underlined, the HIV TAT cell-penetrating peptide domain (HIV TAT CPP) is in italics and the arginine cell-penetrating peptide domains (8× Arg CPP) are in bold italics.

An Example of an Amino Acid Sequence of ZF1-2-TRBP-dsRBD2:

(SEQ ID NO: 25)
ME*YPYDVPDY*AMAVSVTPIRDTKWLTLEVCREFORGTCSRPDTECKFAHP

SKSCQVENGRVIACFDSLKGRCSRENCKYLHPPPHLKTQLEINGRNNLIQ

QKNMAMLAQQMQLANAMMPGAPLQPVPMFSVAPSLATNASAAAFNPYLGP

VSPSLVPAEILPTAPMLVTGNPGVPVPAAAAAAAQKLM*SPQQSECNPVGA*

*LQELVVQKGWRLPEYTVTQESGPAHRKEFTMTCRVERFIEIGSGTSKKLA*

*KRNAAAKMLLRVHTVPLDARDG*YGRKKRRQRRR

An Example of an Amino Acid Sequence of ZF1-2-Xlbpra-dsRBD2:

(SEQ ID NO: 26)
ME*YPYDVPDY*AMAVSVTPIRDTKWLTLEVCREFQRGTCSRPDTECKFAHP

SKSCQVENGRVIACFDSLKGRCSRENCKYLHPPPHLKTQLEINGRNNLIQ

QKNMAMLAQQMQLANAMMPGAPLQPVPMFSVAPSLATNASAAAFNPYLGP

VSPSLVPAEILPTAPMLVTGNPGVPVPAAAAAAAQKLM*QENPVGSLQELA*

*VQKGWRLPEYTVAQESGPPHKREFTITCRVETFVETGSGTSKQVAKRVAA*

*EKLLTKFKTIS*YGRKKRRQRRR

An Example of an Amino Acid Sequence of mblZF1-2—HIV TAT CPP:

(SEQ ID NO: 27)
MHHHHHHANVVNMNSLLNGKDSRWLQLEVCREFQRNKCSRQDTECKFAH
PPANVEVQNGKVTACYDSIKGRCNRDKPPCKYFHPPQHLKDQLLINGRN
HLALKNALMQQMG*YGRKKRRQRRR*

An Example of an Amino Acid Sequence of mblZF1-2-8× Arg CPP:

(SEQ ID NO: 28)
MHHHHHHANVVNMNSLLNGKDSRWLQLEVCREFQRNKCSRQDTECKFAH
PPANVEVQNGKVTACYDSIKGRCNRDKPPCKYFHPPQHLKDQLLINGRN
HLALKNALMQQMG*RRRRRRRR*

An Example of an Amino Acid Sequence of ZF1-2—HIV TAT CPP:

(SEQ ID NO: 29)
MHHHHHHMAVSVTPIRDTKWLTLEVCREFQRGTCSRPDTECKFAHPSKSC
QVENGRVIACFDSLKGRCSRENCKYLHPPPHLKTQLEYGRKKRRQRRR

An example of an amino acid sequence of ZF1-2-8× Arg CPP:

(SEQ ID NO: 30)
MHHHHHHMAVSVTPI<u>RDTKWLTLEVCREFQRGTCSRPDTECKFAHPSKS
CQVENGRVIACFDSLKGRCSRENCKYLHPPPHLKTQLEINGRNNLIQQ
KNMAMLAQQMQ</u>RRRRRRRR

An Example of an Amino Acid Sequence of mblZF1-2:

(SEQ ID NO: 79)
<u>ANVVNMNSLLNGKDSRWLQLEVCREFQRNKCSRQDTECKFAHPPANVEVQ
NGKVTACYDSIKGRCNRDKPPCKYFHPPQHLKDQLLINGRNHLALKNALM
QQMG</u>

The following are some examples of nucleic acid sequences (SEQ ID NOs: 84-86) encoding synthetic MBNL proteins (SEQ ID NOs: 90-92) that contain HIV NC, RBFOX RRM or an RS domain.

An Example of a Nucleic Acid Sequence Encoding a MBNL1-NC(1-35) Fusion Protein:

(SEQ ID NO: 84)
ATGGAG<u>TACCCATACGACGTACCAGATTACGCT</u>atgGCTGTTAGTGTCACACCAATTC

GGGACACAAAATGGCTAACACTGGAAGTATGTAGAGAGTTCCAGAGGGGACT

TGCTCACGGCCAGACACGGAATGTAAATTTGCACATCCTTCGAAAAGCTGCCA

AGTTGAAAATGGACGAGTAATCGCCTGCTTTGATTCATTGAAAGGCCGTTGCT

CCAGGGAGAACTGCAAATATCTTCATCCACCCCCACATTTAAAAACGCAGTTG

GAGATAAATGGACGCAATAACTTGATTCAGCAGAAGAACATGGCCATGTTGGC

CCAGCAAATGCAA<u>CTAGCCAATGCCATGATGCCTGGTGCCCCATTACAACCCGTGC</u>

<u>CAATGTTTTCAGTTGCACCAAGCTTAGCCACCAATGCATCAGCAGCCGCCTTTAATC</u>

<u>CCTATCTGGGACCTGTTTCTCCAAGCCTGGTCCCGGCAGAGATCTTGCCGACTGCAC</u>

<u>CAATGTTGGTTACAGGGAATCCCGGGGTCCCTGTACCTGCAGCTGCTGCAGCTGCTG</u>

<u>CACAGAAATTAATG</u>*ATTCAAAAAGGGAACTTCAGGAACCAACGGAAAACTGTCAAAT*

*GCTTTAATTGTGGAAAGGAAGCCATATAGCAAAAAATTGTAGAGCACCAAGAAAAAA*

*GGGG*TATGGTCGTAAAAAACGCCGCCAGCGTCGCCGCtga
where:
HATag
MBNL1 ZF1-2
<u>Linker Region (from region between MBNL1 ZF1-2 and ZF3-4)</u>
*HIV Nucleocapsid 1-35aa*
HIVTATCPP An Example of an Amino Acid Sequence of MBNL1-NC (1-35) Fusion:

(SEQ ID NO: 90)
ME*YPYDVPDYA*MAVSVTPI<u>RDTKWLTLEVCREFQRGTCSRPDTECKFAHPSKSCQVEN</u>

<u>GRVIACFDSLKGRCSRENCKYLHPPPHLKTQLEINGRNNLIQQKNMAMLAQQMQ</u>LANA

MMPGAPLQPVPMFSVAPSLATNASAAAFNPYLGPVSPSLVPAEILPTAPMLVTGNP

GVPVPAAAAAAQKLM<u>IQKGNFRNQRKTVKCFNCGKEGHIAKNCRAPRKKG</u>*YGRKK*

*RRQRRR*
where:
*HA Tag*
<u>MBNL1ZF1-2</u>
Linker Region (from region between MBNL1 ZF1-2 and ZF3-4)
<u>HIV Nucleocapsid 1-35aa</u>
*HIV TAT CPP*

An Example of a Nucleic Acid Sequence Encoding a MBNL1-RBFOX1 Fusion Protein:

(SEQ ID NO: 85)
ATGGAG<u>TACCCATACGACGTACCAGATTACGCT</u>ATGGCTGTTAGTGTCACACCAATT

CGGGACACAAAATGGCTAACACTGGAAGTATGTAGAGAGTTCCAGAGGGGGA

CTTGCTCACGGCCAGACACGGAATGTAAATTTGCACATCCTTCGAAAAGCTGC

CAAGTTGAAAATGGACGAGTAATCGCCTGCTTTGATTCATTGAAAGGCCGTTG

CTCCAGGGAGAACTGCAAATATCTTCATCCACCCCCACATTTAAAAACGCAGTT

GGAGATAAATGGACGCAATAACTTGATTCAGCAGAAGAACATGGCCATGTTGG

CCCAGCAAATGCAA<u>CTAGCCAATGCCATGATGCCTGGTGCCCCATTACAACCCGTG</u>

<u>CCAATGTTTTCAGTTGCACCAAGCTTAGCCACCAATGCATCAGCAGCCGCCTTTAAT</u>

<u>CCCTATCTGGGACCTGTTTCTCCAAGCCTGGTCCCGGCAGAGATCTTGCCGACTGCA</u>

<u>CCAATGTTGGTTACAGGGAATCCGGGTGTCCCTGTACCTGCAGCTGCTGCAGCTGCT</u>

<u>GCACAGAAATTAATG</u>*AACACGGAAAACAAGTCTCAGCCCAAGCGGCTGCATGTCTCC*

*AATATCCCCTTCAGGTTCCGGGATCCGGACCTCAGACAAATGTTTGGTCAATTTGGTA*

*AAATCTTAGATGTTGAAATTATTTTTAATGAGCGAGGCTCAAAGGGATTTGGTTTCGT*

*AACTTTCGAAAATAGTGCCGATGCGGACAGGGCGAGGGAGAAATTACACGGCACCGT*

*GGTAGAGGGCCGTAAAATCGAGGTAAATAATGCCACAGCACGTGTAATGACAAATAA*

*AAAGACCGTCAACCCTTATACAAATGGC*<u>CCAAAAAAGAAGAGAAAGGTCGAA</u>TGA
Where:
<u>HATag</u>
MBNL1 ZF1-2
<u>Linker Region (from region between MBNL1 ZF1-2 and ZF3-4)</u>
*RBFOX RRM*
<u>NLS</u>

An Example of an Amino Acid Sequence of MBNL1-RBFOX1 Fusion:

(SEQ ID NO: 91)
ME*YPYDVPDYA*MAVSVTPI<u>RDTKWLTLEVCREFQRGTCSRPDTECKFAHPSKSCQVEN</u>

<u>GRVIACFDSLKGRCSRENCKYLHPPPHLKTQLEINGRNNLIQQKNMAMLAQQMQ</u>LANA

MMPGAPLQPVPMFSVAPSLATNASAAAFNPYLGPVSPSLVPAEILPTAPMLVTGNP

GVPVPAAAAAAQKLM<u>NTENKSQPKRLHVSNIPFRFRDPDLRQMFGQFGKILDVEIIFN</u>

<u>ERGSKGFGFVTFENSADADRAREKLHGTVVEGRKIEVNNATARVMTNKKTVNPYTNG</u>

*PKKKRKVE*
where:
*HA Tag*
<u>MBNL1ZF1-2</u>
Linker Region (from region between MBNL1 ZF1-2 and ZF3-4)
<u>RBFOX RRM</u>
*SV40 NLS*

An Example of a Nucleic Acid Sequence Encoding a MBNL1-RS Fusion Protein:

(SEQ ID NO: 86)
ATGGAG<u>TACCCATACGACGTACCAGATTACGCT</u>ATGGCTGTTAGTGTCACACCAATT

CGGGACACAAAATGGCTAACACTGGAAGTATGTAGAGAGTTCCAGAGGGGGA

CTTGCTCACGGCCAGACACGGAATGTAAATTTGCACATCCTTCGAAAAGCTGC

CAAGTTGAAAATGGACGAGTAATCGCCTGCTTTGATTCATTGAAAGGCCGTTG

-continued
```
CTCCAGGGAGAACTGCAAATATCTTCATCCACCCCCACATTTAAAAACGCAGTT

GGAGATAAATGGACGCAATAACTTGATTCAGCAGAAGAACATGGCCATGTTGG

CCCAGCAAATGCAACTAGCCAATGCCATGATGCCTGGTGCCCCATTACAACCCGTG

CCAATGTTTTCAGTTGCACCAAGCTTAGCCACCAATGCATCAGCAGCCGCCTTTAAT

CCCTATCTGGGACCTGTTTCTCCAAGCCTGGTCCCGGCAGAGATCTTGCCGACTGCA

CCAATGTTGGTTACAGGGAATCCGGGTGTCCCTGTACCTGCAGCTGCTGCAGCTGCT

GCACAGAAATTAATGAGAAGTAGAAATCGTGGCCCACCTCCCTCTTGGGGTCGTCGCC

CTCGAGATGATTATCGTAGGAGGAGTCCTCCACCTCGTCGCAGATCTCCAAGAAGGAGAA

GCTTCTCTCGCAGCCGGAGCAGGTCCCTTTCTAGAGATAGGAGAAGAGAGAGATCGCTG

TCTCGGGAGAGAAATCACAAGCCGTCCCGATCCTTCTCTAGGTCTCGTAGTCGATCTAGG

TCAAATGAAAGGAAATGA
```
Where:
HATag
MBNL1 ZF1-2
<u>Linker Region (from region between MBNL1 ZF1-2 and ZF3-4)</u>
*SRSF3 RS Domain*

An Example of an Amino Acid Sequence of MBNL1-RS Fusion:

(SEQ ID NO: 92)
ME*YPYDVPDY*MAVSVTPIRDTKWLTLEVCREFQRGTCSRPDTECKFAHPSKSCQVEN

GRVIACFDSLKGRCSRENCKYLHPPPHLKTQLEINGRNNLIQQKNMAMLAQQMQLANA

MMPGAPLQPVPMFSVAPSLATNASAAAFNPYLGPVSPSLVPAEILPTAPMLVTGNP

GVPVPAAAAAAAQKLMRSRNRGPPPSWGRRPRDDYRRRSPPPRRRSPRRRSFSRSRSR

SLSRDRRRERSLSRERNHKPSRSFSRSRSRSRSNERK
where:
*HA Tag*
MBNL1ZF1-2
Linker Region (from region between MBNL1 ZF1-2 and ZF3-4)
SRSF3 RS Domain

In some embodiments, a synthetic MBNL1 protein is fused to a targeting moiety that aids in penetrating cells. In some embodiments, a targeting moiety is a cell penetrating peptide, a cell surface receptor binding ligand, a cell penetrating antibody or a cell-penetrating antibody fragment.

A cell penetrating peptide (CPP) is a short peptide that facilitates cellular intake or uptake of a molecule to which it is fused. In some embodiments, a CPP is hydrophilic, amphiphilic or of periodic sequence type. Examples of hydrophilic CPPs are TAT, SynB 1, SynB3, PTD-4, PTD-5, FHV Coat-(35-49), BMV Gag-(7-25), and D-Tat. Examples of amphiphilic CPPs are transportan, MAP, SBP, MPG, Pep-1, and Pep-2. Examples of CPPs of the periodic sequence type are polyarginines (RxN, 4<N<17), polylysines (KxN, 4<N<17), R10 and R7. CPPs are described in McCarthy et al. (WO2014087023 A1) and Stewart et al. (Org. Biomol. Chem., 2008, 6:2242) and are herein incorporated by reference in their entirety. CPPs are also described in CPPsite (http://crdd.osdd.net/raghava/cppsite/), a CPP database (Gautum et al., Database, Vol. 2012, Article ID bas015), and are herein incorporated by reference in their entirety.

A cell penetrating antibody is an antibody that facilitates cellular intake or uptake of a molecule to which it is fused or linked. In some embodiments, a cell penetrating antibody is 3E10 murine anti-DNA autoantibody, or functional mutants or functional fragments thereof. In some embodiments, a targeting moiety is an Fv fragment of 3E10 murine anti-DNA autoantibody. The mAb 3E10 and functional mutants and functional fragments thereof are described in Weisbart (CA 2248233 A1), and are herein incorporated by reference in their entirety. In some embodiments, a targeting moiety is a Fab or F(ab')2 fragment.

In some embodiments, a targeting moiety is fused to a synthetic MBNL1 protein via covalent or non-covalent interactions.

In some embodiments, a synthetic MBNL1 protein fused to a targeting moiety is taken up by a cell through endocytosis. In some embodiments, a synthetic MBNL1 protein fused to a targeting moiety is taken up by a cell directly. In some embodiments, a synthetic MBNL1 protein fused to a targeting moiety is taken up by a cell by translocation through the formation of a transitory structure. In some embodiments, a synthetic MBNL1 protein that is not fused to a targeting moiety is taken up by a cell either directly, via endocytosis or by translocation through the formation of a transitory structure.

In some embodiments, a composition comprising a synthetic MBNL1 protein comprises a pharmaceutically acceptable carrier. The term "carrier" refers to a diluent, adjuvant, excipient, or vehicle with which the synthetic MBNL1 protein is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of synthetic proteins to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

In some embodiments, synthetic MBNL proteins provided herein can be recombinant proteins synthesized using recombinant techniques known in the art. In some embodiments, synthetic MBNL proteins provided herein can be synthesized using chemical synthesis techniques known in the art. In some embodiments, a plasmid or other nucleic acid vector encoding one or more synthetic MBNL proteins is provided. In some embodiments, recombinant host cells are provided comprising one or more plasmids or other vectors that encode one or more synthetic MBNL proteins. In some embodiments, viral particles (e.g., adeno-associated virus particles) are provided comprising one or more nucleic acids encoding one or more synthetic MBNL proteins. Direct delivery of any one of the synthetic MBNL proteins is also contemplated herein. For example a synthetic MBNL protein can be conjugated to or can comprise a cell penetrating peptide (CPP), a cell surface receptor binding ligand, a cell penetrating antibody, a mutant cell penetrating antibody, and a cell-penetrating antibody fragment such as an Fv antibody fragment (e.g., an Fv fragment of 3E10 murine anti-DNA autoantibody).

In some aspects, provided herein are methods of treating a subject (e.g., a human subject) having a repeat expansion disease, the method comprising administering to the subject a composition comprising or encoding one or more synthetic MBNL proteins provided herein.

Repeat expansion diseases are also referred to as trinucleotide repeat disorders, trinucleotide repeat expansion disorders, triplet repeat expansion disorders or codon reiteration disorders. Herein, repeat expansion diseases are also referred to as polynucleotide disorders or polynucleotide repeat expansion disorders/diseases. Repeat expansion diseases are caused by a mutation where microsatellite polynucleotide repeats in certain genes exceed the normal threshold. Such mutations occur throughout the genome of subjects with such disease.

One of the features of repeat expansion disease is the sequestration of MBNL proteins (including MBNL1) by toxic RNA products of polynucleotide repeats, which results in diminished levels of functional MBNL1. This can affect regulation of alternative splicing, and other functions of MBNL1 such as regulation of RNA localization and RNA metabolism. The compositions provided herein that comprise synthetic MBNL1 protein can be used to reverse one or more of these functional deficiencies of MBNL1 that lead to disease symptoms. In some embodiments, administration of synthetic MBNL1 can lead to splicing by synthetic MBNL1. In some embodiments, administration of synthetic MBNL1 can lead to freeing of endogenous MBNL1 from toxic RNA of repeat expansions so that the freed endogenous MBNL1 can then perform a splicing function. In some embodiments, administration of synthetic MBNL1 can lead to splicing by synthetic MBNL1, and freeing of endogenous MBNL1 from toxic RNA of repeat expansions so that the freed endogenous MBNL1 can then perform a splicing function.

A repeat expansion disease can be one that is caused by repeats in non-coding sequences. An example of such a disease is myotonic muscular disease. Affected subjects with myotonic dystrophy type 1 (DM1) contain a CTG repeat expansion of the 3' UTR of the dystrophia myotonica protein kinase (DMPK) gene and those with myotonic dystrophy type 2 (DM2) have a CCTG repeat expansion in intron 1 of the CCHC-type zinc finger nucleic acid binding protein (CNBP) gene. Other examples of repeat expansion diseases of repeat expansion in non-coding regions are Fragile X syndrome (FRAXA), Friedreich ataxia (FRDA), Spinocerebellar ataxia type 8 (SCA8) and SCA12. Examples of repeat sequences of repeat expansion diseases that are caused by repeats in non-coding sequences are CGG, GCC, GAA, CTG and CAG.

In some embodiments, a repeat expansion disease is one that is caused by exonic $(CAG)_n$ repeats that code for polyglutamine tracts. Examples of repeat expansion diseases that are caused by exonic $(CAG)_n$ repeats are spinobulbar muscular atrophy (otherwise known as Kennedy disease), Huntington's disease, spinocerebellar ataxia (SCA) types 1-3, 6 and 7. For example Huntington's disease is caused by CAG repeats in the HD gene. Another example of a disease caused by RNA toxicity of non-coding repeats is Fuchs Endothelial corneal dystrophy (FECD), in which expansion of intronic $(CTG-CAG)_n$ repeats in transcription factor 4 (TCF4) is found in most Fuchs endothelial corneal dystrophy (FECD) patients. In some embodiments, a repeat expansion disease is amyotrophic lateral sclerosis (ALS).

Repeat expansion diseases are reviewed in Spada and Taylor (Nature Reviews Genetics, 2010, 11: 247) and Cummings and Zoghbi (Hum Mol Genet., 2000; 909) and are herein incorporated by reference in their entirety.

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans.

In some embodiments, the subject is a human subject. Other examples of subjects include domesticated animals such as dogs and cats; livestock such as horses, cattle, pigs, sheep, goats, and chickens; and other animals such as mice, rats, guinea pigs, and hamsters.

In some embodiments, "administering" or "administration" means providing a material to a subject in a manner that is pharmacologically useful. In some embodiments, a composition comprising synthetic MBNL protein is administered to a subject systemically or to a diseased tissue. In some embodiments, a composition comprising a nucleic acid encoding a synthetic MBNL protein is administered to a subject systemically or to a diseased tissue. A composition can be administered subcutaneously, intraocularly, intravitreally, subretinally, parenterally, intravenously (IV), intracerebro-ventricularly, intramuscularly, intrathecally (IT), intracisternally, orally, intraperitoneally, topically, by oral or nasal inhalation, or by direct injection to one or more cells, tissues, or organs by direct injection.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. A desired result may be the reduction of disease symptoms. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

It is to be understood that the fundamentals used in making the compositions of synthetic MBNL1 protein provided herein, and the provided methods of using synthetic MBNL1 to treat subjects with repeat expansion disease can be applied to different isoforms of MBNL1 and also to MBNL2 and MBNL3. In some embodiments, a composition of synthetic MBNL protein can comprise only MBNL1, only MBNL2 or only MBNL3. In some embodiments a composition of synthetic MBNL protein can comprise a mixture of any of the synthetic proteins: MBNL1, MBNL2 and MBNL3. In some embodiments, a composition used to treat a subject with a repeat expansion disease can comprise a chimeric MBNL protein that comprises domains or sequences of MBNL1 and MBNL2, or MBNL1 and MBNL3, or MBNL2 and MBNL3, or MBNL1, MBNL2 and MBNL3. For example, a chimeric synthetic MBNL1 protein may comprise a ZF domain of sequence represented by WT MBNL1, a second ZF domain of sequence represented by WT MBNL2 and a linker of sequence represented by WT MBNL3. In other embodiments, other combinations of one or more domains from different MBNL proteins can be used.

EXAMPLES

Example 1: Engineering and Testing Synthetic MBNL1 Proteins

Described below are synthetic MBNL1 proteins that were engineered to be shorter than the full-length WT MBNL1 protein for better solubility, but have the same or higher splicing activity and/or RNA binding property as full-length WT MBNL1.

Three synthetic MBNL1 constructs were designed and created including 1) an MBNL in which the C-term is truncated and replaced with a NLS signal, 2) an MBNL1 in which the ZF3-4 domain is replaced with a ZF(1-2) to create a MBNL1(1-2,1-2) and in which the C-term is truncated and replaced with a NLS signal, and 3) a double MBNL1(3-4, 3-4) in which the ZF1-2 domain is replaced with a ZF3-4 domain and in which the C-term is truncated and replaced with a NLS signal (FIG. 2A). To create these synthetic MBNL1 proteins, the sequence of each construct was designed and sent to Genscript for production. The C-terminal region of MBNL1 is disordered, which renders the protein challenging to purify in vitro. It was found that the WT-MBNL1 shown in FIG. 2A and FIG. 2B with the NLS that replaces the C-terminus has the same activity as the full length WT MBNL1 in both HeLa and HEK293 cell lines. All synthetic proteins contain an N-terminal HA tag for use in western blot and immunofluorescence assays (FIG. 2B).

Expression Levels of Synthetic MBNL Proteins

Figure 2E:
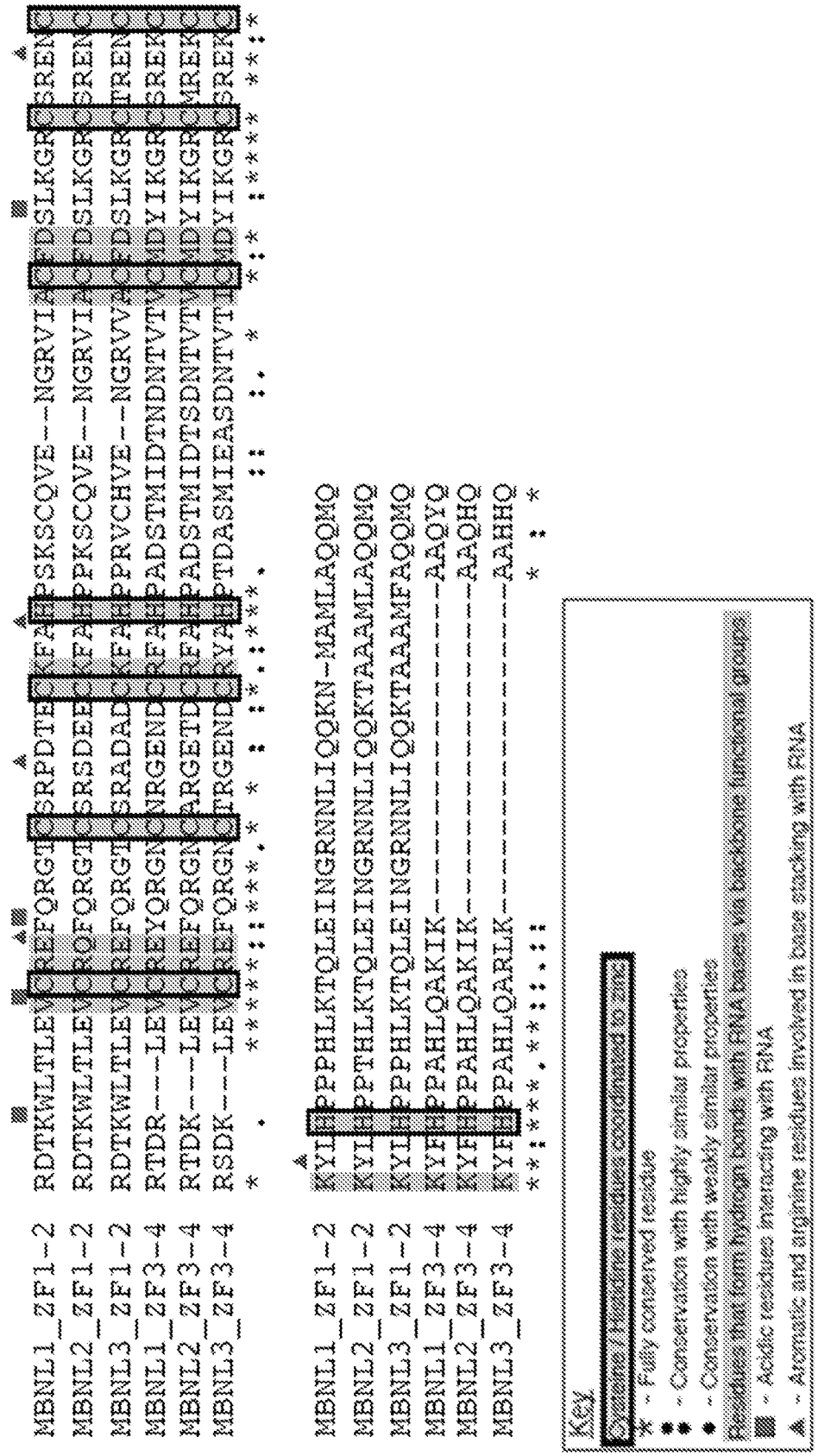
Figure 2F:
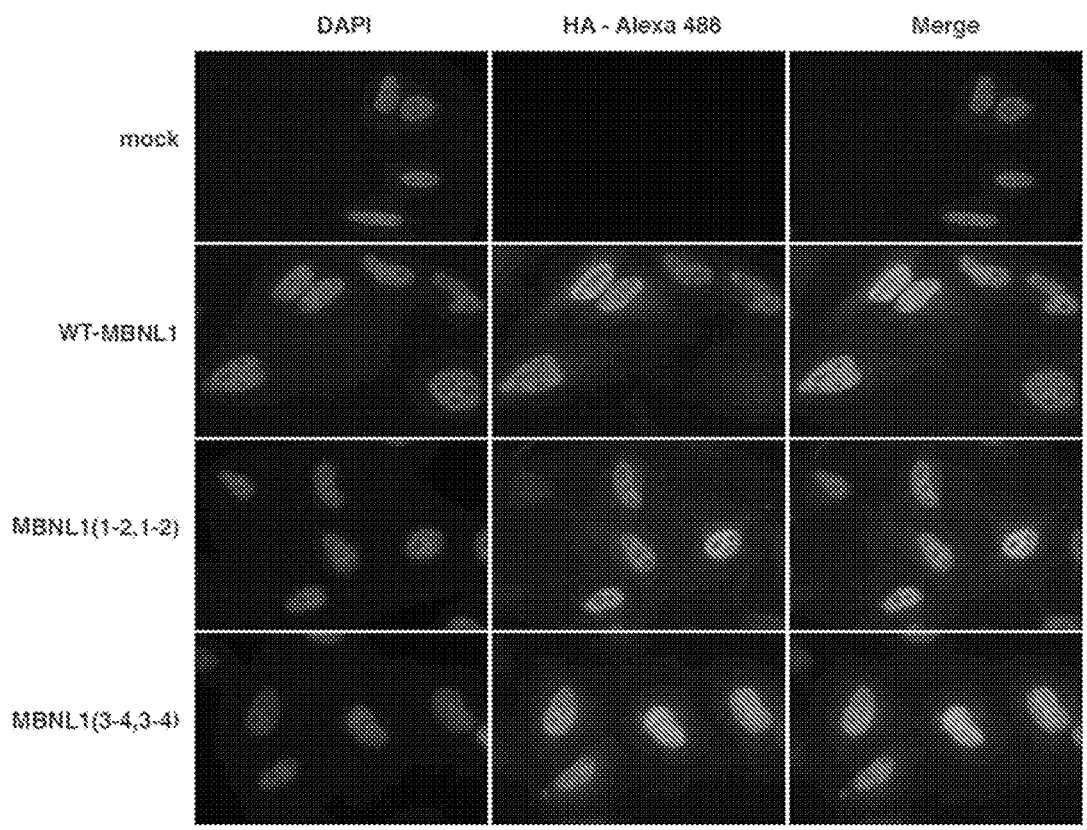

Prior to functional characterization of the synthetic MBNL1 proteins, the relative protein expression levels and subcellular localization were evaluated. Immunofluorescence detection in transfected HeLa cells showed predominant nuclear localization with a modest signal in the cytoplasm for WT-MBNL1 and both synthetic proteins (FIG. 2F). This distribution is comparable to past results, including those using full-length MBNL1 (30, 37). The only noticeable difference in the subcellular distribution of the synthetic proteins was a lack of nucleolar definition in cells expressing MBNL1(3-4,3-4). However, significant differences in steady state protein levels in transfected HeLa cells as determined by immunoblot were detected (FIG. 3E). When normalized to WT-MBNL1, MBNL1(1-2,1-2) is expressed at an approximately 0.5-fold lower level while MBNL1(3-4,3-4) is expressed at a 2.5-fold higher level (FIG. 3E). This pattern of expression was maintained in HEK-293 cells (FIG. 2H).

Figure 2G:
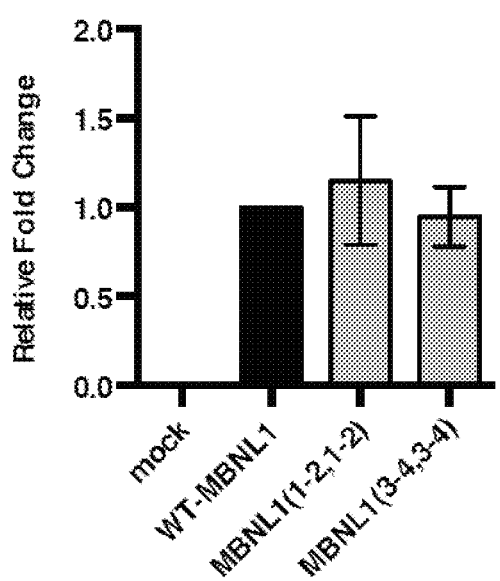
Figure 2H:
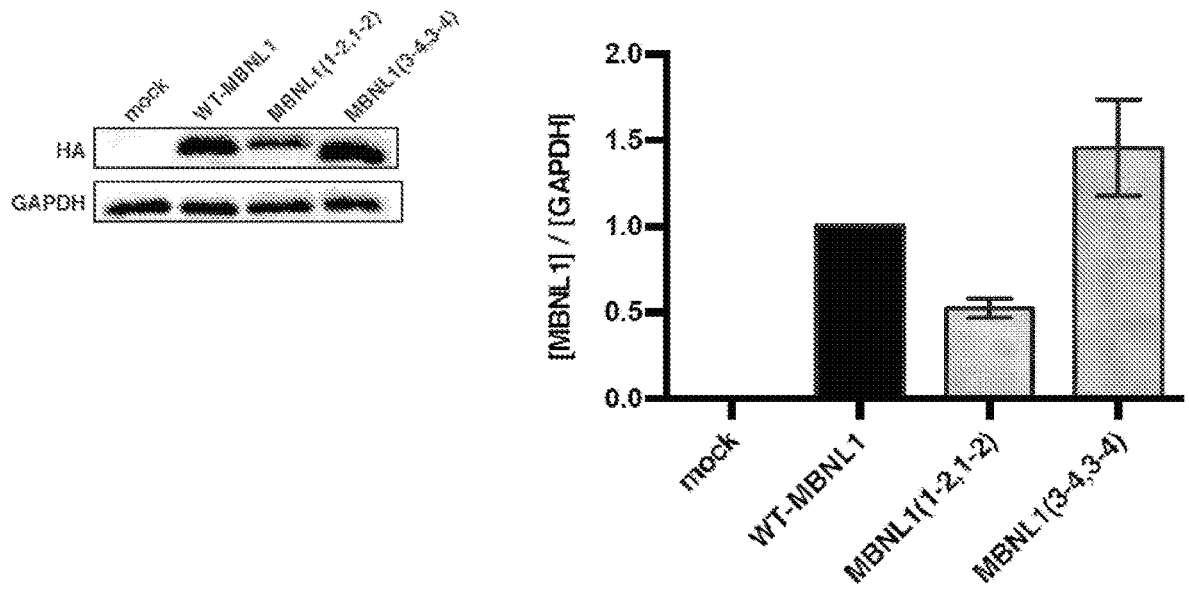

These variations in protein levels were not due to changes in mRNA expression as assayed by RT-qPCR (FIG. 2G). Overall, these data suggest that the ZF3-4 domain confers additional stability to MBNL1 compared to ZF1-2.

MBNL1(1-2,1-2) has Splicing Activity Equal to or Greater than WT-MBNL1

To explore how variation of ZF content within the synthetic proteins would impact MBNL1 splicing activity, a cell-based splicing assay was used to test the splicing activity of WT-MBNL1, MBNL1(1-2,1-2) and MBNL1(3-4,3-4).

Both HeLa and HEK-293 cells were cotransfected with a MBNL1 construct and a minigene reporter. HeLa and HEK-293 cells have low levels of MBNL protein expression so the endogenous gene has only a minimal impact on MBNL regulated events. The minigenes are minimal splicing reporters containing an alternatively spliced exon flanked by two neighboring introns and adjoining exons from MBNL1 regulated events. Description of the minigenes used in the experiment can be found in Purcell et al. (Molecular and Cellular Biology, 2012, 32: 4155-4167). The assay was used with a series of splicing reporter minigenes, many of which are derived from events known to be mis-regulated in DM. These reporters include (i) human insulin receptor exon 11 (INSR. (ii) human cardiac troponin T type 2 exon 5 (TNNT2) (34, 41), (iii) human sarcoplasmic/endoplasmic reticulum $Ca^{2+}$-ATPase 1 exon 22 (ATP2A1) (31, 45), (iv) mouse nuclear factor I/X exon 8 (Nfix) (16), (v) mouse very-low-density lipoprotein receptor exon 16 (Vldlr) (16), and (vi) human MBNL1 exon 5 (46). Following transfection, RNA isolation and RT-PCR was performed to measure the ratio of alternative exon inclusion, or percent spliced in (PSI). Inclusion levels of each alternative exon were then quantified via RT-PCR and expressed as percent spliced in (PSI, ψ) (e.g., percent exon inclusion). Splicing activity of MBNL1(1-2,1-2) and MBNL1(3-4,3-4) were then determined as a percentage of activity relative to WT-MBNL1 for each minigene event. As a control for endogenous MBNL1 splicing, a transfection of minigene and empty plasmid (mock) was performed for each of the events studied.

Figure 3A:
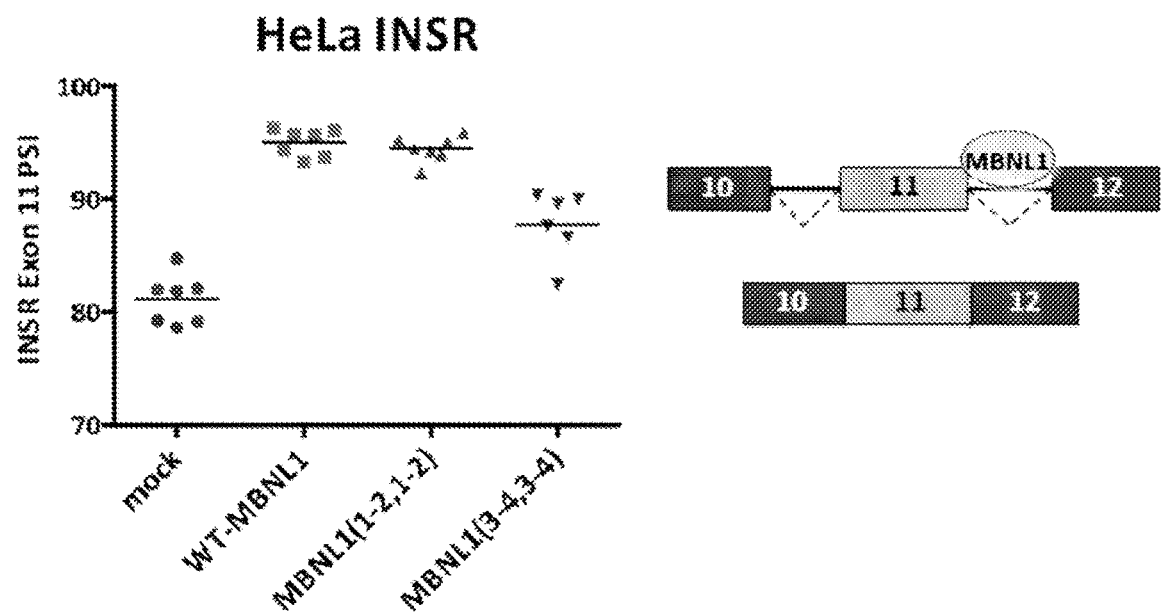
FIG. 3A-FIG. 3G show the splicing activity of synthetic MBNL1proteins.
Figure 3B:
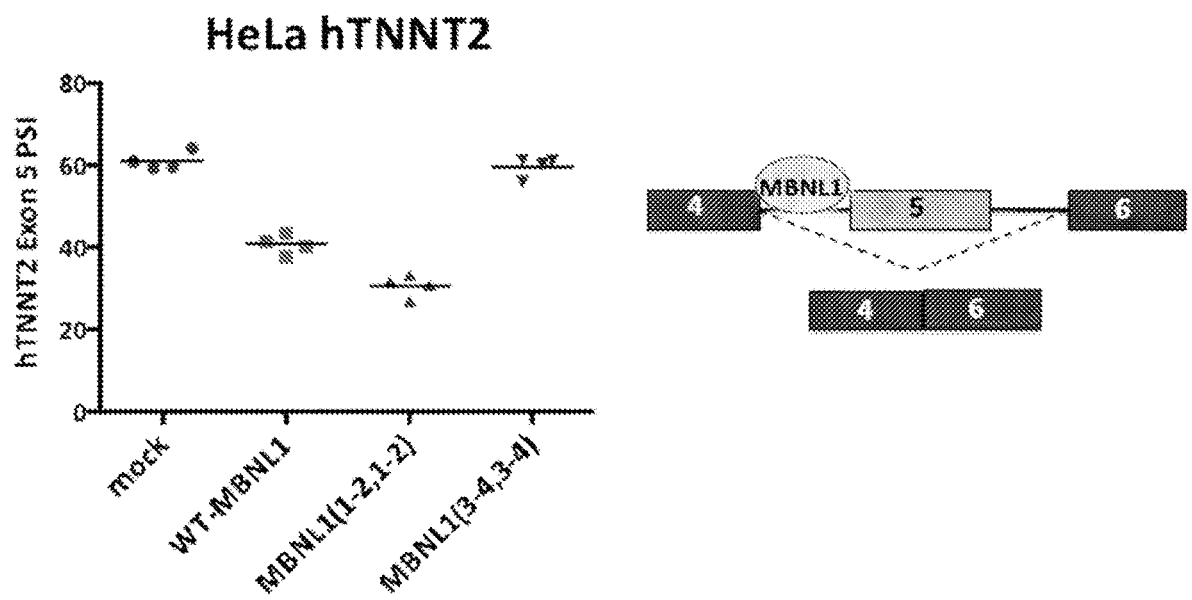

In both cell types, MBNL1(1-2,1-2) retained splicing activity equivalent to WT-MBNL1 for several splicing events (FIG. 3A and FIG. 3B). For the TNNT2 event, MBNL1(1-2,1-2) had greater splicing activity than WT-MBNL1 (FIG. 3B). As predicted, MBNL1(3-4,3-4) retained modest or minimal splicing activity for the tested minigenes (FIG. 3A and FIG. 3B).

Figure 3C:
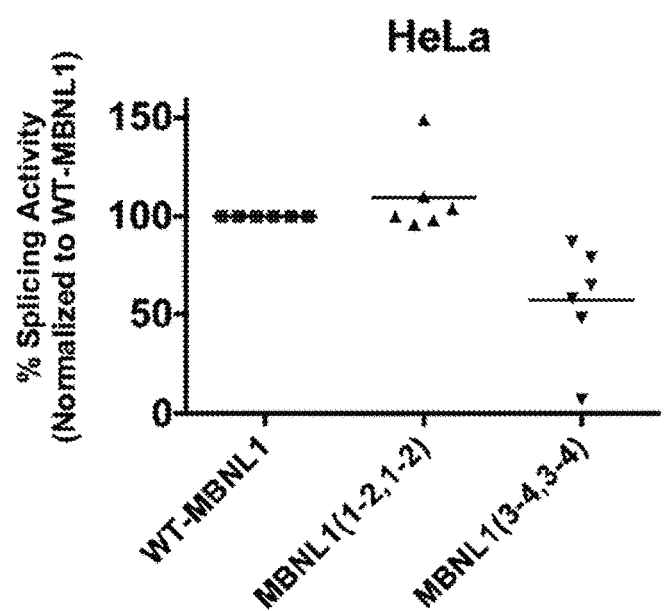
Figure 3D:
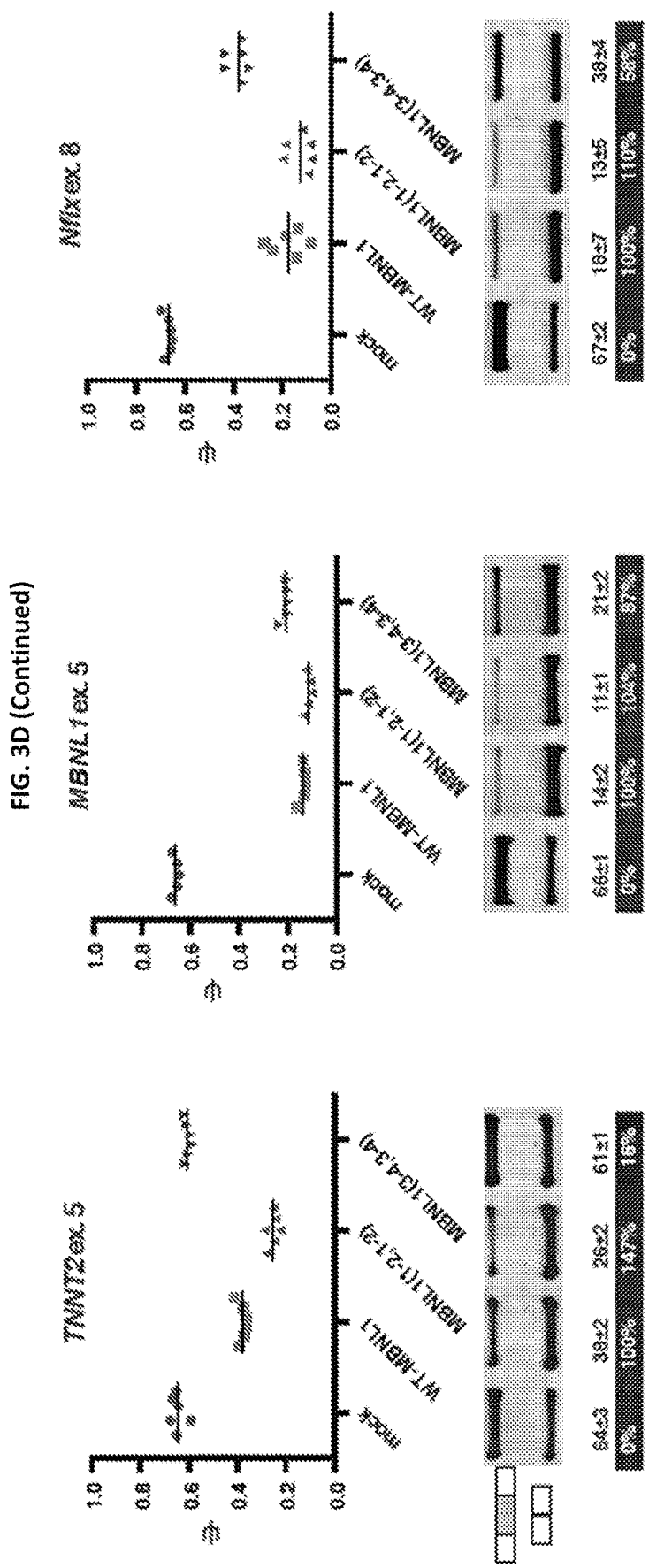
Figure 3E:
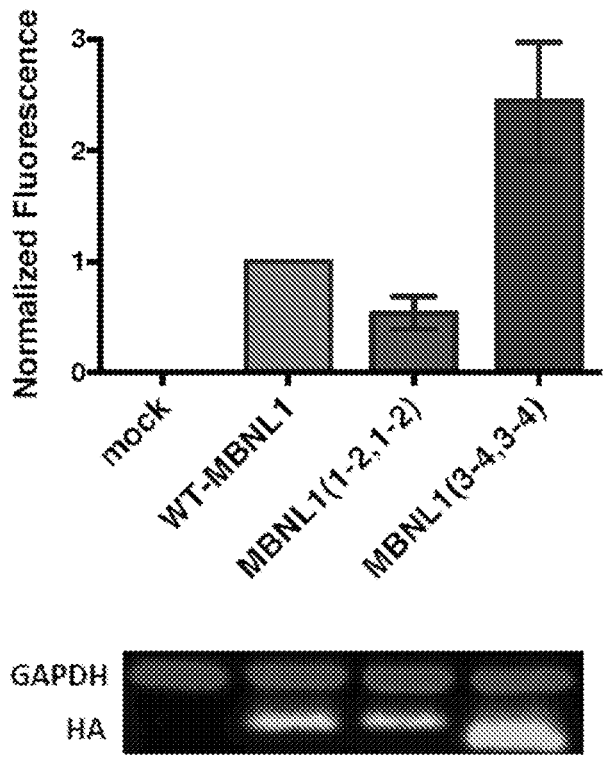

Similar data was observed for other minigenes tested (FIG. 3C and FIG. 3D).

The data for the six minigenes tested revealed that MBNL1(1-2,1-2) regulated splicing at a level equivalent to or better than WT-MBNL1. MBNL1(3-4,3-4), while still functional, had significantly reduced splicing activity (FIG. 3D). These patterns of splicing regulation were maintained for both inclusion (INSR, ATP2A1, and Vldlr) and exclusion (TNNT2, MBNL1, and Nfix) events, indicating that the splicing activity of these synthetic proteins is independent of RNA target and regulation type. Overall, these observations are consistent with the hypothesis that the splicing activity of MBNL1(1-2,1-2) would be high while that of MBNL1 (3-4,3-4) would be low. Importantly, disruption of the canonical ZF domain organization and removal/replacement of specific ZF domains did not render the synthetic MBNL1 proteins dysfunctional, indicating that (i) MBNL1 is amenable to sequence alterations and substitutions, and (ii) the activity of the individual ZF domains can be uncoupled.

Figure 3F:
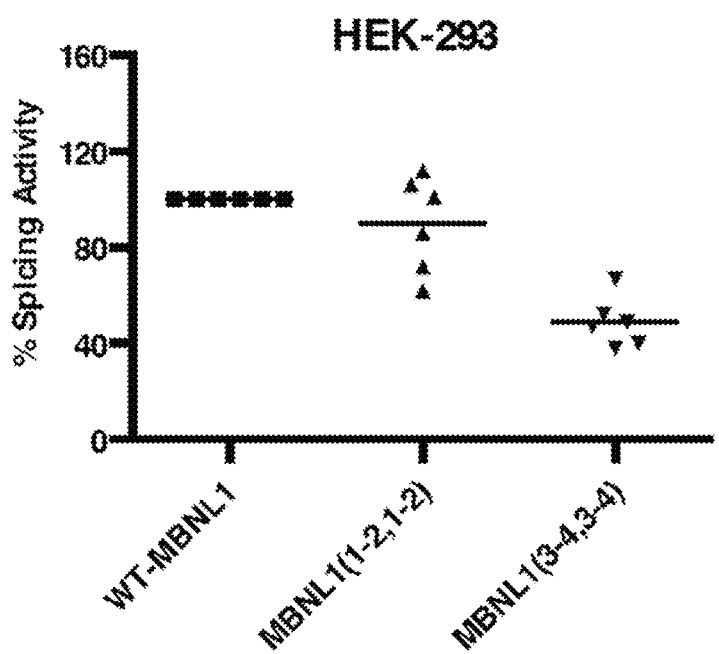
Figure 3G:
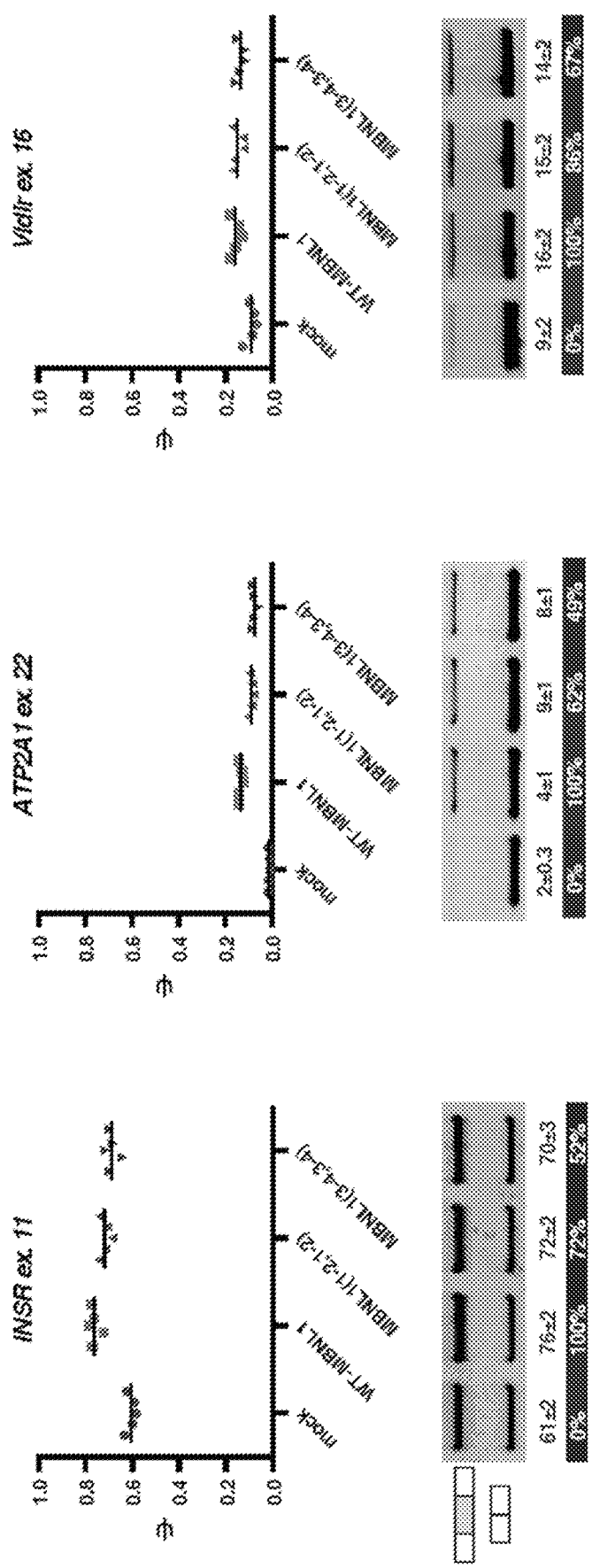
Figure 3G:
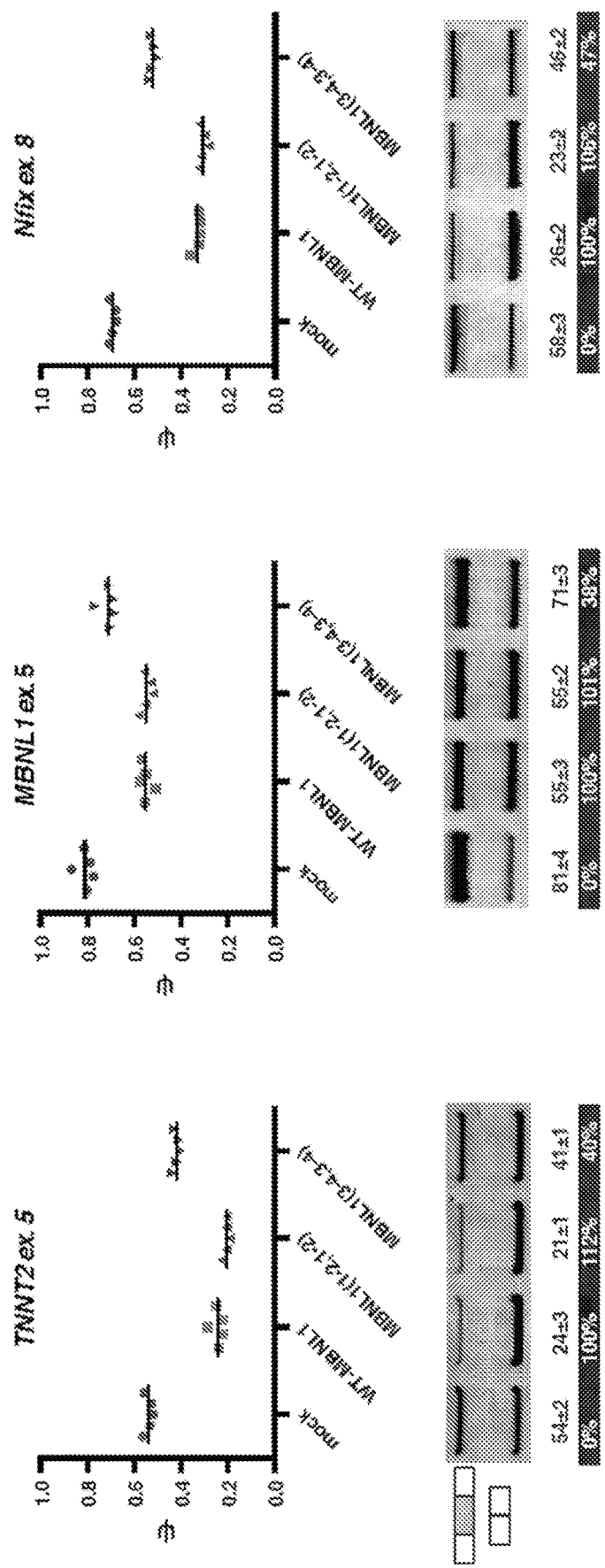

The only reporter that showed large differences in regulation was TNNT2. Within the context of this event, MBNL1 (1-2,1-2) displayed enhanced activity (147%) while MBNL1 (3-4,3-4) was only minimally able to regulate splicing (16% activity) (FIG. 3D). In contrast, all three proteins were able to regulate splicing of the MBNL1 reporter with similar activity (FIG. 3D). For all other reporters utilized, MBNL1 (1-2,1-2) regulated splicing at equivalent levels to WT-MBNL1 while MBNL1(3-4,3-4) retained approximately 50% of WT-MBNL1 splicing activity (FIG. 3C). These trends were maintained in HEK-293 cells despite changes in $\Delta\psi$ for each minigene between the two different cell types (FIG. 3F and FIG. 3G).

An important point regarding these results is that equal amounts of plasmid were transfected into cells and this resulted in differences in the amount of each MBNL1 protein expressed (FIG. 3E for HeLa and FIG. 2G for HEK-293). Interestingly, the high levels of MBNL1(3-4,3-4) were not sufficient to regulate splicing as well as WT-MBNL1. In contrast, MBNL1(1-2,1-2) maintained comparable splicing regulation to WT-MBNL1 with half the amount of protein present. Despite the lower expression level of MBNL1(1-2,1-2), it regulated splicing as well if not better than WT-MBNL1 at a lower concentration depending on the splicing event being assayed. In contrast, MBNL1(3-4,3-4) was unable to regulate splicing to the same degree as the other proteins even at its high level of expression.

Figure 6:
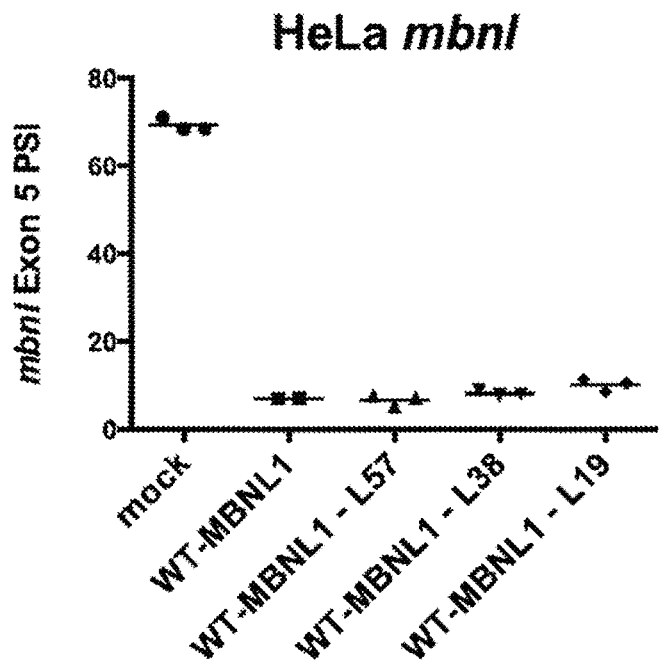
FIG. 6 shows splicing of an mbnl minigene by WT-MBNL1, and WT-MBNL1 synthetic proteins with truncated linker sequences.

It was found that synthetic MBNL1 proteins with truncated linker sequences are just as effective at splicing compared to MBNL1 protein with full-length linker of 76 amino acids. FIG. 6 shows that synthetic WT-MBNL1 proteins with a linker of only 57, 38 or 10 amino acids were able to splice exon 5 of mbnl (auto-regulated splicing event and is shown in lower case to differentiate between protein and pre-mRNA substrate) with the same activity as synthetic WT-MBNL protein with a length of linker (e.g., 76 amino acids) that corresponds to that of endogenous WT MBNL1.

Figure 5:
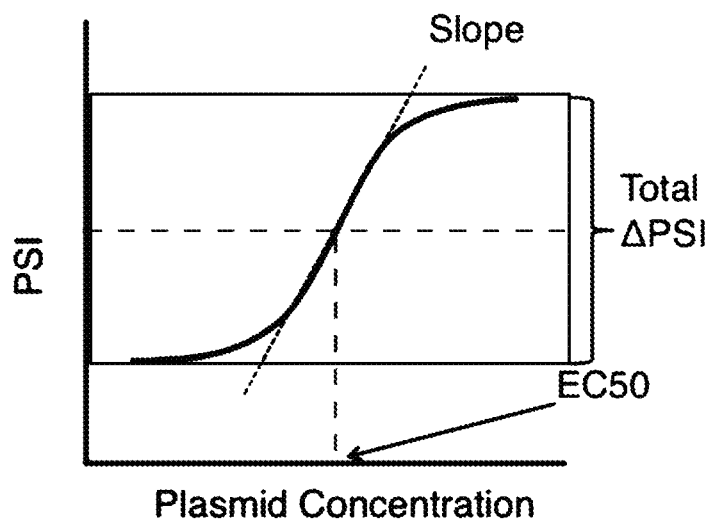
FIG. 5 shows an example of dose response curve and representation of quantitative parameters than can be derived for splicing activity of synthetic MBNL1 proteins as a function of protein concentration, or concentration of plasmid used to express the synthetic MBNL1 proteins.

Controlled Dosing of Synthetic MBNL1 Proteins Reveals Significantly Different Efficacies for Splicing Regulation To evaluate the splicing activity of these proteins at multiple concentrations, a splicing assay can be performed across a gradient of protein expression. This gradient can be created by transfecting HeLa and HEK-293 cells with increasing amounts of plasmid comprising nucleic acid encoding a MBNL1 protein. Cells can also be transfected with minigene reporters. RNA can then be collected and processed via RT-PCR to determine the PSI at each protein concentration. Additionally, western blots can be performed and protein levels at each plasmid concentration can be determined. Using this data, PSI ($\psi$) vs. plasmid concentration (proxy for protein concentration) "dose response" curves for both synthetic proteins as well as WT-MBNL1 can be plotted (FIG. 5). Quantitative parameters can then be derived that describe the splicing regulation of each event by each individual protein. These parameters include slope, total APSI, and $EC_{50}$. The slope of the response curve provides a relative measure of how cooperative that splicing event is compared to other events while the $EC_{50}$ is the concentration of plasmid required to regulate splicing at 50% of maximal activity. This assay can be performed for several minigenes, including TNNT2, the mbnl auto-regulation event, and ATP2A1. These events are interesting because both WT-MBNL1 and MBNL1(1-2,1-2) have similar maximal PSIs for the mbnl and ATP2A1 events within the overexpression splicing assays. In contrast, TNNT2 can be used because all three proteins showed different maximal PSIs (FIG. 3B) for hTNNT2 minigene. It would be expected that MBNL1(1-2,1-2) regulates splicing for each of these events at lower concentrations (lower $EC_{50}$ values). Another possibility is that the slope for the MBNL1(1-2,1-2) splicing curve may be steeper for the MBNL(1-2,1-2) compared to the WT-MBNL1 indicating a greater level of cooperativity for MBNL1(1-2,1-2) compared to the other proteins.

Figure 7:
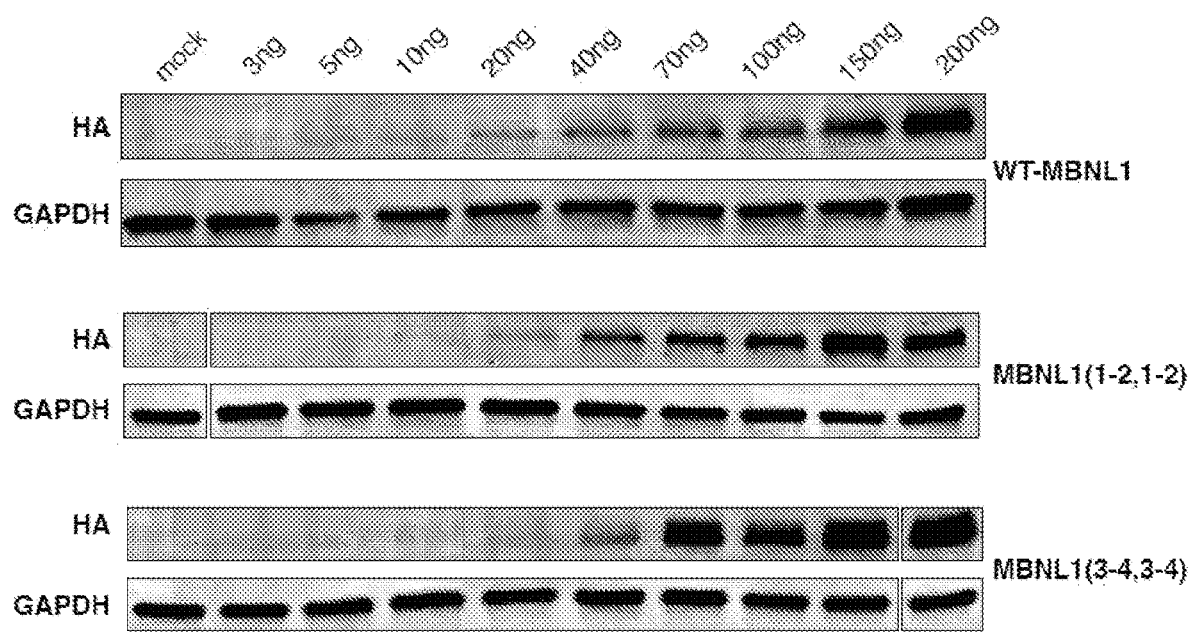
FIG. 7 shows representative western blots used to create dose-response curves in plasmid dosing system. HeLa cells were transfected with increasing concentrations of MBNL1 expression-plasmid and MBNL1 levels detected using an anti-HA antibody. Protein levels at each plasmid dose were normalized to a GAPDH loading control. blot.

In brief, to gain further insight into MBNL1(1-2,1-2) and MBNL1(3-4,3-4) alternative splicing regulation, especially as it relates to protein concentration, the same cell-based splicing assays previously utilized across a gradient of MBNL1 expression were performed. This experimental analysis was necessary since the synthetic proteins had different expression profiles (FIG. 3E). To create the range of protein levels required within this system, HeLa cells were transfected with increasing amounts of protein-expression plasmid for each MBNL1 tested. Western blot analysis against the HA tag was then used to quantify relative MBNL1 levels at each concentration of plasmid transfected (see FIG. 7 for representative blots). As expected, MBNL1 (3-4,3-4) maintained relatively high levels of expression across the gradient while MBNL1(1-2,1-2) protein levels remained lower (FIG. 7).

Figure 8A:
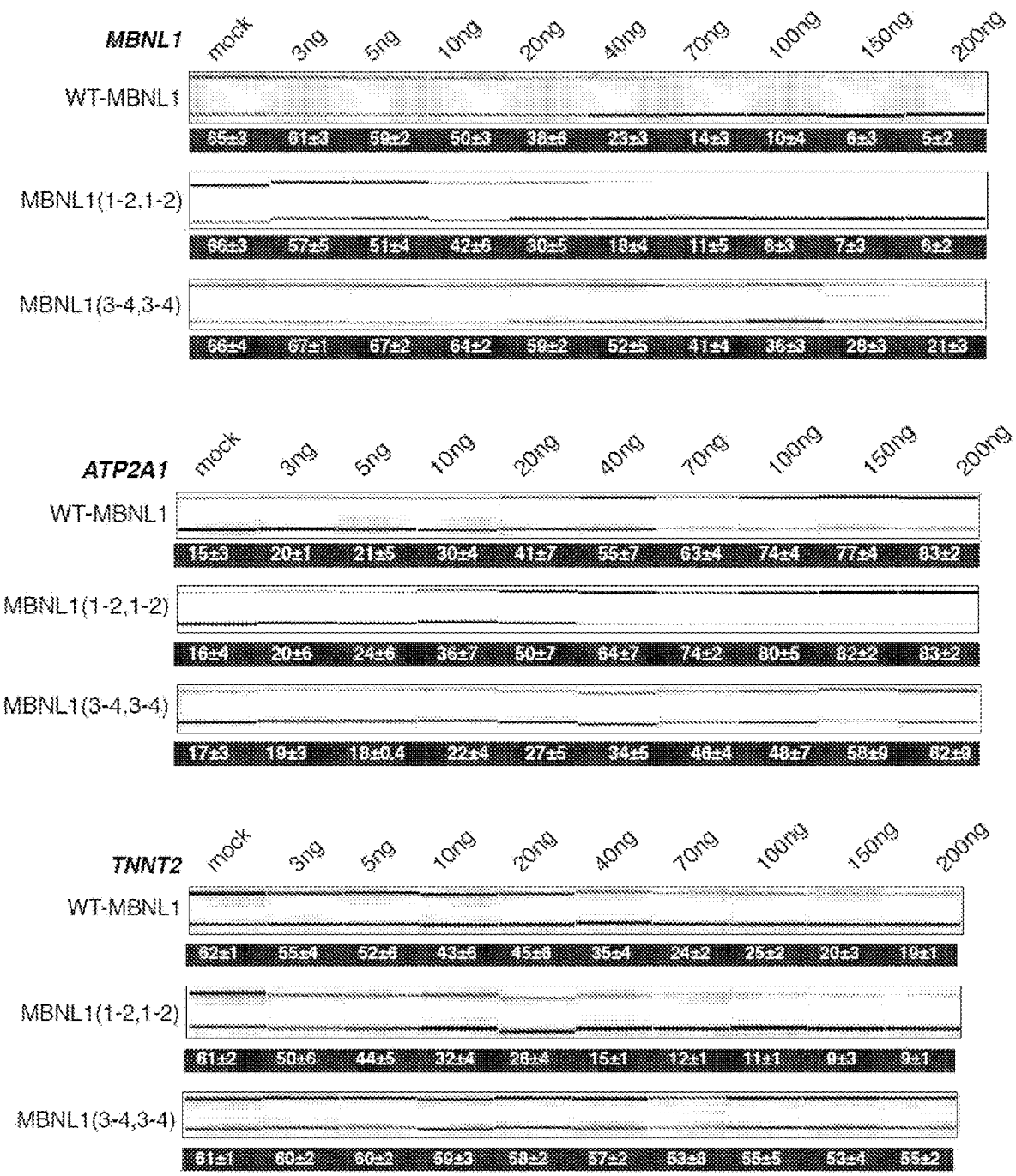
FIG. 8A and FIG. 8B show representative splicing gels used to calculate changes in exon inclusion across the gradient of protein expression produced within the plasmid dosing system.
Figures 8B, 9A:
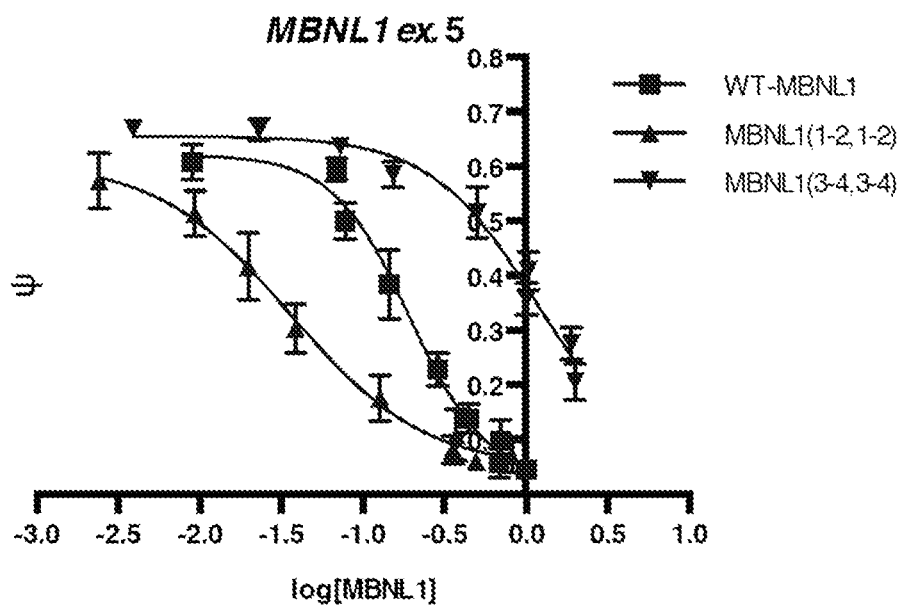
FIG. 9A-FIG. 9D show that synthetic MBNL1 proteins regulate splicing at different relative protein levels compared to WT-MBNL1.

Next, the $\psi$ of three different minigenes (TNNT2, MBNL1, and ATP2A1) for each individual point along the protein gradient was determined (representative images used to calculate $\psi$ can be seen in FIG. 8A). These values were then plotted against log[MBNL1] to create dose-response curves for each protein. FIG. 8B shows quantitative parameters (log($EC_{50}$) and Hill Slope, ±standard error) generated from the dose-response curves. MBNL1 and ATP2A1 were selected from the pool of minigene reporters to test in this system because (i) these two minigenes displayed a robust splicing response (large $\Delta\psi$) in the cell-based splicing assay (FIG. 3D), (ii) they represent both MBNL1-regulated inclusion and exclusion events, respectively, (iii) both minigenes have been well-characterized (31, 46), and (iv) MBNL1(1-2,1-2) and MBNL1(3-4,3-4) both show similar splicing activity and maximal $\psi$ compared to WT-MBNL1 (FIG. 3D). TNNT2 was chosen as an additional reporter to test in this dosing system because it displayed the largest difference in splicing activity for both synthetic MBNL1 proteins (FIG. 3D). Creation of these dose curves allowed for the derivation of several quantitative parameters that describe the splicing regulation of each event, e.g., $EC_{50}$ and slope. The slope of the response curve provides a relative measure of cooperativity while the $EC_{50}$ value provides a relative measure of how much protein is required to obtain splicing regulation at 50% of maximum $\psi$.

Figure 9B:
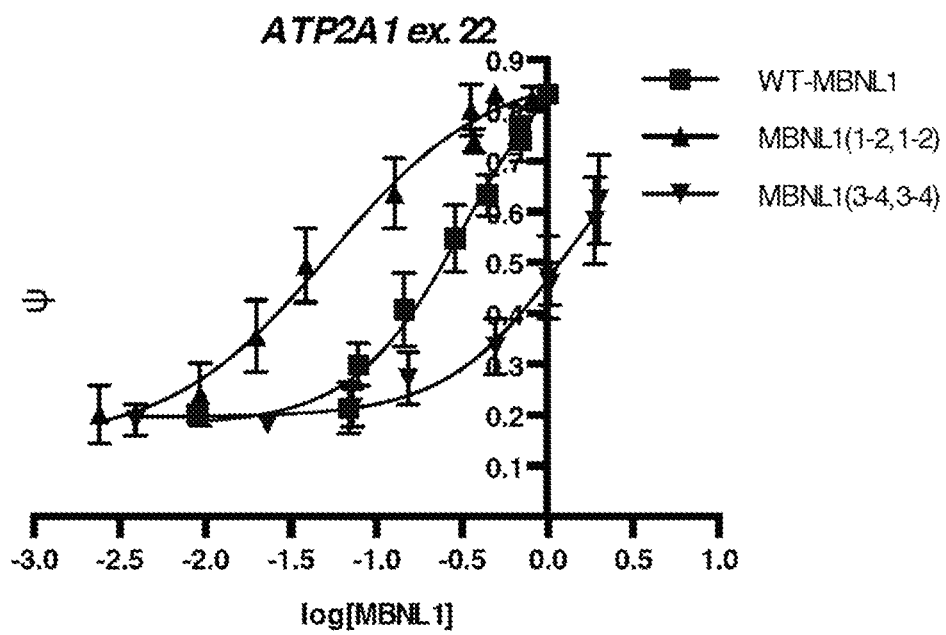
Figure 9C:
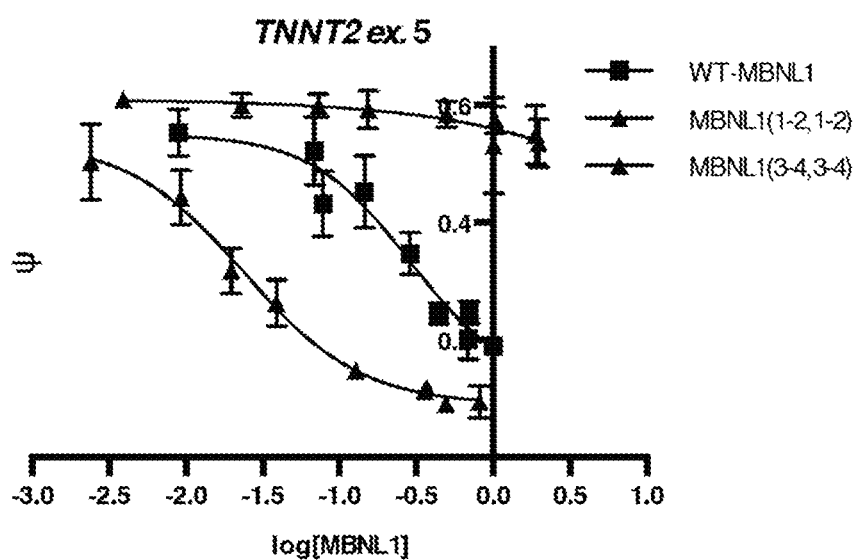
Figures 9D, 10A:
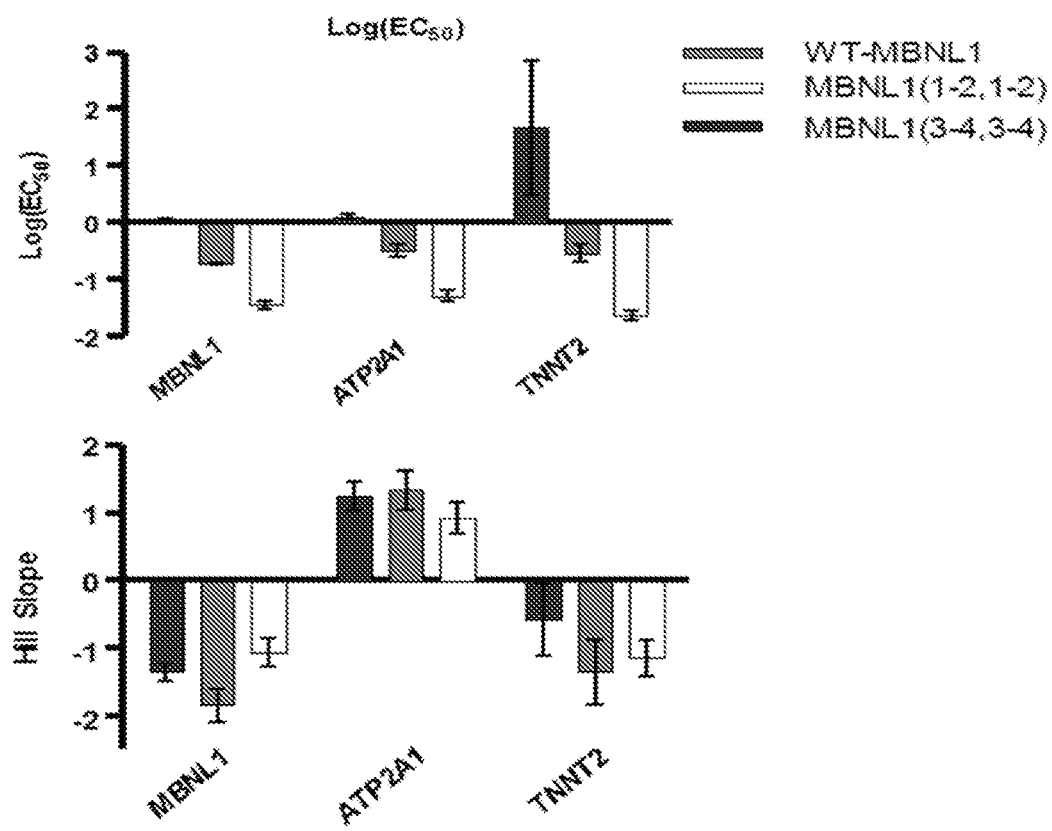
FIG. 10A-FIG. 10E show that reorganization of zinc finger domains does not significantly impact RNA binding of synthetic MBNL1 proteins.

Results from these experiments revealed different dose-response curves for each MBNL1 protein tested and for each minigene assayed (FIG. 9A-FIG. 9C). Both WT-MBNL1 and MBNL1(1-2,1-2) displayed typical dose response curves that show a plateau in $\psi$ for all three minigene events tested (FIG. 9A-FIG. 9C). Based on the $EC_{50}$ values derived, WT-MBNL1 required approximately 5-fold more protein compared to MBNL1(1-2,1-2) to achieve similar levels of splicing regulation (FIG. 9D). For all three events tested the slope of the dose response curves for WT-MBNL1 was steeper compared to MBNL1(1-2,1-2) (FIG. 9D). Interestingly, this indicates that while less MBNL1(1-2,1-2) protein is required to reach the maximum $\psi$, there is an apparent loss in cooperative splicing regulation. In contrast to WT-MBNL1 and MBNL1(1-2,1-2), the dose-response curves for MBNL1(3-4,3-4) revealed that, as expected, high expression levels are required to achieve modest splicing regulation (FIG. 9D). Almost no change in $\psi$ was observed for TNNT2 (FIG. 9C). Even for minigene events assayed in which MBNL1(3-4,3-4) was able to achieve splicing regulation in the overexpression system (ATP2A1 and MBNL1, FIG. 3D), the $EC_{50}$ values are high and the slopes are shallow compared to the other two proteins (FIG. 9C). Overall, the controlled dosing of the synthetic MBNL1 proteins revealed that as predicted, MBNL1(3-4,3-4) has significantly reduced splicing activity while MBNL1(1-2,1-2) should be considered a high activity, synthetic derivative of WT-MBNL1 with a 5-fold increase in splicing activity.

To further investigate the relationship between MBNL1 protein concentration and splicing activity stable inducible cell lines for different synthetic constructs and WT-MBNL1 have been created. It should be appreciated that an alternative approach to assess the role of MBNL1 protein concentration on splicing activity can be taken. For example, stable cell lines can be created that express synthetic MBNL1 in which expression of protein that can be controlled using doxycycline.

MBNL1(1-2,1-2) and MBNL1 (3-4,3-4) have Similar RNA Binding Affinity for $CUG_4$ RNA as WT-MBNL1.

Figure 4A:
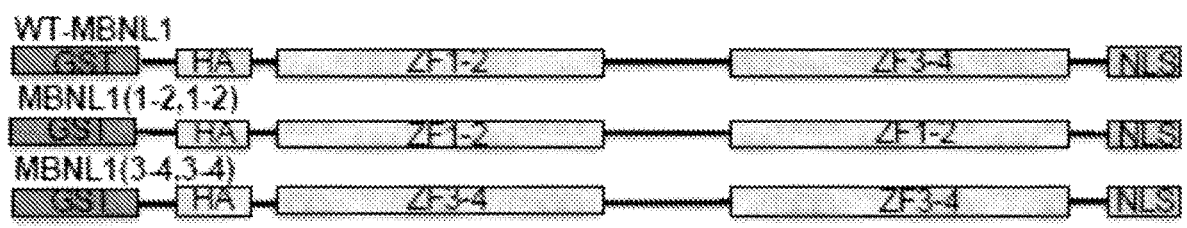
FIGS. 4A and 4B show binding of synthetic MBNL1 proteins to $CUG_4$ RNA. The top panel of FIG. 4A shows a diagram of synthetic WT-MBNL1, MBNL1(1-2,1-2) and MBNL1(3-4,3-4) proteins. All three synthetic MBNL1 proteins are fused to a HA-tag and GST-tag on the N-terminus. The bottom panel of FIG. 4A shows an example of EMSA performed using $CUG_4$ RNA with the synthetic MBNL1 synthetic proteins shown in the top panel. The top panel of FIG. 4B shows the binding isotherms for WT-MBNL1, MBNL1(1-2,1-2) and MBNL1(3-4,3-4) proteins binding to $CUG_4$ RNA. The bottom panel of FIG. 4B shows the binding affinities of the synthetic MBNL1 proteins for binding to $CUG_4$ RNA.
Figure 4A:
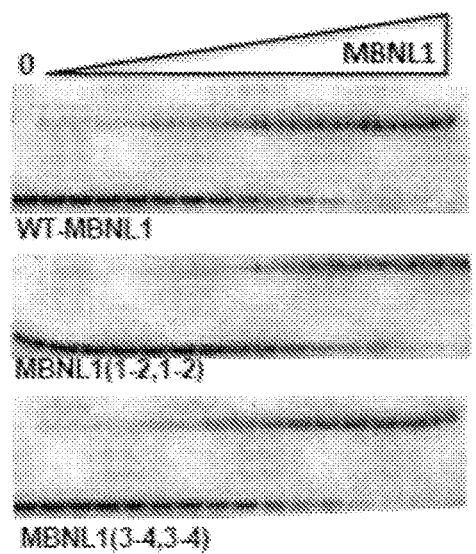
Figure 4B:
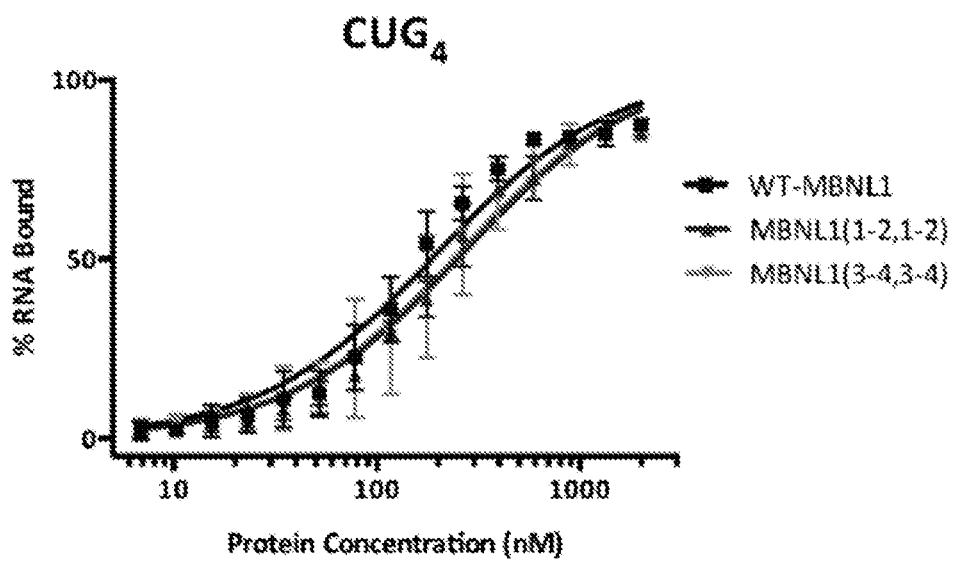

All synthetic MBNL1 proteins were expressed and purified as N-terminal glutathione S-transferase (GST) fusions (FIG. 4A). These proteins were then used in electrophoretic mobility shift assays (EMSAs) with $CUG_4$ RNA substrate. The fraction of radiolabeled RNA bound to the protein was used to determine an apparent KD (dissociation constant). Experiments indicate that all three proteins bind to $CUG_4$ with similar affinity [WT-MBNL1 KD=196 nM, MBNL1 (1-2,1-2) KD=269 nM, MBNL1(3-4,3-4) KD=257 nM] (FIG. 4B).

It should be appreciated that, as an alternative to EMSA, RNA binding activity of synthetic MBNL1 proteins can be assessed using fluorescence polarization assays. In this system RNA substrates can be fluorescently labeled and binding assessed by changes in the anisotropy of the RNA when incubated with MBNL1 protein. In contrast to EMSAs, this assay has the benefit of not needing to separate free and bound RNA species. When engineering synthetic proteins proper folding can be a concern. The robust activity in the splicing assays and EMSAs performed reduces this concern. However, an RNA binding saturation assay can be used to assess the percentage of active purified protein in a given composition.

To evaluate the binding of MBNL1 to CUG repeat RNA within the cellular environment and to further determine how these proteins will behave in vivo, RNA fluorescence in situ hybridization (FISH) combined with protein immunofluorescence (IF) can be utilized. RNA foci can be detected using a Cy3-(CAG)10 probe while synthetic MBNL1 proteins can be detected using an anti-HA antibody. Colocalization of MBNL1 with CUG repeat RNA foci can then be visualized and quantified using confocal microscopy. Plasmids for MBNL1 can be transfected into HeLa cells with a plasmid expressing 960 CTG repeats. Previous studies have shown that MBNL1 strongly co-localizes with the repeat RNA foci formed in such a system. If the synthetic MBNL1 proteins are found to colocalize with repeat foci within this model system, it would mean that synthetic MBNL proteins can release the endogenous sequestered MBNL proteins leading to splicing rescue. It should be appreciated that the synthetic proteins can be transfected into diseased cells (e.g., DM1 patient-derived fibroblast cell line expressing over 2000 CTG repeats).

Binding to Target RNA

MBNL1 proteins bind YGCY motifs in mRNAs to regulate alternative exon usage and mRNA localization. Mutations in the MBNL1 ZFs have been shown to alter the affinity of MBNL1 for these target RNAs in vitro. The re-organization of the ZF domains within the designed synthetic MBNL1 proteins may alter the affinity and specificity of these proteins for their target RNAs.

Assays with RNA substrates derived from regions of pre-mRNA substrates from MBNL1 regulated splicing events, including TNNT2, mbnl, and ATP2A1, can be performed. For example, the affinity of the synthetic MBNL1 proteins for CCUG repeat RNA (as expressed in DM2) can be determined. To assess the specificity of these proteins, RNAs with mutations in the YGCY motifs can be tested.

Figure 10B:
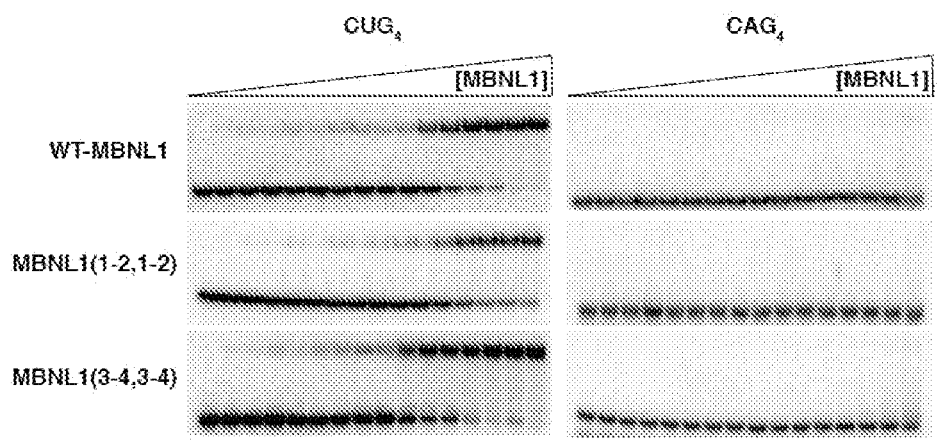
Figure 10C:
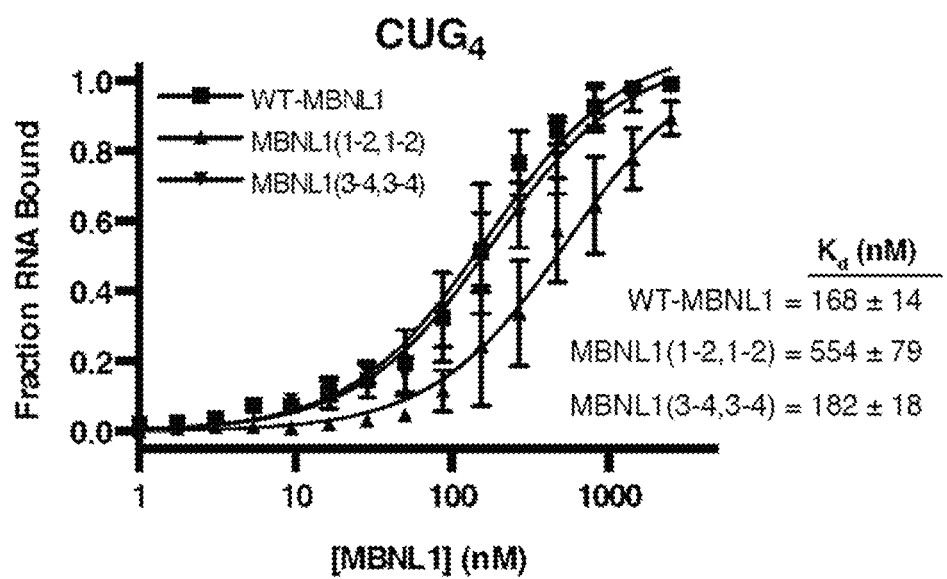

In repeat experiments using different batch of synthetic MBNL proteins to determine if enhanced or disrupted RNA binding correlated with the observed splicing activities of MBNL1(1-2,1-2) and MBNL1(3-4,3-4), separate electrophoretic mobility shift assays (EMSAs) were performed with purified MBNL1 proteins and short model RNAs. The first tested was a $CUG_4$ RNA substrate which contains two UGCU motifs (FIG. 10A) predicted to form a short hairpin designed to mimic the structure CUG repeats are proposed to adopt in DM1. WT-MBNL1 and MBNL1(3-4,3-4) possessed nearly identical binding affinities to the $CUG_4$ RNA while MBNL1(1-2,1-2) had a slightly higher $K_D$ (FIG. 10B-FIG. 10C). As expected, all three proteins had no observable binding to the $CAG_4$ RNA substrate (FIG. 10A) in which the UGCU motifs were mutated to AGCA to weaken MBNL1-RNA interactions (FIG. 10B) (All $K_d$s>2500 nM).

Figure 10D:
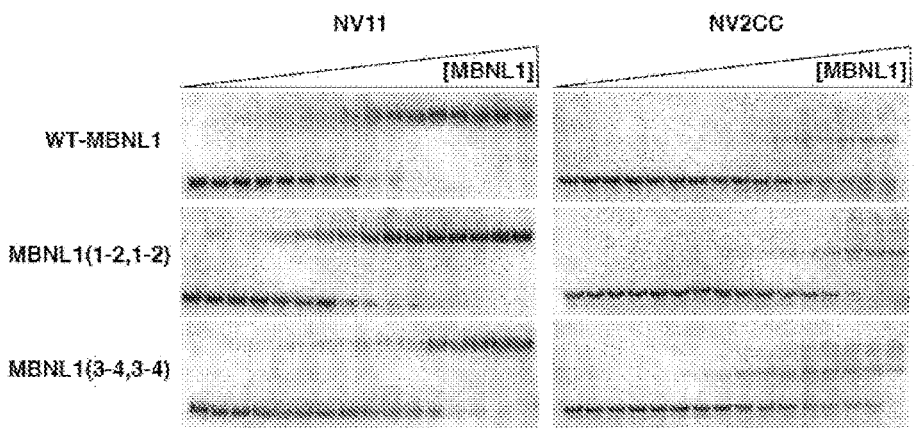
Figure 10E:
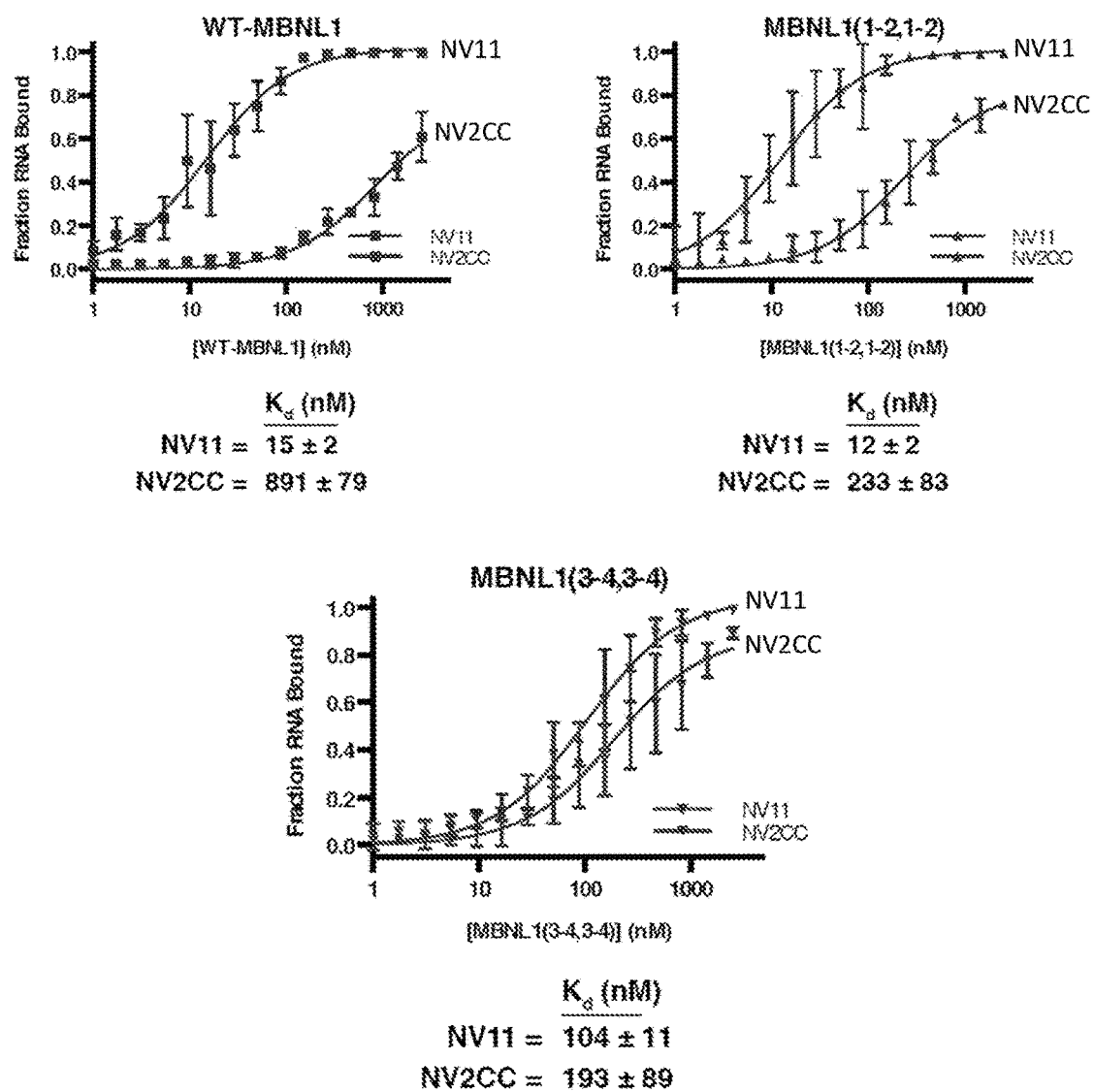

Binding to NV11, a 24-nucleotide, single-stranded RNA substrate that serves as a model for sites in pre-mRNAs with minimal RNA structure, was assayed. This RNA contains two GC dinucleotides separated by an eleven uridine spacer creating two UGCU binding motifs (FIG. 10A). The NV2CC substrate, in which both GC dinucleotides are mutated to CC, was tested (FIG. 10A). This modification to the sequence leads to disruption of the YGCY binding motifs (UGCU to UCCU) and has been shown to significantly weaken MBNL1 binding. WT-MBNL1 and MBNL1(1-2,1-2) had nearly identical, low nanomolar binding affinities to the NV 11 substrate (FIG. 10D-FIG. 10E). In a manner similar to $CAG_4$, both proteins displayed a substantial decrease in RNA binding affinity to the NV2CC construct (FIG. 10D-FIG. 10E). These results indicated that WT-MBNL1 and MBNL1(1-2,1-2) both recognize YGCY motifs with relatively high levels of specificity (59-fold increased recognition of specific motifs for WT-MBNL1 and 18-fold for MBNL1(1-2,1-2)).

MBNL1(3-4,3-4) exhibited a 6-fold decrease in RNA binding affinity for the NV11 RNA substrate compared to WT-MBNL1 (FIG. 10D-FIG. 10E). MBNL1(3-4,3-4) displayed a 2-fold decrease in RNA binding affinity for NV2CC compared to NV11 (FIG. 10D-FIG. 10E). This result indicates that MBNL1(3-4,3-4) partially lost the ability to specifically recognize target YGCY motifs in the context of a pyrimidine rich RNA. This pattern is significantly different from both MBNL1(1-2,1-2) and WT-MBNL1, as both proteins exhibit high affinities for NV11 with significantly increased $K_D$s for NV2CC (FIG. 10E). Overall, these data suggest that MBNL1(3-4,3-4) is primarily a non-specific RNA binding protein. Although it was originally predicted that the differences in splicing activity observed between the synthetic MBNL1 proteins would be due to changes in RNA binding affinity, the results from the EMSA analysis suggested that differences in RNA binding specificity might be responsible.

To more broadly test the RNA binding specificities of the synthetic MBNL1 proteins, RNA Bind-n-Seq (RBNS), a comprehensive, sequencing based approach to characterize sequence specificity of RBPs, was performed. Both WT-MBNL1 and the two synthetic MBNL1 proteins were incubated at increasing concentrations with a pool of random RNA 40mers. The bound RNA, as well as a sample of the un-processed input RNA, was then used to produce cDNA libraries for deep sequencing. Following sequencing, for each protein at each of the tested concentrations, motif read enrichment, or "R" values, were calculated for each kmer (k=7) as the ratio of the frequency of the kmer in the experimental pool as compared to that of the input RNA library. Using this approach, a higher R value is indicative of increased enrichment of a specific motif in the bound RNA pool where R=1 indicates no significant enrichment.

Figure 11A:
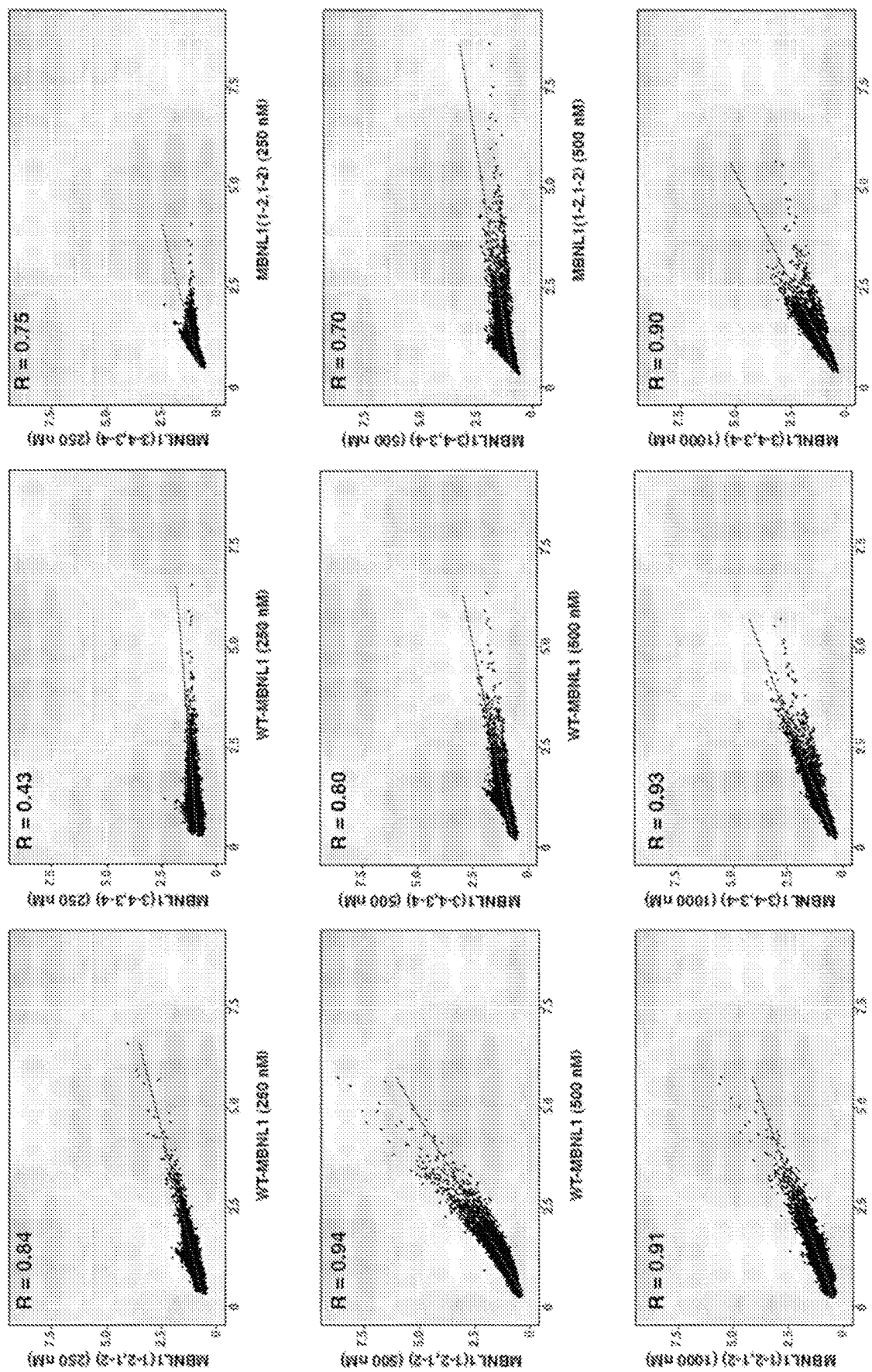
FIG. 11A-FIG. 11C show a comparison of R values and kmers derived from this and other RBNS studies with MBNL1.
Figure 11B:
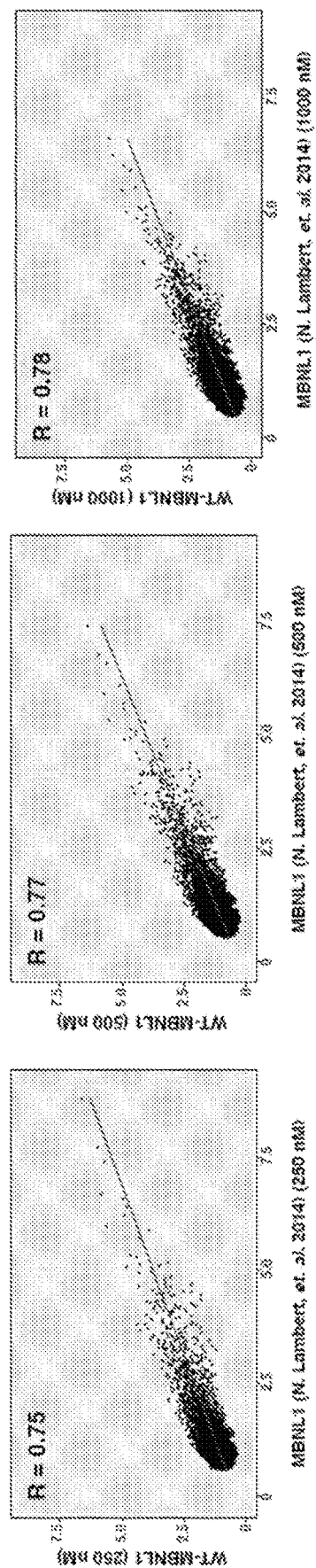
Figure 11C:
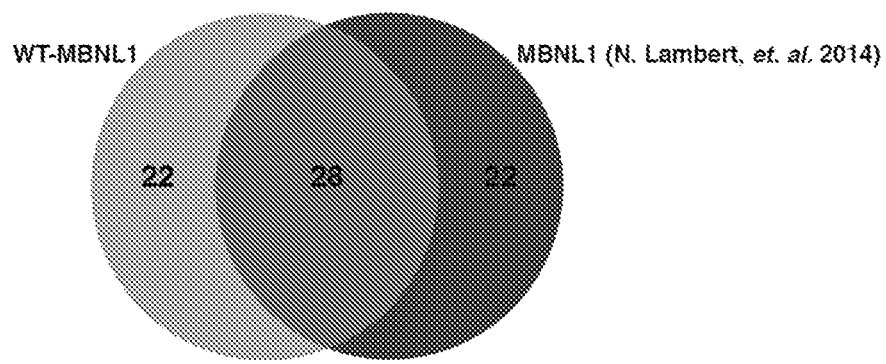

First, data from the RBNS analysis of WT-MBNL1 was compared to that of a previously published RBNS MBNL1 data set. Many of the same top 7mers in both RBNS analyses were observed as well as similar R-values with correlations across the range of protein concentrations (FIG. 11B-FIG. 11C). Correlation coefficients indicated a strong correlation of R values between each MBNL1 protein indicating a similarity in motif recognition and RNA binding activity in each protein population. This indicated that (i) the WT-MBNL1 protein had similar levels of binding activity compared to that utilized in other independent studies and (ii) there is only a modest difference likely due to the different tags utilized in the experimental methodology and changes in the washing step of the protocol (GST vs. a streptavidin binding peptide (35), see Materials and Methods for additional information about experimental design).

Figure 12A:
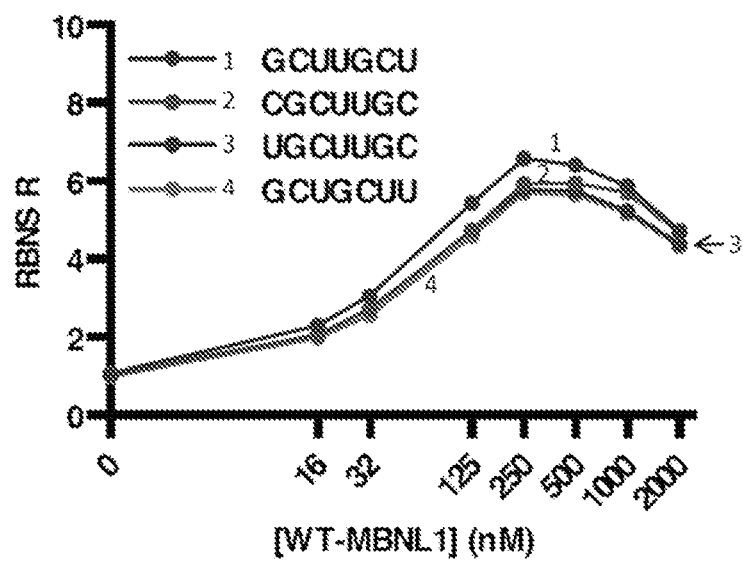
FIG. 12A-FIG. 12E show RBNS analysis of engineered MBNL1 proteins indicating that the ZF domains have altered RNA binding specificity.
Figure 12B:
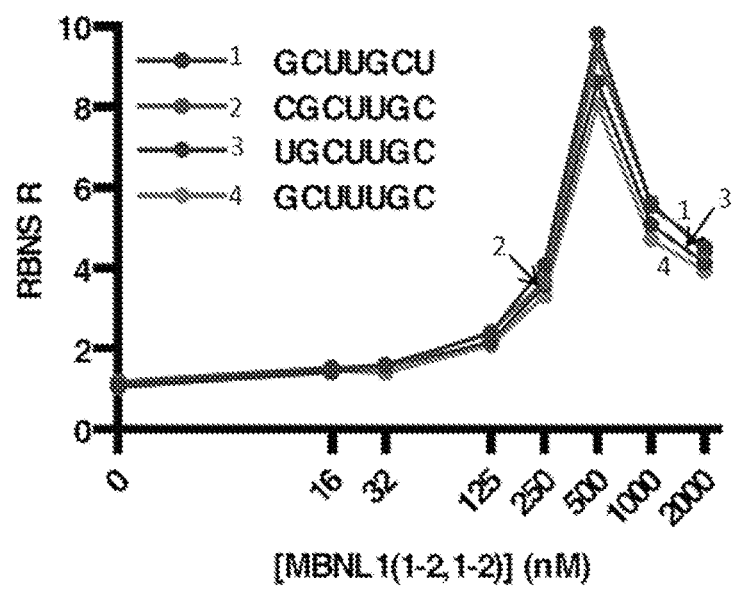
Figure 12C:
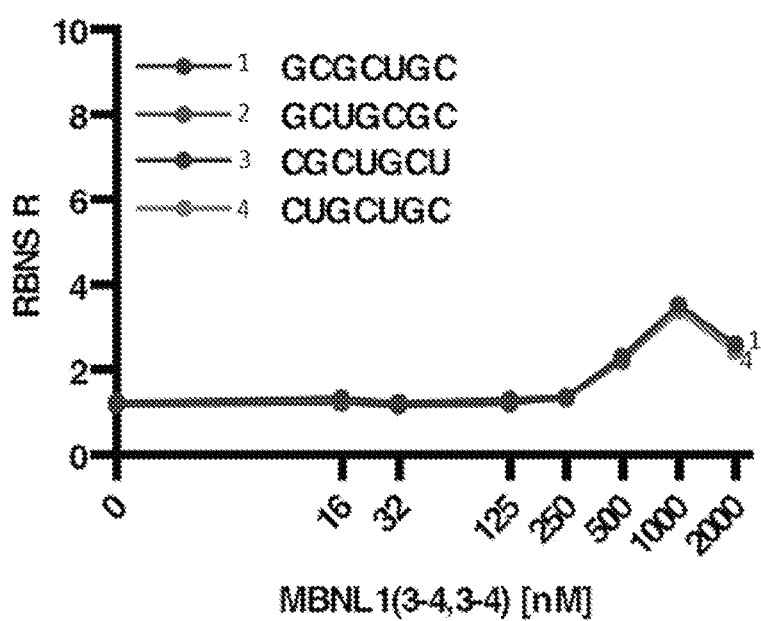
Figure 12D:
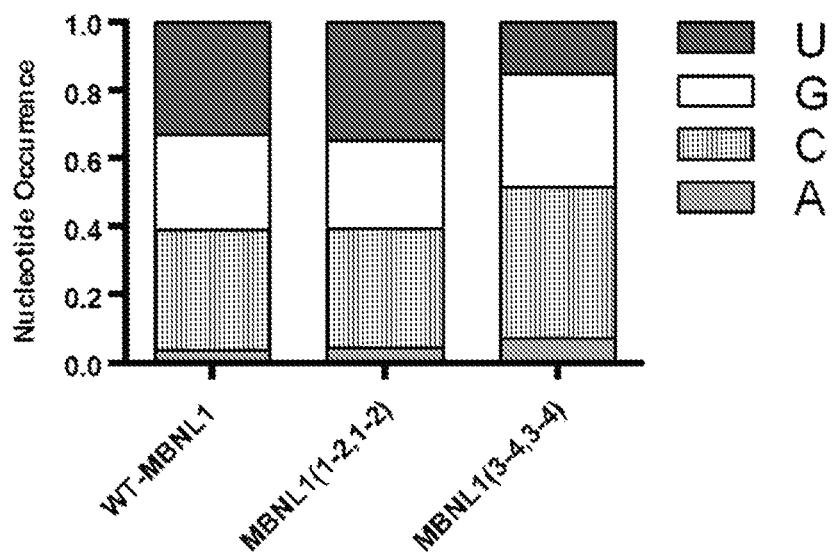
Figure 12E:
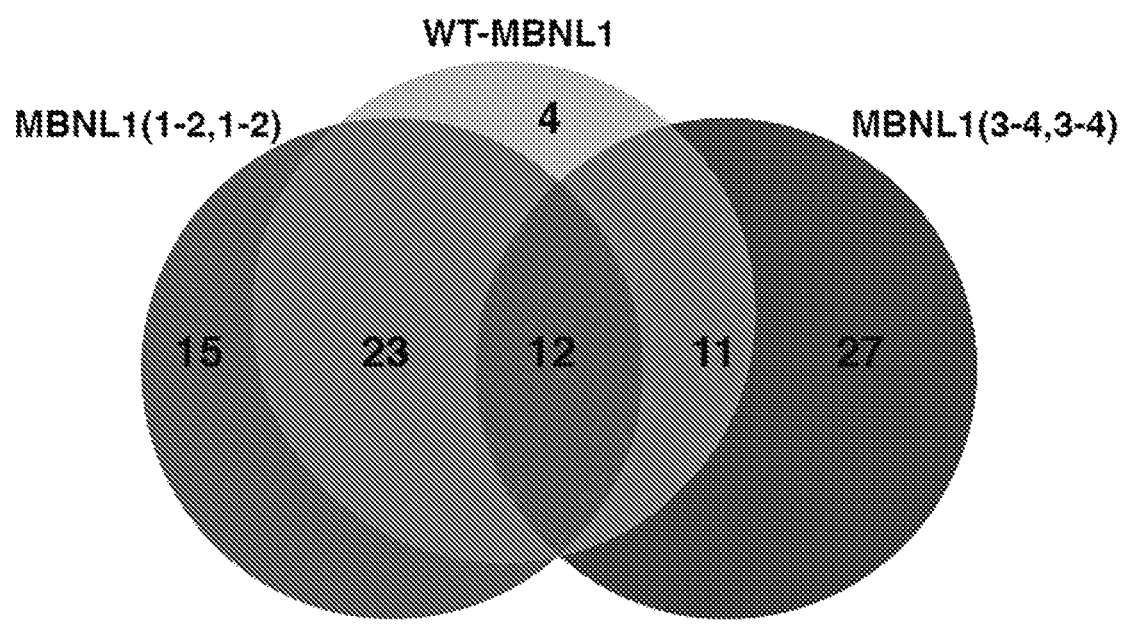

Next, the unimodal enrichment profiles of the top four 7mers for WT-MBNL1 and the two synthetic proteins were compared (FIG. 12A-FIG. 12C). Analysis of these plots revealed several interesting patterns. First, the top three kmers identified were the same for WT-MBNL1 and MBNL1(1-2,1-2) (GCUUGCU, CGCUUGC, and UGCUUGC). All three kmers contain either YGCU or GCUU motifs, with the top kmer of GCUUGCU containing both motifs. Overall, there was significant overlap in the top 50 kmers identified for both proteins as well as similar nucleotide occurrence in the selected motifs (FIG. 12D-FIG. 12E). This indicated that both MBNL1 proteins recognize and bind similar RNA motifs.

The R values for many top kmers were significantly increased for MBNL1(1-2,1-2) compared to WT-MBNL1 (10 versus 7), albeit at different protein concentrations (500 nM vs 250 nM) (FIG. 12A-FIG. 12B). Although this is the most striking difference between these two proteins, the overall pattern is that at lower concentrations, MBNL1(1-2,1-2) has lower R values as compared to WT-MBNL1 until these R values dramatically increased at 500 nM, and then dropped to nearly identical levels at higher protein concentrations (FIG. 12B). In contrast, R values for WT-MBNL1 increased modestly at lower concentrations, peaking at 250 nM and then staying relatively constant (FIG. 12A). This overall pattern suggested that higher concentrations of MBNL1(1-2,1-2) may be needed to achieve specific sequence binding relative to WT-MBNL1, potentially due to loss of cooperative binding as was suggested by the shallower slopes of the splicing dose-response curves (assuming RNA binding correlates to splicing). Despite changes in the shape of the enrichment profiles, there is high correlation in the R values across the protein gradient (FIG. 11A). Correlation coefficients indicated strong similarities between MBNL1 (1-2,1-2) and WT-MBNL1, although some kmers for MBN1L1(3-4,3-4) and WT-MBNL1 are not as strongly correlated and the scatterplots display the overall low R values of MBNL1 (3-4,3-4) across all protein concentrations. Comparison of MBNL1(1-2,1-2) and MBNL1(3-4,3-4) magnifies these differences in RNA binding specificity between the two proteins. Overall, RBNS analysis indicates that while MBNL1 (1-2,1-2) and WT-MBNL1 bind and recognize similar RNA motifs, MBNL1(1-2,1-2) has increased RNA binding specificity for many of these motifs.

MBNL1(3-4,3-4) selected a different set of top kmers that contain fewer uridines (GCGCUGC, GCUGCGC, CGCUGCU, and CUGCUGC) (FIG. 12C). Percent nucleotide occurrence within the top 100 kmers showed a reduction of uridines and a modest enrichment in guanosines and cytosines (FIG. 12D). Due to this change in the distribution of nucleotides in the enriched MBNL1(3-4,3-4) kmers, fewer YGCU and UGCU motifs were identified. As such, fewer overlapping motifs were found between the top 50 kmers of MBNL1(3-4,3-4) and the other tested MBNL1 proteins (FIG. 12E). Consistent with modest RNA binding specificity, the enrichment profiles for MBNL1(3-4,3-4) have low R values across the gradient of protein concentrations, peaking at R=3 at 1000 nM for the most enriched motifs (FIG. 12C). Overall, the EMSA and RBNS data for MBNL1(3-4,3-4) indicate that this synthetic MBNL1 has significantly reduced RNA binding specificity while maintaining general RNA binding affinity. This is a sharp contrast to MBNL1(1-2,1-2) in which RBNS revealed that this synthetic protein has enhanced YGCY RNA sequence recognition over WT-MBNL1. These overall changes in binding specificity are consistent with a model in which ZF1-2 confers specific sequence recognition while ZF3-4 acts as a more general RNA binding domain in the context of both WT-MBNL1 and the synthetic derivatives.

Synthetic MBNL1 Proteins Rescue CUG-Dependent Mis-Splicing in a DM1 Cell Model

Figure 13A:
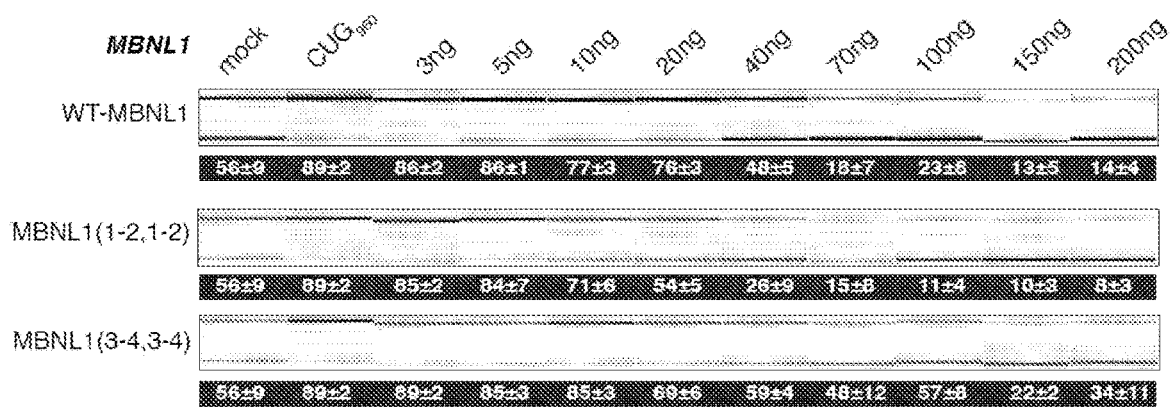
FIG. 13A and FIG. 13B show representative splicing gels used to create dose response curves with plasmid dosing system in the presence of toxic RNA for MBNL1 (FIG. 13A) and ATP2A1 (FIG. 13B) minigene reporters, respectively, in the presence of CUG repeat RNA. Images were acquired using the Advanced Analytical Fragment Analyzer. Bands are representative of relative fluorescence units (RFU) for each cDNA product and were used to calculate ψ for each plasmid dose. Average ψ±standard deviation at each plasmid dose are listed below each gel (n=3-5 for each).
Figure 13B:
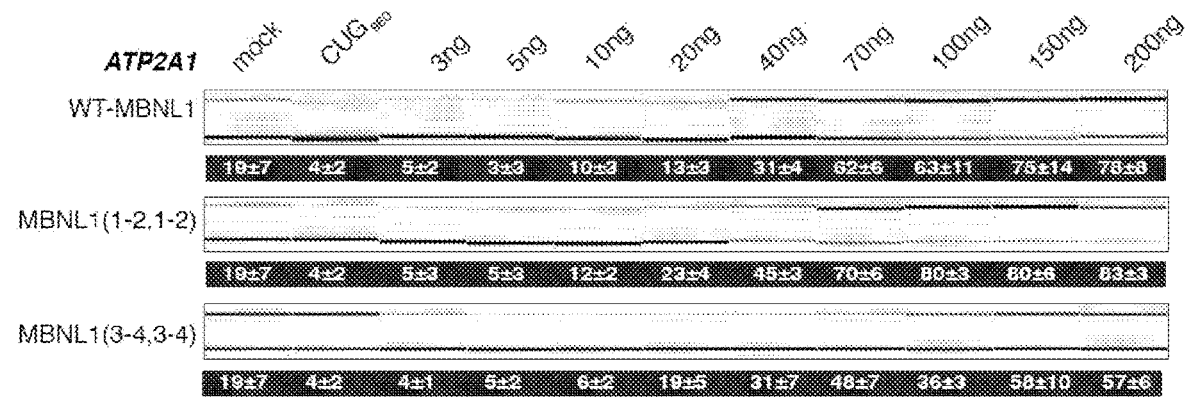

Given the differences in splicing activity and RNA binding specificity of the synthetic MBNL1 proteins, the aim was to determine if these proteins could rescue CUG-mediated mis-splicing like that found in DM1. This was accomplished by expressing CUG repeats from a plasmid containing 960 interrupted CTG repeats (DMPK-CTG$_{960}$, a.k.a CUG$_{960}$) in culture. Transfection of DMPK-CTG$_{960}$ in HeLa cells has previously been shown to lead to MBNL co-localization with CUG repeat RNA in nuclear foci and mis-splicing of MBNL1-regulated minigenes (31, 41, 46). The same plasmid dosing system used previously (FIG. 9A-FIG. 9D) was used with co-transfection of the CUG$_{960}$ repeat plasmid, minigene reporter, and MBNL1 expression construct to monitor ψ changes across the gradient of protein expression for the MBNL1 and ATP2A1 minigenes (representative images used to calculate ψ shown in FIG. 13A-FIG. 13B). These results were also compared to those generated in the absence of CUG repeat RNA expression.

Figure 14A:
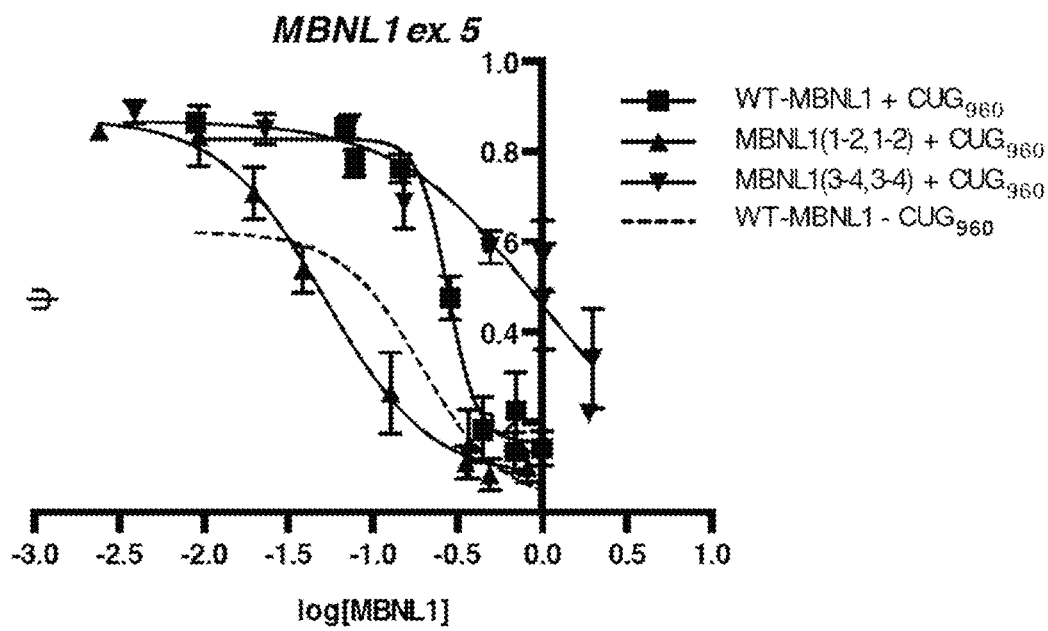
FIG. 14A-FIG. 14C show that dose curves of synthetic MBNL1s are altered in the presence of toxic RNA.
Figure 14B:
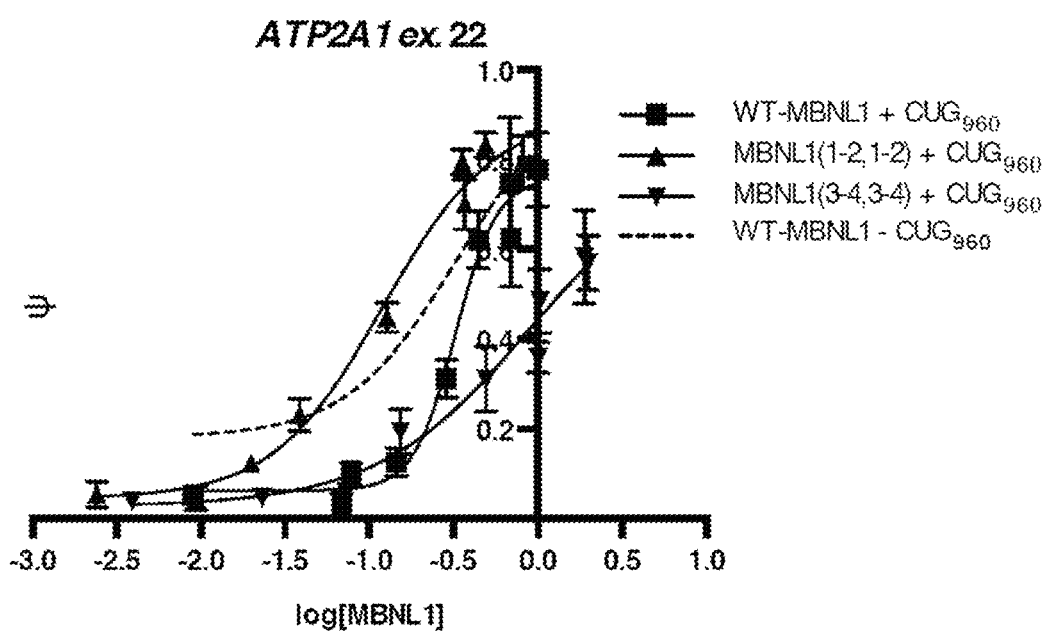
Figure 14C:
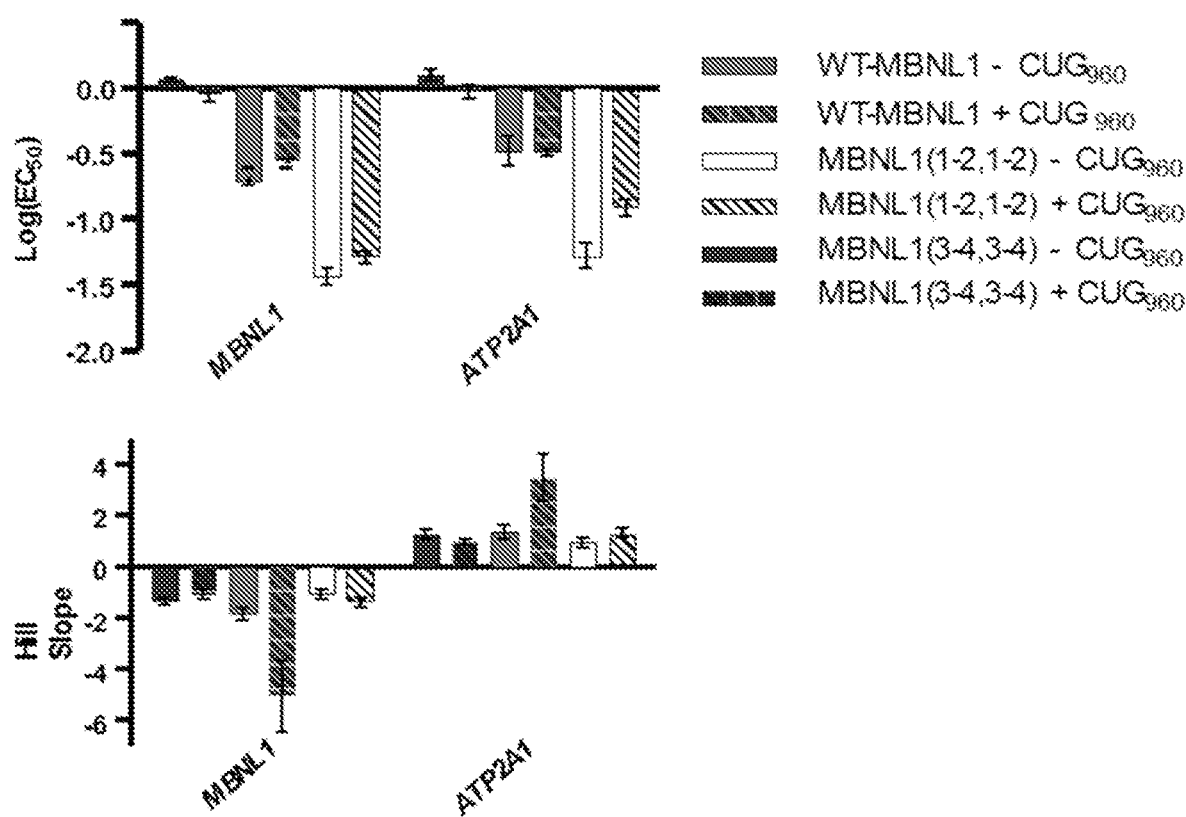
Figure 15A:
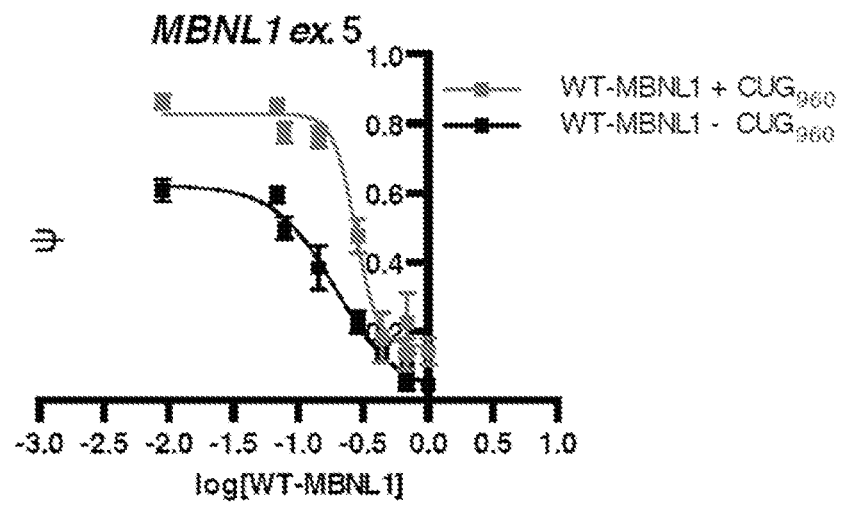
Figure 15A:
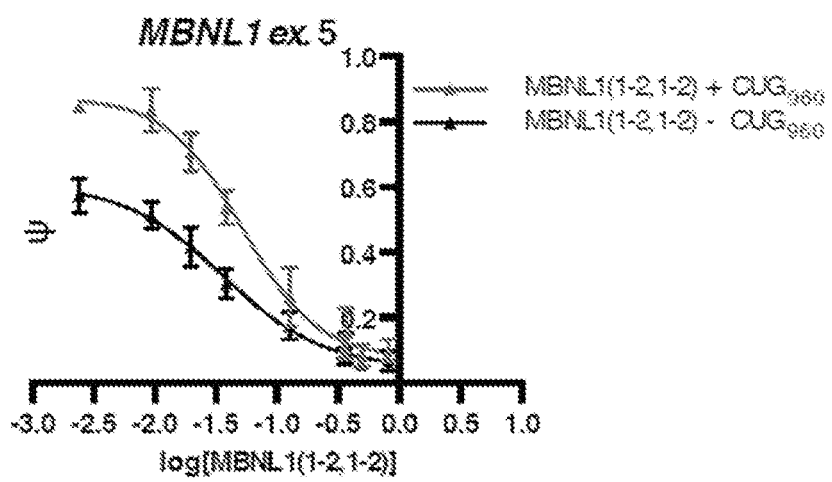
Figure 15A:
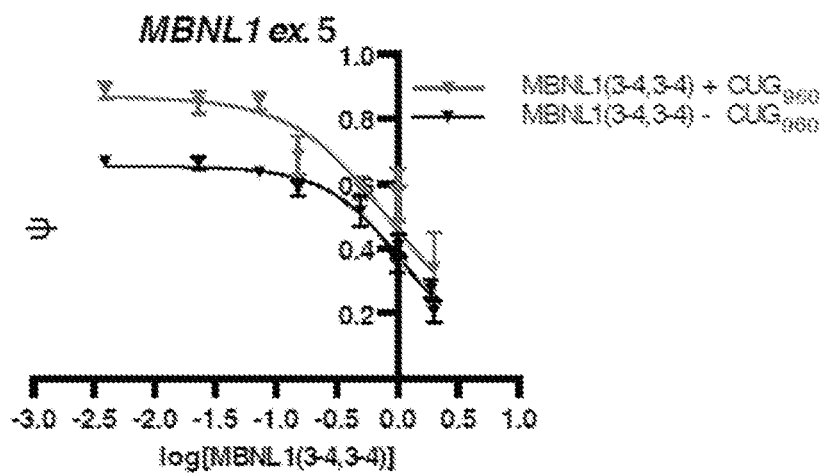
Figure 15B:
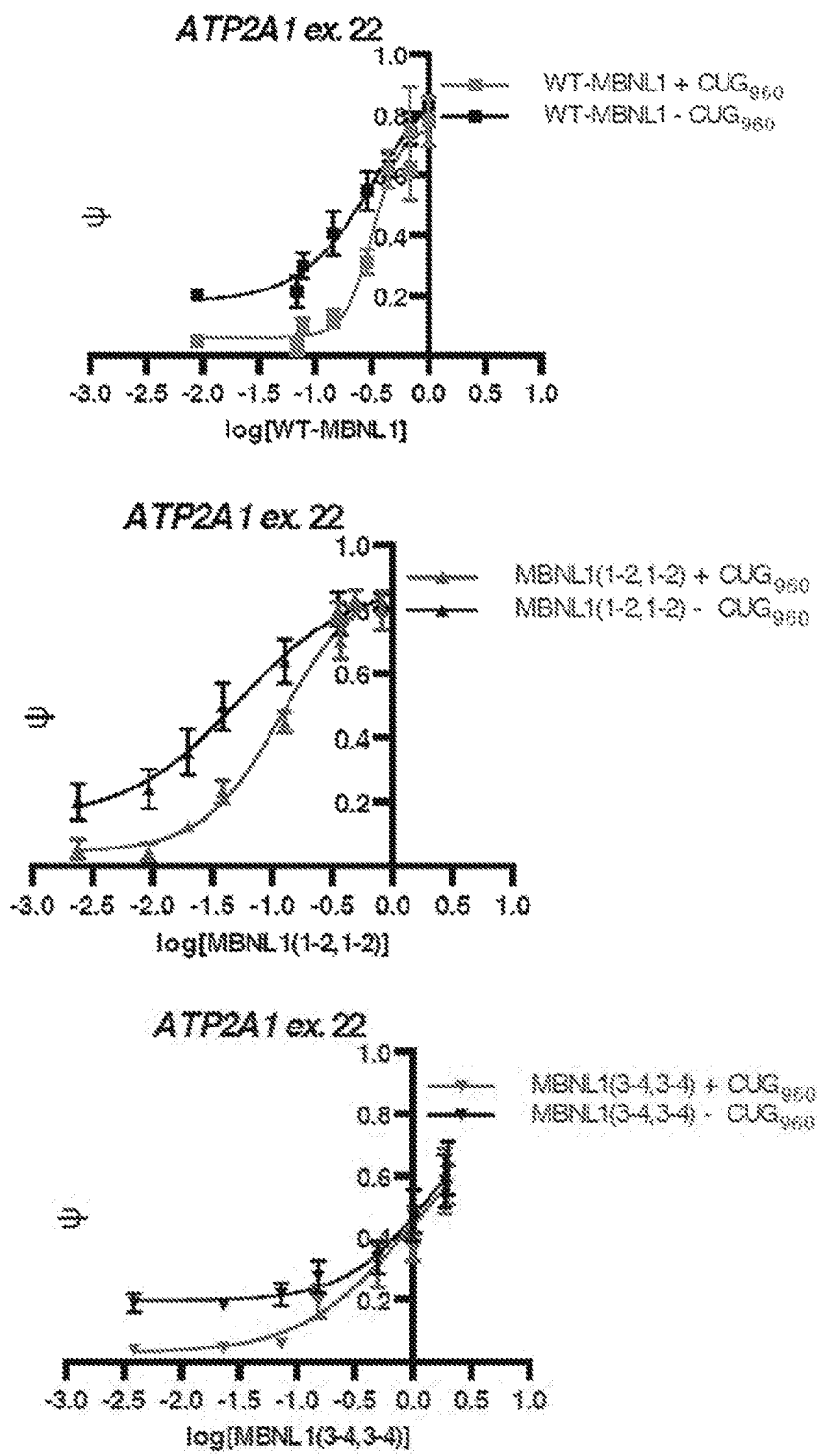

Co-expression of CUG$_{960}$ led to reduced splicing activity for all three proteins at low protein levels (FIG. 14A-FIG. 14B), presumably due to sequestration of MBNL proteins. At higher protein expression levels, all three MBNL1 proteins were able to reach maximal splicing regulation (maximal ψ) equivalent to that in the absence of CUG repeats (FIG. 14A-FIG. 14B and FIG. 15A-FIG. 15B). FIG. 15C shows quantitative parameters (log(EC$_{50}$) and Hill Slope, ±standard error) generated from the dose-response curves in the presence and absence of toxic repeat RNA expression. The addition of CUG repeats had no effect or only a modest effect on the EC$_{50}$ values for all 3 proteins and the two minigene reporters (FIG. 14C). An increase in the slopes of the dose-response curves for WT-MBNL1 for both events studied was significant (FIG. 14C). The overall effects on the dose-response curves with the addition of CUG repeats are consistent with a model in which at low levels of MBNL1 all of the protein is sequestered by the CUG repeats and unable to regulate splicing. As the concentration of MBNL1 increases, binding to the CUG repeats is saturated, leading to a replenishment of free, active MBNL1 in the nucleus and effective splicing rescue. Despite the changes in the dose-response curves in the presence of toxic RNA, MBNL1(1-2,1-2) remained the most active protein (lowest EC$_{50}$ values) for both minigene reporters (FIG. 14C).

SUMMARY AND DISCUSSION

Synthetic MBNL1 Proteins with Altered RNA Binding Specificity have Differential Splicing Activity To gain insight into the function of the individual ZF domains, a synthetic biology approach was utilized to engineer and biochemically characterize two synthetic MBNL1 proteins with altered ZF domain content, e.g., MBNL1(1-2,1-2) and MBNL1(3-4,3-4). Using this system it was determined that ZF1-2 has increased RNA binding specificity over ZF3-4 which led to enhanced alternative splicing activity of the synthetic MBNL1(1-2,1-2) protein. Additionally, it was showed that MBNL1(1-2,1-2) was capable of rescuing CUG-dependent mis-splicing in a DM1 cell model at lower protein concentrations than WT-MBNL1, indicating that these synthetic proteins could potentially be used as therapeutics to replace or displace sequestered MBNL1 from foci in DM patient cells.

Splicing assays, in vitro EMSAs, and RBNS analysis revealed that MBNL1(1-2,1-2) is a more active derivative of WT-MBNL1 and can regulate alternative splicing of RNA targets at lower protein concentrations (FIG. 9A-FIG. 9D and FIG. 14A-FIG. 14C). Overall, MBNL1(1-2,1-2) had 5-fold increased activity compared to WT-MBNL1. In contrast, MBNL1(3-4,3-4), although still functional, had 4-fold weaker activity compared to WT-MBNL1. It was predicted that these variations in effective splicing activity would be due to altered binding affinity to RNA targets, but EMSA and RBNS studies suggest that changes in RNA specificity appear to be primarily responsible for the observed alternations in splicing regulation (FIG. 10A-FIG. 10E and FIG. 12A-FIG. 12E). MBNL1(1-2,1-2) retained the ability to recognize YGCY motifs with increased specificity compared to WT-MBNL1 (FIG. 12A-FIG. 12E). In contrast, MBNL1 (3-4,3-4) had very low RNA binding specificity overall with diminished recognition of canonical YGCY motifs (FIG. 12A-FIG. 12E).

Figure 16:
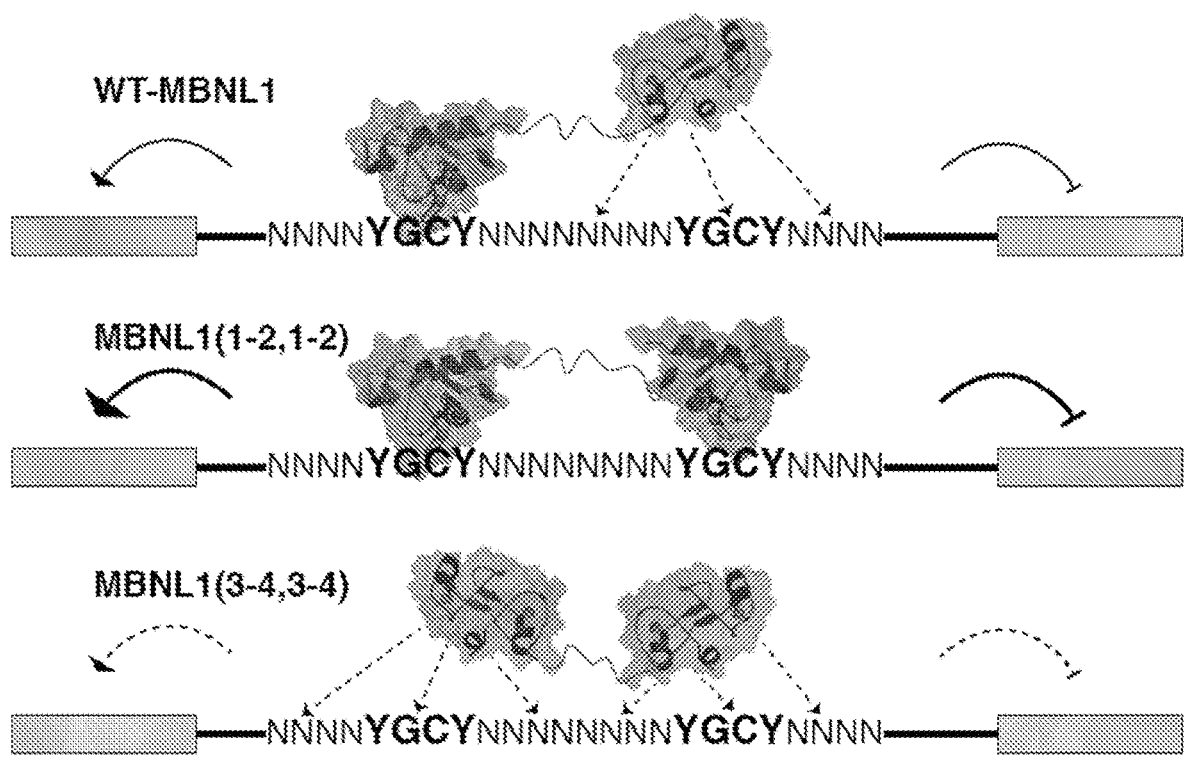
FIG. 16 shows a model summarizing differences between WT-MBNL1 and synthetic MBNL1 proteins. Structures of domains shown here are derived from PDB ID 3D2N (ZF1-2) and PDB 3D2Q (ZF3-4) (32).

FIG. 16 provides a working model for the synthetic proteins. MBNL1 (1-2,1-2) is a more active alternative splicing regulator while MBNL1(3-4,3-4) is significantly weaker compared to WT-MBNL1. These differences in activity are represented by the size of the arrows showing how each MBNL1 protein promotes exon inclusion/exclusion. In the context of WT-MBNL1, ZF1-2 binds YGCY motifs with high specificity while ZF3-4 has a modest preference for YGCY motifs but will sample and bind many motifs with similar affinities. This activity is represented by the dotted lines illustrating ZF3-4 binding to both canonical and non-canonical RNA motifs. MBNL1(1-2,1-2) possesses two high-specificity ZF1-2 motifs driving RNA recognition and subsequently increased splicing regulation at lower protein concentrations. MBNL1(3-4,3-4) has significantly reduced RNA binding specificity and samples many specific and non-specific RNA motifs. Due to the reduced motif recognition, regulatory sites are not bound until high concentrations of protein are present leading to an overall reduction in splicing regulation. Overall, the working model (summarized in FIG. 16) is that in the context of WT-MBNL1, ZF1-2 drives splicing activity via specific binding to YGCY motifs in the appropriate sites of pre-mRNA substrates. ZF3-4, with its modest preference for YGCY motifs, will sample and bind many RNA motifs providing general binding affinity for WT-MBNL1. It is possible that MBNL1(1-2,1-2) with two high specificity domains has heightened recognition of MBNL1 YGCY regulatory elements leading to increased splicing activity. In contrast, this model is that MBNL1(3-4,3-4) will bind many off-target sites leading to reduced occupancy at the sites needed for regulation of alternative splicing by MBNL1, resulting in the need for high concentrations of this protein for splicing regulation.

The results from the cell-based assays are consistent with the proposed model of alternative splicing regulation by the synthetic MBNL1 proteins. In general, MBNL1(3-4,3-4) weakly regulated all tested minigene events, but achieved nearly complete splicing regulation with MBNL1 and ATP2A1. Both events possess many functional clusters of YGCY motifs (31, 47), and MBNL1(3-4,3-4) with its low specificity binds the high density sites with sufficient occupancy to regulate splicing. The TNNT2 substrate contains only two UGCU motifs separated by the polypyrimidine tract within intron 4 (41), and these two sites may not be sufficient to recruit MBNL1(3-4,3-4) to this substrate accounting for the acutely weak regulation of this event. Alternatively, it is possible that the synthetic MBNL1 proteins have altered recognition of specific RNA structural elements. Recognition of a helical element within the TNNT2 pre-mRNA is proposed to be required for regulation by MBNL1 (41). MBNL1(1-2,1-2) may have enhanced recognition of structured RNAs which may account in part for its increased splicing regulation of this event. Another alternative possibility is that the ZF1-2 domain interacts with other splicing factors that bind the TNNT2 pre-mRNA and the duplication of the ZF1-2 domain improves recruitment and leads to the higher level of splicing activity observed (FIG. 3D and FIG. 3G).

ZF1-2 and ZF3-4 Possess Distinct RNA Binding Activities that Modulate MBNL1 Activity Overall, the results with the synthetic MNBL1 proteins indicate that ZF1-2 and ZF3-4 are independent domains and can be reorganized without obvious negative impacts on protein function. The results indicate that ZF1-2 drives splicing regulation (FIG. 3D and FIG. 9A-FIG. 9D) via specific recognition of YGCY motifs (FIG. 12A). This activity is consistent with observations that MBNL1 orthologs in D. melanogaster and C. elegans which contain only a single ZF pair orthologous to ZF1-2 can regulate exon inclusion in a manner similar to human MBNL1 in cell culture (37). The differential protein levels of the synthetic proteins (FIG. 3E and FIG. 2H), suggest that the ZF3-4 domain may confer stability to MBNL1. Consistent with this hypothesis, increased mammalian (FIG. 3E and FIG. 3G) and bacterial protein expression were observed for MBNL1 (3-4,3-4); in contrast levels of MBNL1(1-2,1-2) were reduced in both systems.

The differences between ZF1-2 and ZF3-4 observed in this study are possibly due to subtle changes in the architecture and sequence of the ZF domains (FIG. 2D). The major difference between the two ZF pairs is the extended α-helix at the C-terminus of ZF2 (32). The interdomain linker between ZF1 and ZF2 is two residues shorter than the linker in ZF3-4 (32). Many amino acid differences exist between the domains although most of the amino acids that were shown to make contact with RNA in the crystal structure of ZF3-4 with RNA are conserved (32). These changes in domain architecture between ZF1-2 and ZF3-4 are conserved in all three human MBNL homologs (MBNL1/MBNL2/MBNL3) (see FIG. 2E for sequence alignment). The differences in activity between these domains are predicated to be maintained across MBNL1, MBNL2, and MBNL3 and potentially more broadly across MBNL proteins throughout metazoans (37).

Modular Architecture of MBNL1 ZF Domains Provides a Unique Platform for RNA Recognition Although RBPs have a broad range of functions, they are often built from relatively few RNA binding domains. To increase the functionality and specificity of their target interactions, multiple RNA binding domains are frequently found in RBPs. A classic example of this is the Pumilio (PUF) family of RBPs, where up to 8 tandem domains that each recognize a single nucleotide can be combined on a single polypeptide chain to create a highly specific RNA interaction surface. In a similar manner it is proposed that the modular architecture of MBNL1 with its two tandem ZF pairs increases the protein-RNA binding surface. This working model is that ZF1-2 drives splicing regulation through specific recognition of YGCY motifs and the ZF3-4 domain binds secondarily to a broader range of motifs to allow MBNL1 to recognize a wide range of substrates (FIG. 16). Additionally, the domain organization and differences in RNA binding specificity between the ZF pairs may explain the relative levels of cooperativity observed in the dosing experiments (FIG. 9A-FIG. 9D and FIG. 14A-FIG. 14C), assuming binding of the MBNL1 proteins correlates to splicing. One possible mechanism for cooperativity is that binding of one WT-MBNL1 protein facilitates the binding of one or more additional MBNL1 proteins or other splicing factors to a pre-mRNA substrate. These additional binding events mediated by WT-MBNL1 may shift splicing decisions over tighter protein gradients compared to the two synthetic MBNL1s, which both possess less cooperative splicing curves.

This model of a modular RBP containing multiple domains, one for specific RNA recognition and the other with broader target binding, has been utilized by several other RBPs, including those containing CCCH (SEQ ID NO: 80) zinc finger motifs. One example is the neuronal protein Unkempt, a highly conserved RBP that binds to its target mRNAs to reduce translation and is required for the establishment of neuronal morphology in development. Unkempt contains six CCCH (SEQ ID NO: 80) ZF domains that form two tandem clusters, each with three ZFs [ZF1-3 and ZF4-6]. Both CLIP and structural data confirm that ZF1-3 binds to a UAG trinucleotide while ZF4-6 binds to a more variable U-rich motif. Mutational analysis of RNAs bound to Unkempt in vitro revealed that the UAG motif was mandatory for binding while alterations to the downstream U-rich element were more tolerated. These data suggest that in a manner similar to MBNL1 ZF1-2, Unkempt ZF1-3 drives RNA recognition via binding to the UAG sequence while binding to the less "specific" U-rich motif by ZF4-6 allows for recognition of a wider array of RNA substrates in a manner similar to MBNL1 ZF3-4. The similar modes of MBNL1 and Unkempt RNA interactions suggest this might be a common strategy for RNA binding proteins.

Engineered MBNL1s as Protein Therapeutics in Neuromuscular Disorders

The creation of designer RBPs has increased over the past several years as a means to modulate RNA function. Although the traditional methodology of engineering these proteins often focuses on combining domains to target a specific RNA sequence of interest, such as with the PUF proteins, a different, non-traditional synthetic design strategy was utilized. The pre-existing activity and specificity of MBNL1 was enhanced by re-combining its ZF domains. No such designer RBP has previously been created that focuses on enhancement of protein function via duplication of specific modular RNA binding domains. This design strategy may be the most effective for engineering RBPs as protein therapeutics in which the function of a target protein is decreased or absent such as in DM.

MBNL1 overexpression has been proposed as a therapeutic strategy in the DM field to ameliorate symptoms caused by the loss of free MBNL1 in CUG/CCUG RNA foci. Delivery of MBNL1 through adeno-associated virus (AAV) has been shown to rescue mis-splicing events in a DM1 mouse model and reverse disease associated symptoms in skeletal muscle, including myotonia. Additionally, MBNL1 overexpression has been shown to be well-tolerated in non-disease mice, suggesting that therapies designed to increase levels of free, active MBNL1 in the cell could be an effective strategy for treatment of DM. Delivery of a synthetic MBNL1 with increased activity, such as MBNL1(1-2,1-2), could be a powerful approach to correct disease-specific mis-splicing. The use of a synthetic MBNL1 as a protein therapeutic is potentially ideally suited for Fuchs Endothelial Corneal Dystrophy where the protein would only need to be delivered to the more easily accessible tissue of the eye. This work to create a synthetic MBNL1 serves as a proof of principle that MBNL1 tolerates domain reorganization and can be manipulated while retaining function. Further rational design strategies to modify MBNL1 could be utilized moving forward to continue to create a smaller, more stable, and higher activity synthetic MBNL1 for use in disease therapies. Overall, this study indicate that engineered RNA binding proteins with improved splicing activity may represent a therapeutic avenue for DM and other microsatellite diseases.

Accordingly, in some aspects, synthetic MBNL1 proteins, specifically MBNL1(1-2,1-2), show improved splicing activity. The successful creation of these active synthetic proteins has not only revealed that the ZF domains of MBNL1 can be manipulated and uncoupled from one another while remaining functional, but has also provided a platform for the creation of other synthetic MBNL1 proteins. Furthermore, truncations in both the C-term and the linker, that can improve solubility properties, can be made without loss of splicing activity and RNA binding activity. These proteins can be used for the treatment of repeat expansion disorders in which MBNL proteins are sequestered (e.g., DM1, DM2, FECD, or SCA8).

In some embodiments, the rearrangement of the ZF pairs of an MBNL protein can also alter protein stability.

Materials and Methods
Protein Design, Synthesis, and Cloning

The wild-type (WT) MBNL1 protein (amino acids 1-382; splice isoform a; NCBI accession number NP_066368) was used as a template for the construction of the truncated WT-MBNL1, MBNL1(1-2,1-2), and MBNL1(3-4,3-4). Due to the difficulty of purifying MBNL1 with the C-terminal region (amino acids 261-382) and to reduce the size of the synthetic proteins, this portion of the protein was excluded in the synthetic design. Previous studies have shown that the C-terminal region is not required for high-affinity RNA binding. WT-MBNL1 was created using primers to add the N-terminal HA tag and the C-terminal nuclear localization signal (SV40 NLS). The sequence of MBNL1(1-2,1-2) and MBNL1(3-4,3-4) were synthesized by (GenScript, Piscataway, N.J.). All three proteins were cloned into pCI (Promega) for mammalian expression and pGEX-6P1 (Amersham, Pittsburgh, Pa.) for bacterial protein expression using XhoI and NotI sites. The amino acid sequences of WT-MBNL1 and synthetic MBNL1 constructs are reported in FIG. 2C.

Cell Culture and Transfection

HeLa cells were cultured as a monolayer in Dulbecco's modified Eagle's medium (DMEM)-Glutamax (Gibco, Carlsbad, Calif.) supplemented with 10% fetal bovine serum and 1× antibiotic-antimycotic (Gibco) at 37° C. under 5% $CO_2$. Prior to transfection, cells were plated in twelve-well plates at a density of $8 \times 10^4$ cells/well. Cells were transfected approximately 36 hours later at roughly 80% confluency. Plasmids (400 ng/well) were transfected into each well with 2 µl of Lipofectamine 2000 (Invitrogen, Carlsbad, Calif.) as per the manufacturer's protocol. Cells were placed in Opti-MEM I reduced serum media (Gibco) at the time of transfection. Six hours later the Opti-MEM I was replaced with supplemented DMEM. 18 hours post-medium exchange cells were harvested using TrypLE (Gibco) and pelleted using centrifugation. For overexpression cell-based splicing assays (FIG. 3D) and western blots (FIG. 3E), 200 ng of protein plasmid or empty pCI vector (mock) were co-transfected with 200 ng of minigene. In the context of the plasmid dosing system (both splicing assays and western blots) (FIG. 9A-FIG. 9D and FIG. 7), 200 ng of a selected minigene were co-transfected with increasing amounts of protein plasmid up to 200 ng. In cases where less than 200 ng were transfected, empty pCI vector was used to make up the remainder of the total 400 ng added to the cells. When plasmid dosing was performed in the context of CUG repeat RNA (FIG. 12A-FIG. 12E), the amount of protein expressing vector remained unchanged from previous dosing experiments, but only 100 ng of the selected minigene was transfected with 100 ng of a DMPK-$CUG_{960}$ expressing plasmid.

HEK-293 cells (Flp-In T-Rex 293, Invitrogen) were routinely cultured as a monolayer in DMEM-Glutamax (Gibco)

supplemented with 10% fetal bovine serum and 10 µg/ml basticidin/300 µg/ml zeocin. Prior to transfection, cells were plated in twenty four-well plates at a density of 1.5×10⁵ cell/well. Cells were transfected 24 hours later at roughly 80% confluency. Plasmids (500 ng/well) were transfected into each well with 1.5 µl of Transit-293 (Mirus Bio LLC, Madison, Wis.) as per the manufacturer's protocol. For all overexpression cell-based splicing assays (FIG. 3G) and westerns (FIG. 2H) 250 ng of protein expressing plasmid or empty pCI vector (mock) were co-transfected with 250 ng of minigene reporter. 24 hours post-transfection cells were harvested using TrypLE (Gibco) and pelleted using centrifugation.

Immunofluorescence

Eight-well culture slides were treated with poly-lysine solution (Sigma-Aldrich, St. Louis, Mo.) for 30 minutes at 37° C. HeLa cells were then plated at 2×10⁴ cells/chamber. Cells were transfected 24 hours post-plating with 200 ng total plasmid (100 ng protein expression plasmid and 100 ng of empty pCI vector, 200ng of pCI for mock) using 1 µl of Lipofectamine 2000 (Invitrogen) as per the manufacturer's protocol. Cells were placed in Opti-MEM I reduced serum media (Gibco) at the time of transfection. Six hours later the Opti-MEM I was replaced with supplemented DMEM. 18 hours post-medium exchange cells were fixed for 10 minutes on ice with 4% paraformaldehyde. Cells were then permeabilized with 0.1% Triton X-100 in 1×PBS for 10 minutes at room temperature (RT). Next, cells were treated with Image-iT FX Signal Enhancer (Invitrogen) for 30 minutes at RT. The cells were probed overnight at 4° C. with mouse anti-HA antibody (1:100 dilution, 6E2, Cell Signaling Technology, Danvers, Mass.). After 3 washes in 1×PBS for 5 minutes at RT, cells were then probed with goat anti-mouse Alexa 488 (5 µg/ml dilution, Invitrogen) for 1 hour at RT. Finally, cells were mounted using Prolong Diamond Antifade Mountant with DAPI (Invitrogen). After the slides had cured, images were acquired using a Zeiss Axioskop 2 (Oberkochen, Germany) with equal exposures across all samples.

Real-Time PCR

RNA from HeLa cells transfected with empty vector (mock) or plasmid expressing an MBNL1 protein were isolated and reverse-transcribed into cDNA using SuperScript IV (Invitrogen) with random hexamer priming. Real-time PCR analysis was then conducted using SsoAdvanced Universal SYBR Green Supermix (Bio-Rad, Hercules, Calif.) on a CFX96 Touch Real-Time PCR Detection System (Bio-Rad) as per the manufacturer's guidelines. Primers utilized are as listed: WT-MBNL1/MBNL1(1-2,1-2), MBNL1(3-4,3-4) (forward: 5'-AGAGAAAGGTCGAAT-GAGCGG-3', SEQ ID NO: 45, reverse: 5'-TGCAT-TCTAGTTGTGGTTTGTCC-3', SEQ ID NO: 46) and GAPDH (forward: 5'-AATCCCATCACCATCTTCCA-3', SEQ ID NO: 47, reverse: 5'-TGGACTC-CACGACGTACTCA-3', SEQ ID NO: 48). Expression levels of MBNL1 were determined via normalization of the cycle threshold (Ct) to GAPDH. Calculations of fold change relative to WT-MBNL1 were determined via the formula $2^{-\Delta\Delta ct}$.

Western Blot Analysis

Cell pellets were lysed in RIPA (25 mM Tris-HCl pH 7.6, 150 mM NaCl, 1% NP-40, 1% sodium deoxycholate, 0.1% SDS, Thermo Fisher Scientific, Waltham, Mass.) supplemented with 1 mM phenylmethylsulfonyl fluoride (PMSF) and 1× protease inhibitor cocktail (SigmaFAST, Sigma-Aldrich) by light agitation for 15 minutes via vortex. Equal amounts of lysate were resolved on a 10% SDS-PAGE gel prior to transfer. MBNL1 proteins were then probed using a mouse anti-HA (1:1000 dilution, 6E2, Cell Signaling Technology) and goat anti-mouse secondary IRDye 800CW (1:15000 dilution, LI-COR Biosciences, Lincoln, Nebr.). A GAPDH loading control was probed using rabbit anti-GAPDH (1:1000 dilution, 14C10, Cell Signaling Technology) followed by goat anti-rabbit IRDye 680RD (LI-COR Biosciences). Fluorescence was measured using a LI-COR Odyssey Fc or LI-COR Odyssey CLx Imaging instrument. Quantification was performed using the associated Image Studio analysis software (LI-COR Biosciences).

Cell-Based Splicing Assay

RNA was isolated from HeLa and HEK-293 cells using an RNeasy kit (Qiagen, Hilden, Germany) or *Aurum* Total RNA Mini kit (Bio-Rad). The isolated RNA was processed via RT-PCR and the percent spliced in (PSI, ψ) (e.g., percent exon inclusion) for each minigene event upon protein or mock treatment was determined as previously described. The only differences from this previously published protocol was that for some RT steps SuperScript IV (Invitrogen) was utilized. Additionally, some samples were run out and the ψ values determined using a Fragment Analyzer (DNF-905 dsDNA 905 reagent kit, 1-500 bp, Advanced Analytical Technologies, Inc., Ankeny, Iowa) and associated ProSize data analysis software. No discernible differences in ψ quantification was observed between samples visualized using 6% native gels and SYBR green I nucleic acid stain (Invitrogen) and the Fragment Analyzer system. In the plasmid dosing system, ψ values were plotted against MBNL1 levels as determined by western plot relative to GAPDH and fit to a four-parameter dose-curve ($\psi=\psi_{min}+((\psi_{max}-\psi_{min})/(1+10^{((log(EC50)-log[MBNL1])*slope)})))$. Parameters that correlate to biological data, e.g., concentration ($EC_{50}$) and steepness of response (slope), were then derived from these curves.

Protein Expression and Purification

All proteins were expressed as N-terminal glutathione S-transferase (GST) fusions. Using BL21 Star (DE3) cells (Invitrogen), protein expression was induced using 0.5 mM IPTG at an $OD_{600}$=0.6-0.7 for 2 hours at 37° C. Following induction, cells were lysed in B-PER (bacterial protein extraction reagent) (Pierce, Rockford, Ill.) supplemented with DNase I (5 U/ml) and lysozyme (0.1 mg/ml) for 30 minutes at room temperature. The lysate was then diluted with 1 volume of 1×PBS and incubated for 30 minutes on ice prior to centrifugation at 17,000 rpm. The supernatant was isolated and mixed with glutathione agarose (Sigma-Aldrich) for 2 hours at 4° C. The resin was washed twice with 5 volumes of GST buffer (40 mM bicine pH 8.3, 50 mM NaCl), twice with 5 volumes of GST buffer supplemented with 1 M NaCl, and finally 3 times with 5 volumes of GST buffer—20 mM NaCl. GST-tagged proteins were then eluted with 10 mM glutathione in GST buffer—20 mM NaCl. The resulting elution was then concentrated and dialyzed into storage buffer (25 mM Tris pH 7.5, 500 mM NaCl, 5 mM β-mercaptoethanol (β-ME), 50% glycerol). Concentrations of the resulting proteins were determined via the Pierce 660 nM protein assay reagent using BSA standards.

RNA Radiolabeling and Electrophoretic Mobility Shift Assays (EMSAs)

All RNA substrates were ordered from IDT (Coralville, Iowa) or Dharmacon (Lafayette, Colo.) and 5' end-labelled using T4 PNK (NEB, Ipswich, Mass.) with [γ-³²P] ATP. All RNAs were purified on 10% polyacrylamide denaturing gels. Prior to incubation with protein, these RNAs were denatured by incubation at 95° C. for 2 minutes followed by a 5 minute incubation on ice. Once cooled the RNA was mixed with increasing concentrations of protein (final volume=10 µl) to yield final reaction conditions of 115 mM NaCl, 20 mM Tris pH 7.5, 1 mM β-ME, 0.01 mM EDTA, 10% glycerol, 5 mM $MgCl_2$, 0.1 mg/ml heparin, 2 mg/ml bovine serum albumin (BSA), and 0.02% xylene cyanol. This protein-RNA mixture was incubated for 30 minutes at room temperature for binding to reach equilibrium prior to electrophoresis. 3 l of the sample was then loaded on a pre-chilled, 1.5 mm, 6% native acrylamide (37.5:1) gel and run for 45 minutes at 150V at 4° C. Gels were dried for overnight exposure on phosphorus plates. Binding curves were quantified using ImageQuant software (GE Healthcare Life Sciences, Pittsburgh, Pa.). The fraction of RNA bound was calculated as the ratio of all RNA-protein complexes divided by total RNA signal in each lane. The apparent $K_d$ was then determined using the following equation: $f_{bound}=f_{max}([MBNL1]/([MBNL1+K_d]))$.

In Vitro Transcription of RNA Bind-n-Seq (RBNS) Random Input RNA

RBNS random input RNA was prepared by in vitro transcription using the RBNS T7 template (5'-ACACTCTTTCCCTACACGACGCTCTTCCGATCT(N)$_{40}$GATCGGAAGAGCACACGTCTG AACTCCAGT-CACCCTATAGTGAGTCGTATTA-3', SEQ ID NO: 41)), a DNA oligo containing a random 40mer sequence flanked by priming sites for the addition of Illumina (San Diego, Calif.) adaptors and the T7 promoter sequence. To artificially create a double-stranded T7 promoter, a T7 oligo (5'-TAATACGACTCACTATAGGG-3', SEQ ID NO: 42) was annealed to the region of the RBNS T7 template corresponding to the T7 promoter sequence by heating the template and T7 oligo in equal proportions up to 95° C. and cooling down at a rate of 0.1 C per second to 45° C. The RBNS input RNA pool was then in vitro transcribed using the HiScribe T7 in vitro transcription kit (NEB). The produced RNA was then bead purified using AMPure XP RNase free beads (Beckman Coulter Inc., Brea, Calif.).

RBNS and Computational Analysis

RBNS was performed using the same proteins purified as GST fusions for EMSAs. Eight concentrations of each MBNL1 protein (nM=0, 16, 32, 125, 250, 500, 1000, 2000), including a no MBNL condition, were equilibrated in binding buffer (25 mM Tris pH 7.5, 150 mM KCl, 3 mM MgCl$_2$, 0.01% Tween-20, 1 mg/ml BSA, 1 mM DTT, 30 µg/ml poly I/C (Sigma-Aldrich)) for 30 minutes at room temperature. In vitro transcribed RBNS random input RNA (see supplemental material for detailed experimental details) was then added to a final concentration of 1 µM with 40 U of SUPERase In (Ambion, Foster City, Calif.) and incubated for 1 hour at room temperature. During this incubation 50 µl aliquots of glutathione magnetic agarose beads (Pierce) were washed four times with 0.2 ml of wash buffer (25 mM Tris pH 7.5, 150 mM KCl, 60 µg/ml BSA, 0.5 mM EDTA, 0.01% Tween-20). The beads were then placed in 50 µl of binding buffer until needed. To pull down the tagged MBNL and interacting RNA, each RNA/protein solution was added to 15 µl of equilibrated and washed glutathione magnetic agarose beads (Pierce) and incubated for 1 hour at room temperature. Unbound RNA was removed by washing the beads 3 times with 0.2 ml of wash buffer. The beads were incubated at 70° C. for 10 minutes in 100 µl of elution buffer (10 mM Tris pH 7.0, 1 mM EDTA, 1% SDS) and the eluted material (bound RNA) collected with AMPure XP RNase-free beads (Beckman Coulter). The RNA was then reverse transcribed into cDNA using SuperScript IV (Invitrogen) according to the manufacturer's protocol with a common primer (5'-ACTGACCT-CAAGTCTGCACACGAGAAGGCTAG-3', SEQ ID NO: 43). 0.5 pmol of RBNS input RNA was also reverse transcribed to control for any nucleotide biases in the input library. Illumina sequencing libraries were prepared using primers with Illumina adaptors and unique sequencing barcodes (to allow for multiplexing all samples) to amplify the cDNA using Phusion high-fidelity DNA polymerase (NEB) for 16 amplification cycles. The list of primers used to index each sample library with unique barcodes are given in Table 1. All cDNA libraries were labelled with PEUniversal (5'-AATGATACGGCGACCACCGAGATCTA-CACTCTTTCCCTACACGACGCTCTTCCGATC T-3', SEQ ID NO: 44) and an index primer as listed in Table 1 to designate which protein at a specific concentration was utilized to isolate the bound RNA in the RBNS protocol. PCR products were bead purified using AMPure XP RNase-free beads (Beckman Coulter). Sequencing libraries corresponding to all concentrations of a given MBNL were pooled in a single lane and the random 40mer sequenced using the Illumina NextSeq 500. Motif (kmer) R values were calculated as the motif frequency in the selected RBP pool over the frequency in the input RNA library. Frequencies were controlled for the respective library read depth. The overall rate of kmer enrichment in the no protein condition relative to the input library was defined as the false-discovery rate (FDR). More detailed methods and theoretical assumptions utilized have been previously reported.

TABLE 1

Index primers used to identify each RBNS library within the multiplexed sequencing reads.

| Protein | Concentration [nM] | Index Primer | Sequences (5'→3') (SEQ ID NOs: 49-73) |
|---|---|---|---|
| WT-MBNL1 | 0 | PEIndex_8 | CAAGCAGAAGACGGCATACGAGAT CACTGT GTGACTGGAGTTCAGACGTGTGCTCTTCCGATC |
| WT-MBNL1 | 16 | PEIndex_7 | CAAGCAGAAGACGGCATACGAGAT ATTGGC GTGACTGGAGTTCAGACGTGTGCTCTTCCGATC |
| WT-MBNL1 | 32 | PEIndex_6 | CAAGCAGAAGACGGCATACGAGAT GATCTG GTGACTGGAGTTCAGACGTGTGCTCTTCCGATC |
| WT-MBNL1 | 125 | PEIndex_5 | CAAGCAGAAGACGGCATACGAGAT TCAAGT GTGACTGGAGTTCAGACGTGTGCTCTTCCGATC |
| WT-MBNL1 | 250 | PEIndex_4 | CAAGCAGAAGACGGCATACGAGAT CTGATC GTGACTGGAGTTCAGACGTGTGCTCTTCCGATC |
| WT-MBNL1 | 500 | PEIndex_3 | CAAGCAGAAGACGGCATACGAGAT AAGCTA GTGACTGGAGTTCAGACGTGTGCTCTTCCGATC |
| WT-MBNL1 | 1000 | PEIndex_2 | CAAGCAGAAGACGGCATACGAGAT GTAGCC GTGACTGGAGTTCAGACGTGTGCTCTTCCGATC |
| WT-MBNL1 | 2000 | PEIndex_1 | CAAGCAGAAGACGGCATACGAGAT TACAAG GTGACTGGAGTTCAGACGTGTGCTCTTCCGATC |

TABLE 1-continued

Index primers used to identify each RBNS library within the multiplexed sequencing reads.

| Protein | Concentration [nM] | Index Primer | Sequences (5'→3') (SEQ ID NOs: 49-73) |
|---|---|---|---|
| MBNL1(1-2,1-2) | 0 | PEIndex_16 | CAAGCAGAAGACGGCATACGAGAT GGACGG<br>GTGACTGGAGTTCAGACGTGTGCTCTTCCGATC |
| MBNL1(1-2,1-2) | 16 | PEIndex_15 | CAAGCAGAAGACGGCATACGAGAT TGACAT<br>GTGACTGGAGTTCAGACGTGTGCTCTTCCGATC |
| MBNL1(1-2,1-2) | 32 | PEIndex_14 | CAAGCAGAAGACGGCATACGAGAT GGAACT<br>GTGACTGGAGTTCAGACGTGTGCTCTTCCGATC |
| MBNL1(1-2,1-2) | 125 | PEIndex_13 | CAAGCAGAAGACGGCATACGAGAT TTGACT<br>GTGACTGGAGTTCAGACGTGTGCTCTTCCGATC |
| MBNL1(1-2,1-2) | 250 | PEIndex_12 | CAAGCAGAAGACGGCATACGAGAT CGTGAT<br>GTGACTGGAGTTCAGACGTGTGCTCTTCCGATC |
| MBNL1(1-2,1-2) | 500 | PEIndex_11 | CAAGCAGAAGACGGCATACGAGAT ACATCG<br>GTGACTGGAGTTCAGACGTGTGCTCTTCCGATC |
| MBNL1(1-2,1-2) | 1000 | PEIndex_10 | CAAGCAGAAGACGGCATACGAGAT GCCTAA<br>GTGACTGGAGTTCAGACGTGTGCTCTTCCGATC |
| MBNL1(1-2,1-2) | 2000 | PEIndex_9 | CAAGCAGAAGACGGCATACGAGAT TGGTCA<br>GTGACTGGAGTTCAGACGTGTGCTCTTCCGATC |
| MBNL1(3-4,3-4) | 0 | PEIndex_24 | CAAGCAGAAGACGGCATACGAGAT CTCTAC<br>GTGACTGGAGTTCAGACGTGTGCTCTTCCGATC |
| MBNL1(3-4,3-4) | 16 | PEIndex_23 | CAAGCAGAAGACGGCATACGAGAT GCGGAC<br>GTGACTGGAGTTCAGACGTGTGCTCTTCCGATC |
| MBNL1(3-4,3-4) | 32 | PEIndex_22 | CAAGCAGAAGACGGCATACGAGAT TTTCAC<br>GTGACTGGAGTTCAGACGTGTGCTCTTCCGATC |
| MBNL1(3-4,3-4) | 125 | PEIndex_21 | CAAGCAGAAGACGGCATACGAGAT GGCCAC<br>GTGACTGGAGTTCAGACGTGTGCTCTTCCGATC |
| MBNL1(3-4,3-4) | 250 | PEIndex_20 | CAAGCAGAAGACGGCATACGAGAT CGAAAC<br>GTGACTGGAGTTCAGACGTGTGCTCTTCCGATC |
| MBNL1(3-4,3-4) | 500 | PEIndex_19 | CAAGCAGAAGACGGCATACGAGAT CGTACG<br>GTGACTGGAGTTCAGACGTGTGCTCTTCCGATC |
| MBNL1(3-4,3-4) | 1000 | PEIndex_18 | CAAGCAGAAGACGGCATACGAGAT CCACTC<br>GTGACTGGAGTTCAGACGTGTGCTCTTCCGATC |
| MBNL1(3-4,3-4) | 2000 | PEIndex_17 | CAAGCAGAAGACGGCATACGAGAT GCTACC<br>GTGACTGGAGTTCAGACGTGTGCTCTTCCGATC |
| Input RNA | N/A | PEIndex_25 | CAAGCAGAAGACGGCATACGAGAT ATCAGT<br>GTGACTGGAGTTCAGACGTGTGCTCTTCCGATC |

Example 2: Engineering Synthetic MBNL1 Proteins for Efficient Cellular Uptake and Improvement of Binding to Toxic Repeat Domains One synthetic strategy focuses on production of "minimal" MBNL1 protein that could serve as a protein therapeutic in microsatellite diseases in which MBNL1 function is depleted. The creation of a small, high active MBNL1 that could be purified in vitro and delivered directly to cells and tissues upon treatment is a novel treatment strategy to treat these diseases.

One grouping of synthetic proteins that was engineered contains both human and *D. melanogaster* (mbl) ZF1-2 domains fused to cell-penetrating peptides (CPP). These CPPs are predicted to mediate cellular uptake and enhance RNA binding through electrostatic interactions. A schematic of ZF1-2-CPP fusion proteins are shown in FIG. 17A.

Another grouping of synthetic proteins that were engineered focuses on minimizing the size of both WT-MBNL1 and synthetic MBNL1 proteins by shortening the linker length between the tandem RNA binding domains. A schematic of MBNL1-Linkers are shown in FIG. 17B. The normal linker length is 76 aa (amino acids, labeled L76; this corresponds to the linker in both WT-MBNL1), the size of which was reduced to L57, L38, and L19 as labeled and shown in red.

Yet another synthetic strategy focuses on replacement of the ZF3-4 "general" RNA binding domain with other non-specific RNA binding domains (RBDs).

RNA binding proteins are built from modular domains that are combined in different ways to create a diverse array of functions. Some motifs are "specific" meaning that they have set RNA sequence requirements for binding; other domains are less specific, meaning that they have less sequence requirements for binding (Nat Rev Mol Cell Biol. 2007; 8(6):479-90). These modular domains can be combined in new ways to create proteins with new and/or improved functions by capitalizing on the function of various RNA binding domains. In other words, synthetic RBPs with new and improved functions can be developed through domain swapping.

MBNL1 serves an ideal platform for the development of new proteins to probe RNA processing and develop disease therapeutics for the following reasons:

1. Rearrangement of ZF domains does not eliminate MBNL1 function indicating that these domains are independent, modular units.
2. MBNL1 proteins are amenable to engineering, specifically "domain swapping."
3. As master regulators of RNA processing, MBNL1 serves as an ideal backbone for designing proteins to target these RNA processing mechanisms.
4. Synthetic MBNL1 proteins with increased activity could serve as therapeutics for various disease (e.g., DM, SCA8 or FECD).

Figures 18, 19A:
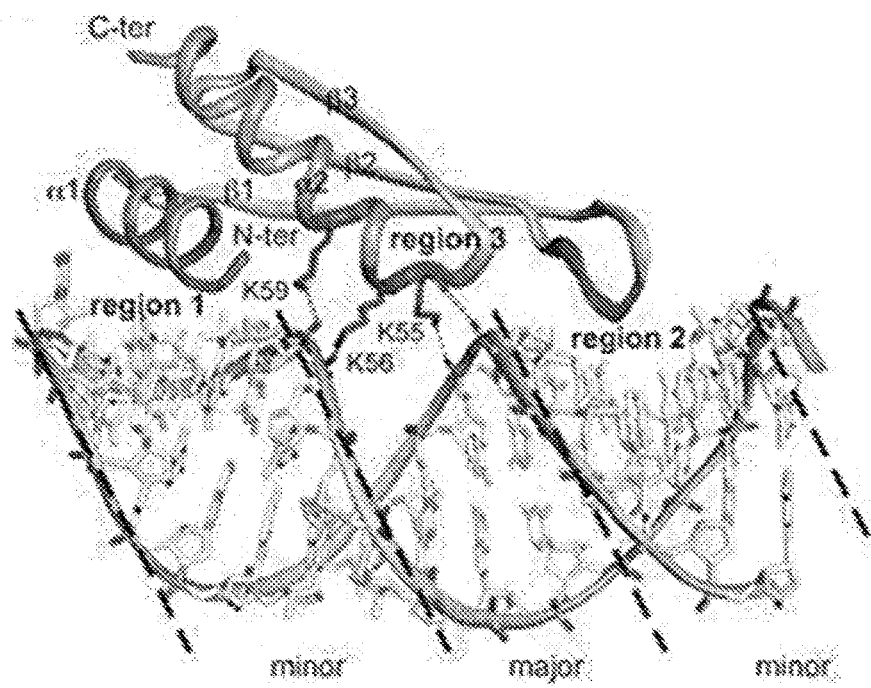
FIG. 18 shows affinity binding constants ($K_Ds$) for binding between WT-MBNL1, MBNL1(1-2,1-2) and MBNL1(3-4,3-4) synthetic proteins and endogenous targets or expanded CUG/CCUG repeats.
FIGS. 19A and 19B show the structure and interaction of a double stranded RNA binding domain (dsRBD) with RNA.

As shown in FIG. 18 (and FIG. 10C), MBNL proteins bind endogenous targets with higher affinity over expanded CUG/CCUG repeats. For example, WT-MBNL1 binds expanded repeat RNA with a 10-fold increase in KD as compared to single-stranded or endogenous RNA targets. We designed MBNL proteins that prefer expanded CUG/CCUG repeats over endogenous targets.

Figure 19B:
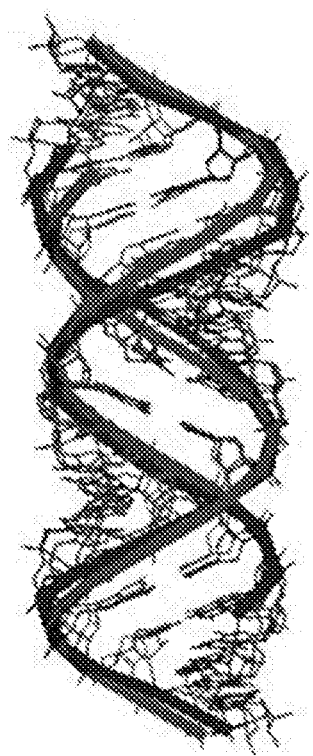

To create an MBNL1 protein with increased affinity for the repeats, MBNL1 ZF1-2 domain was fused with a dsRBD domain. Double stranded RNA binding domains (dsRBD) are 65-70 amino acid long domains with a conserved $\alpha\beta\beta\beta\alpha$ fold. They are highly abundant and found in eukaryotic, prokaryotic, and viral proteins with a wide variety of functions. These domains bind the minor groove of A-form double stranded RNA in a shape-dependent manner (FIG. 19A). It has been shown that a short $CUG_6$ repeat forms these A-form dsRNA structures in vitro (FIG. 19B). If the CUG repeats form this structure in cells, the fusion of a dsRBD domain and MBNL1 would preferentially bind the repeats by capitalizing on the preference of the ZF1-2 domain to bind to YGCY motifs (found in CUG and CCUG repeat RNA) and the dsRBD domain binding to A-form dsRNA.

A schematic of ZF1-2 non-specific RBD fusion proteins are shown in FIG. 17C. ZF3-4 domain was replaced with a dsRBD and the C-terminal region of MBNL1 was replaced with a HIV TAT (cell penetrating peptide, which also acts as a nuclear localization signal). Both Xlbpra and TRBP have low nanomolar affinity for structured RNAs. As an example, the $K_D$ for Xlbpra dsRBD2 binding to a 30 bp synthetic dsRNA is 11 nM. As an example, the $K_D$ for TRBP dsRBD2 binding to HIV TAR RNA hairpin is 59 nM. Xlbpra is involved in inhibition of translation and induction of apoptosis, contains three tandemly arranged dsRBDs and is a putative homologue of homo sapient protein TARBP2, is required for formation of RNA induced silencing complex (RISC), and also contains three tandemly arranged dsRBDs. The second dsRBD domains of each protein, Xlbpra and TRBP, were fused to the ZF1-2 domain.

Figure 20:
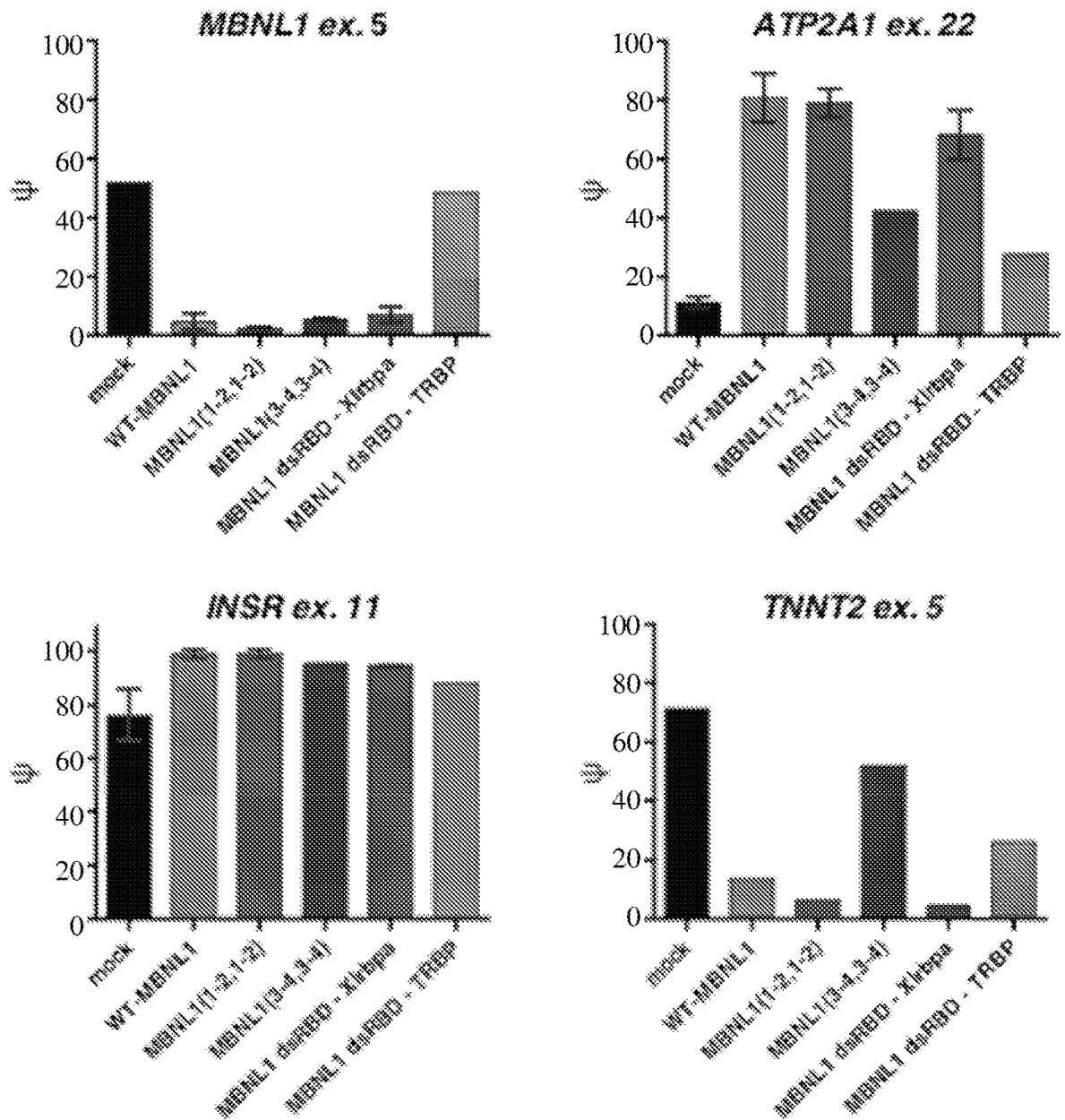
FIG. 20 shows splicing of minigene reporters in transfected HeLa cells by synthetic WT-MBNL1, MBNL1(1-2,1-2), MBNL1(3-4,3-4), and MBNL proteins with Xlrbpa and TRBP dsRBDs.

FIG. 20 shows splicing data for MBNL1-dsRBD constructs in comparison to WT-MBNL1, MBNL1(1-2,1-2), and MBNL1(3-4,3-4). Assays were performed by transfecting HeLa cells with a minigene reporter and an expression plasmid for each synthetic construct. "Mock" represents transfection of an empty vector with no MBNL1 protein. MBNL1 dsRBD-TRBP has very weak splicing activity, while the MBNL1 dsRBD Xlrbpa has relatively high activity, in some cases comparable to MBNL1(1-2,1-2). This data does not take into account protein expression levels. MBNL1 dsRBD Xlrbpa could preferentially bind structured RNAs, like expanded CUG/CCUG repeats and therefore be used to displace sequestered endogenous MBNL for expanded repeats.

RDBs can include RGG boxes (arginine-glycine rich domains) and double-stranded RNA binding domains (dsRBDs). RGG boxes act as non-specific RBDs in many proteins throughout the human genome, including hnRNP U. dsRBDs bind double-stranded RNA in a sequence independent manner. Fusion of dsRBDs from (examples here include human TRBP and *Xenopus laevis* Xlbpra) could improve targeting of MBNL1 to the toxic CUG/CCUG repeat RNA expressed in DM1 and DM2. These RNAs are predicted to form double-stranded RNA structures in the cell. Targeting of a ZF1-2-dsRBD fusion to the repeat RNA could displace endogenous MBNL1 in patient cells.

Figure 22A:
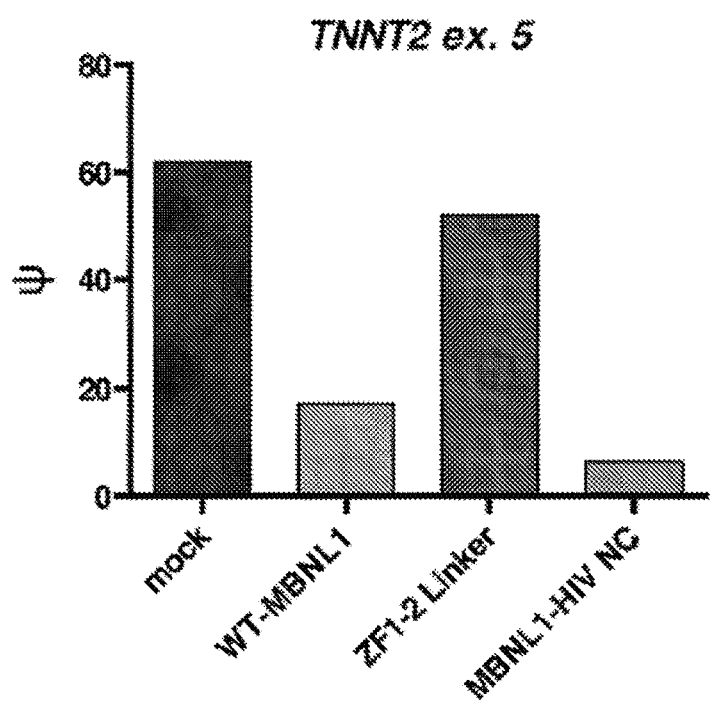
FIGS. 22A-22B show that MBNL1-HIV NC regulates a pre-mRNA substrate that contains a structural element.
Figure 22B:
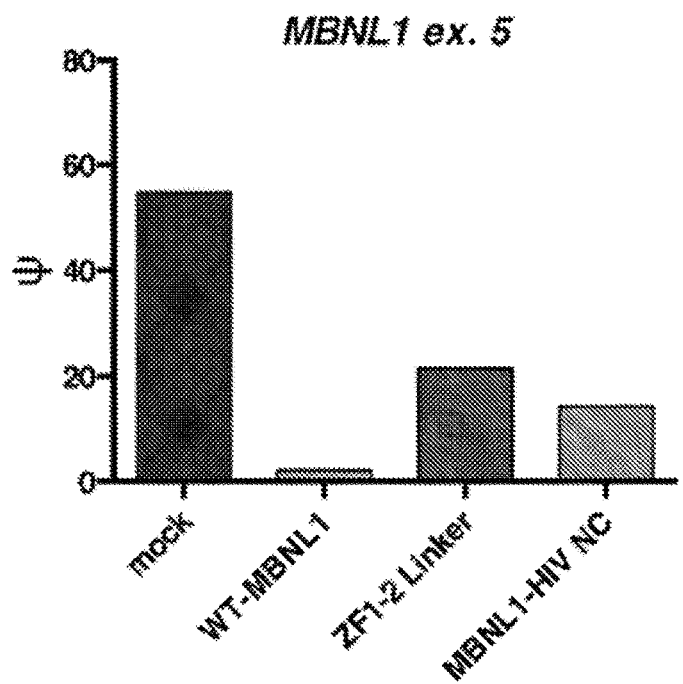

Experiments were also conducted using an HIV NC domain added to MBNL1 to test if this low specificity RNA binding domain could replace MBNL1 ZF3-4 and more importantly determine if the RNA chaperone activity of this domain could affect the splicing responses of pre-mRNAs predicted to be highly structured and facilitate folding of CUG repeats into the lowest energy structural conformation. HIV NC has been shown to act as an RNA chaperone to increase the rate of HIV RNA folding into the lowest free energy structures for the viral life cycle. More broadly, HIV NC has been shown to chaperone the folding of RNA enzymes and facilitate nucleic acid strand exchange reactions. FIGS. 22A and 22B show data for two splicing reporters with MBNL1-HIV NC, and imply that this protein is more active than MBNL1 containing ZF1-2 and the linker. For the structured TNNT2 exon 5 RNA substrate, MBNL1-HIV NC has better splicing activity than WT-MBNL1 (FIG. 22A). For MBNL1 exon 5 (auto-regulation) with minimal structure in the regulatory region, WT-MBNL1 has higher activity than MBNL1-HIV NC (FIG. 22B). At this single high plasmid concentration with these two pre-mRNAs, the results suggest that MBNL1-HIV NC has higher activity for structured pre-mRNAs than WT-MBNL1. Dosing using a plasmid system can be used to determine how this synthetic protein compares to WT-MBNL1 and other synthetic proteins.

Figure 23:
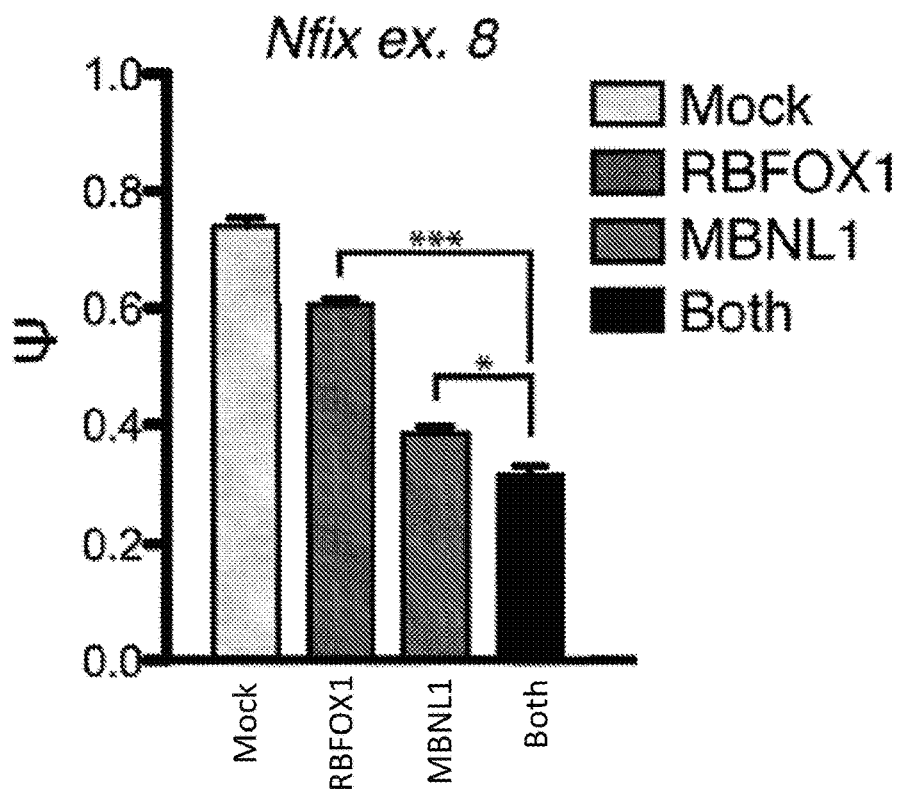
FIG. 23 shows an example of co-regulated splicing by MBNL1 and RBFOX1. The splicing reporter derived from the mouse Nfix gene (exon 8 is alternatively spliced) is skipped most when both factors are present.

203 Mbnl-regulated exons from mouse RNAseq data were analyzed and it was found that 33% contained one or more UGCAUG RBFOX motifs in the exon or 250 nucleotides of flanking introns. This overlap suggested that MBNL and RBFOX protein families co-regulate many splicing events. The synthetic MBNL1-RBFOX protein (FIG. 21) is predicted to bind both YGCY motifs and UGCAUG motifs via ZF1-2 of MBNL1 and the RRM of RBFOX, respectively. To assess if MBNL1-RBFOX is a functional synthetic protein, it was expressed in HeLa cells with a splicing reporter regulated by both proteins (FIG. 23). It was found that the splicing reporter derived from the mouse Nfix gene (exon 8 is alternatively spliced) is skipped most when both factors are present.

Figure 24A:
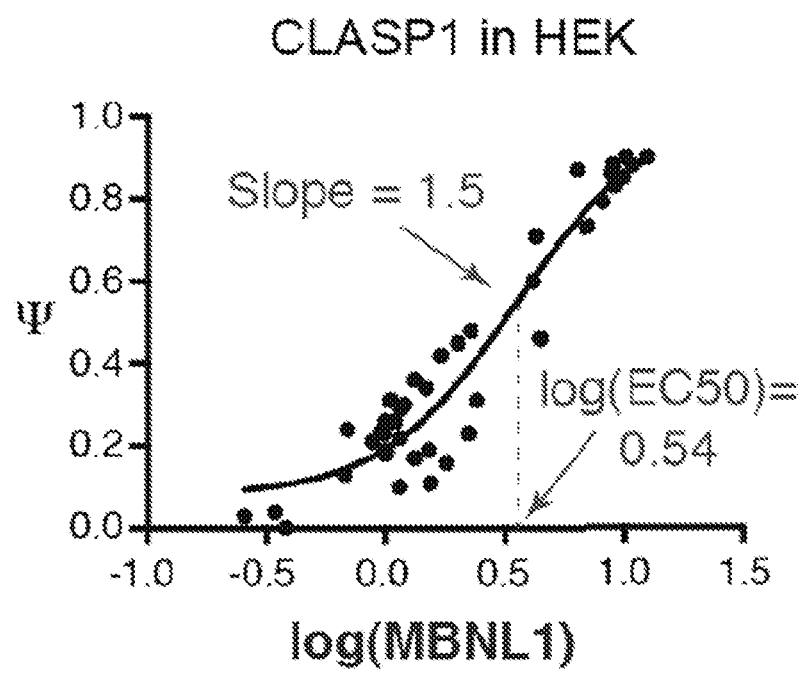
FIGS. 24A-24C show dose response curves of endogenous events in the MBNL1 inducible HEK293 and MEF cell lines.
Figure 24B:
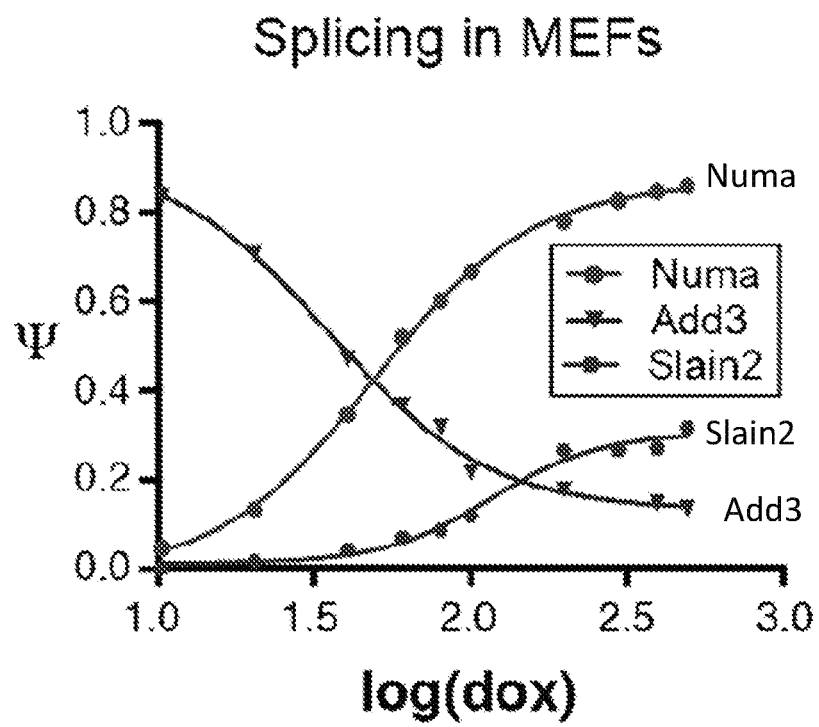
Figure 24C:
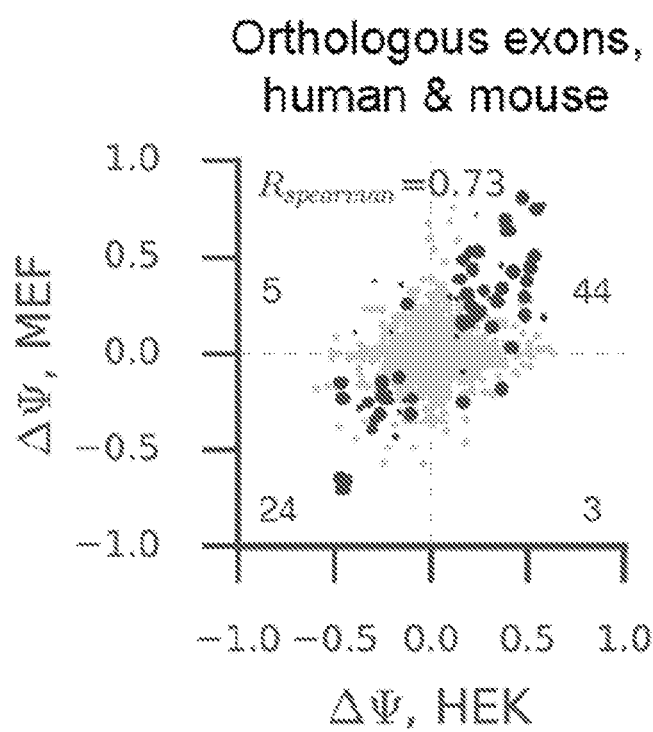

Stable cell lines that provide inducible control of synthetic MBNL1 proteins were developed. To complement the HEK dosing cell line we have recently generated an MBNL1 dosing cell line from mouse embryonic fibroblast (MEF) cells lacking MBNL1 and MBNL2. This immortalized cell line was derived from the MBNL1/2 DKO mouse. Studies revealed a range of splicing responses to MBNL1 protein concentration; parameters for $EC_{50}$ (concentration at which 50% splicing change has occurred) and slope were derived by curve-fitting to Ψ across a range of MBNL1 concentrations (FIG. 24A). Over the MBNL1 gradient in the HEK293 system this regulated event changes from skipped to almost fully included, the dosing curve parameters (EC50 and slope) reveal that this event requires a median level of MBNL1 and has a modest degree of cooperativity. The MEF MBNL1 cell line has dosing curves that are similar to those in our published HEK293 system. Several events misspliced in the $HAS_{LR}$ DM1 mouse model are regulated in the expected direction with increasing levels of MBNL1, (fetal to adult transition) and display a range of dosing curves (FIG. 24B). To compare the HEK293 and MEF dosing cell lines directly, RNAseq at no dox and high dox for the two cell lines was perfored. The RNAseq data showed that 68 orthologous events (cassette exons) have the same or similar changes in splicing (FIG. 24C), indicating conserved regulation in these different cellular backgrounds. The prediction is that these events will be highly conserved at the sequence and RNA structural level between mouse and human (ongoing analysis), and events that differ between the two systems are less conserved or lack conservation or are regulated differently due to the differences between the cell lines such as lower or higher levels of other splicing factors.

REFERENCES

1. Kalsotra, A. and Cooper, T. A. (2011) Functional consequences of developmentally regulated alternative splicing. Nat. Rev. Genet., 12, 715-729.
2. Wang, E. T., Sandberg, R., Luo, S., Khrebtukova, I., Zhang, L., Mayr, C., Kingsmore, S. F., Schroth, G. P. and Burge, C. B. (2008) Alternative isoform regulation in human tissue transcriptomes. Nature, 456, 470-476.
3. Pan, Q., Shai, O., Lee, L. J., Frey, B. J. and Blencowe, B. J. (2008) Deep surveying of alternative splicing complexity in the human transcriptome by high-throughput sequencing. Nat. Genet., 40, 1413-1415.
4. Fu, X.-D. and Ares, M. (2014) Context-dependent control of alternative splicing by RNA-binding proteins. Nat. Rev. Genet., 15, 689-701.
5. Jangi, M. and Sharp, P. A. (2014) Building robust transcriptomes with master splicing factors. CELL, 159, 487-498.
6. Pascual, M., Vicente, M., Monferrer, L. and Artero, R. (2006) The Muscleblind family of proteins: an emerging class of regulators of developmentally programmed alternative splicing. Differentiation, 74, 65-80.
7. Fernandez-Costa, J. M., Llamusi, M. B., Garcia-Lopez, A. and Artero, R. (2011) Alternative splicing regulation by Muscleblind proteins: from development to disease. Biological Reviews, 86, 947-958.
8. Lin, X., Miller, J. W., Mankodi, A., Kanadia, R. N., Yuan, Y., Moxley, R. T., Swanson, M. S. and Thornton, C. A. (2006) Failure of MBNL1-dependent post-natal splicing transitions in myotonic dystrophy. Human Molecular Genetics, 15, 2087-2097.
9. Kalsotra, A., Xiao, X., Ward, A. J., Castle, J. C., Johnson, J. M., Burge, C. B. and Cooper, T. A. (2008) A postnatal switch of CELF and MBNL proteins reprograms alternative splicing in the developing heart. Proc. Natl. Acad. Sci. U.S.A., 105, 20333-20338.
10. Dixon, D. M., Choi, J., El-Ghazali, A., Park, S. Y., Roos, K. P., Jordan, M. C., Fishbein, M. C., Comai, L. and Reddy, S. (2015) Loss of muscleblind-like 1 results in cardiac pathology and persistence of embryonic splice isoforms. Sci. Rep., 5, 9042.
11. Wang, E. T., Ward, A. J., Cherone, J. M., Giudice, J., Wang, T. T., Treacy, D. J., Lambert, N. J., Freese, P., Saxena, T., Cooper, T. A., et al. (2015) Antagonistic regulation of mRNA expression and splicing by CELF and MBNL proteins. Genome Res., 25, 858-871.
12. Blech-Hermoni, Y. and Ladd, A. N. (2013) RNA binding proteins in the regulation of heart development. Int. J. Biochem. Cell Biol., 45, 2467-2478.
13. Wang, E. T., Cody, N. A. L., Jog, S., Biancolella, M., Wang, T. T., Treacy, D. J., Luo, S., Schroth, G. P., Housman, D. E., Reddy, S., et al. (2012) Transcriptome-wide Regulationof Pre-mRNA Splicing and mRNA Localization by Muscleblind Proteins. CELL, 150, 710-724.
14. Masuda, A., Andersen, H. S., Doktor, T. K., Okamoto, T., Ito, M., Andresen, B. S. and Ohno, K. (2012) CUGBP1 and MBNL1 preferentially bind to 3' UTRs and facilitate mRNA decay. Sci. Rep., 2.
15. Osborne, R. J., Lin, X., Welle, S., Sobczak, K., O'Rourke, J. R., Swanson, M. S. and Thornton, C. A. (2009) Transcriptional and post-transcriptional impact of toxic RNA in myotonic dystrophy. Human Molecular Genetics, 18, 1471-1481.
16. Du, H., Cline, M. S., Osborne, R. J., Tuttle, D. L., Clark, T. A., Donohue, J. P., Hall, M. P., Shiue, L., Swanson, M. S., Thornton, C. A., et al. (2010) Aberrant alternative splicing and extracellular matrix gene expression in mouse models of myotonic dystrophy. Nature Structural & Molecular Biology, 17, 187-193.
17. Batra, R., Charizanis, K., Manchanda, M., Mohan, A., Li, M., Finn, D. J., Goodwin, M., Zhang, C., Sobczak, K., Thornton, C. A., et al. (2014) Loss of MBNL leads to disruption of developmentally regulated alternative polyadenylation in RNA-mediated disease. Molecular Cell, 56, 311-322.
18. Rau, F., Freyermuth, F., Fugier, C., Villemin, J.-P., Fischer, M.-C., Jost, B., Dembele, D., Gourdon, G., Nicole, A., Duboc, D., et al. (2011) Misregulation of miR-1 processing is associated with heart defects in myotonic dystrophy. Nature Structural & Molecular Biology, 18, 840-845.
19. Brook, J. D., McCurrach, M. E., Harley, H. G., Buckler, A. J., Church, D., Aburatani, H., Hunter, K., Stanton, V. P., Thirion, J. P. and Hudson, T. (1992) Molecular basis of myotonic dystrophy: expansion of a trinucleotide (CTG) repeat at the 3' end of a transcript encoding a protein kinase family member. CELL, 68, 799-808.
20. Liquori, C. L., Ricker, K., Moseley, M. L., Jacobsen, J. F., Kress, W., Naylor, S. L., Day, J. W. and Ranum, L. P. (2001) Myotonic dystrophy type 2 caused by a CCTG expansion in intron 1 of ZNF9. Science, 293, 864-867.
21. Fardaei, M., Rogers, M. T., Thorpe, H. M., Larkin, K., Hamshere, M. G., Harper, P. S. and Brook, J. D. (2002) Three proteins, MBNL, MBLL and MBXL, co-localize in vivo with nuclear foci of expanded-repeat transcripts in DM1 and DM2 cells. Human Molecular Genetics, 11, 805-814.
22. Fardaei, M., Larkin, K., Brook, J. D. and Hamshere, M. G. (2001) In vivo co-localisation of MBNL protein with DMPK expanded-repeat transcripts. Nucleic Acids Research, 29, 2766-2771.
23. Mankodi, A., Urbinati, C. R., Yuan, Q. P., Moxley, R. T., Sansone, V., Krym, M., Henderson, D., Schalling, M., Swanson, M. S. and Thornton, C. A. (2001) Muscleblind localizes to nuclear foci of aberrant RNA in myotonic dystrophy types 1 and 2. Human Molecular Genetics, 10, 2165-2170.
24. Lee, J. E. and Cooper, T. A. (2009) Pathogenic mechanisms of myotonic dystrophy. Biochem. Soc. Trans, 37, 1281-1286.
25. Klein, A. F., Gasnier, E. and Furling, D. (2013) Gain of RNA function in pathological cases: Focus on myotonic dystrophy. Biochimie, 10.1016/j.biochi.2011.06.028.
26. Chau, A. and Kalsotra, A. (2015) Developmental insights into the pathology of and therapeutic strategies for DM1: Back to the basics. Dev. Dyn., 244, 377-390.
27. Meola, G. and Cardani, R. (2015) Myotonic dystrophies: An update on clinical aspects, genetic, pathology, and molecular pathomechanisms. Biochim. Biophys. Acta, 1852, 594-606.
28. Daughters, R. S., Tuttle, D. L., Gao, W., Ikeda, Y., Moseley, M. L., Ebner, T. J., Swanson, M. S. and Ranum, L. P. W. (2009) RNA gain-of-function in spinocerebellar ataxia type 8. PLoS Genet., 5, e1000600.

29. Du, J., Aleff, R. A., Soragni, E., Kalari, K., Nie, J., Tang, X., Davila, J., Kocher, J.-P., Patel, S. V., Gottesfeld, J. M., et al. (2015) RNA toxicity and missplicing in the common eye disease fuchs endothelial corneal dystrophy. Journal of Biological Chemistry, 290, 5979-5990.
30. Purcell, J., Oddo, J. C., Wang, E. T. and Berglund, J. A. (2012) Combinatorial Mutagenesis of MBNL1 Zinc Fingers Elucidates Distinct Classes of Regulatory Events. Molecular and Cellular Biology, 32, 4155-4167.
31. Goers, E. S., Purcell, J., Voelker, R. B., Gates, D. P. and Berglund, J. A. (2010) MBNL1 binds GC motifs embedded in pyrimidines to regulate alternative splicing. Nucleic Acids Research, 38, 2467-2484.
32. Teplova, M. and Patel, D. J. (2008) Structural insights into RNA recognition by the alternative-splicing regulator muscleblind-like MBNL1. Nature Structural & Molecular Biology, 15, 1343-1351.
33. Cass, D., Hotchko, R., Barber, P., Jones, K., Gates, D. P. and Berglund, J. A. (2011) The four Zn fingers of MBNL1 provide a flexibleplatform for recognition of its RNA bindingelements. BMC Molecular Biology, 12, 20.
34. Ho, T. H., Charlet-B, N., Poulos, M. G., Singh, G., Swanson, M. S. and Cooper, T. A. (2004) Muscleblind proteins regulate alternative splicing. EMBO J., 23, 3103-3112.
35. Lambert, N., Robertson, A., Jangi, M., McGeary, S., Sharp, P. A. and Burge, C. B. (2014) RNA Bind-n-Seq: quantitative assessment of the sequence and structural binding specificity of RNA binding proteins. Molecular Cell, 54, 887-900.
36. Irion, U. (2012) Drosophila muscleblind codes for proteins with one and two tandem zinc finger motifs. PLoS ONE, 7, e34248.
37. Oddo, J. C., Saxena, T., McConnell, O. L., Berglund, J. A. and Wang, E. T. (2016) Conservation of context-dependent splicing activity in distant Muscleblind homologs. Nucleic Acids Research, 44, 8352-8362.
38. Vicente-Crespo, M., Pascual, M., Fernandez-Costa, J. M., Garcia-Lopez, A., Monferrer, L., Miranda, M. E., Zhou, L. and Artero, R. D. (2008) Drosophila muscleblind is involved in troponin T alternative splicing and apoptosis. PLoS ONE, 3, e1613.
39. Grammatikakis, I., Goo, Y. H., Echeverria, G. V. and Cooper, T. A. (2011) Identification of MBNL1 and MBNL3 domains required for splicing activation and repression. Nucleic Acids Research, 39, 2769-2780.
40. Tran, H., Gourrier, N., Lemercier-Neuillet, C., Dhaenens, C. M., Vautrin, A., Fernandez-Gomez, F. J., Arandel, L., Carpentier, C., Obriot, H., Eddarkaoui, S., et al. (2011) Analysis of Exonic Regions Involved in Nuclear Localization, Splicing Activity, and Dimerization of Muscleblind-like-1 Isoforms. Journal of Biological Chemistry, 286, 16435-16446.
41. Warf, M. B. and Berglund, J. A. (2007) MBNL binds similar RNA structures in the CUG repeats of myotonic dystrophy and its pre-mRNA substrate cardiac troponin T. RNA, 13, 2238-2251.
42. Edge, C., Gooding, C. and Smith, C. W. (2013) Dissecting domains necessary for activation and repression of splicing by muscleblind-like protein 1. BMC Molecular Biology, 14, 29.
43. Kosaki, A., Nelson, J. and Webster, N. J. (1998) Identification of intron and exon sequences involved in alternative splicing of insulin receptor pre-mRNA. J. Biol. Chem., 273, 10331-10337.
44. Sen, S., Talukdar, I., Liu, Y., Tam, J., Reddy, S. and Webster, N. J. G. (2010) Muscleblind-like 1 (Mbnll) Promotes Insulin Receptor Exon 11 Inclusion via Binding to a Downstream Evolutionarily Conserved Intronic Enhancer. Journal of Biological Chemistry, 285, 25426-25437.
45. Hino, S.-I., Kondo, S., Sekiya, H., Saito, A., Kanemoto, S., Murakami, T., Chihara, K., Aoki, Y., Nakamori, M., Takahashi, M. P., et al. (2007) Molecular mechanisms responsible for aberrant splicing of SERCA1 in myotonic dystrophy type 1. Human Molecular Genetics, 16, 2834-2843.
46. Gates, D. P., Coonrod, L. A. and Berglund, J. A. (2011) Autoregulated splicing of muscleblind-like 1 (MBNL1) Pre-mRNA. Journal of Biological Chemistry, 286, 34224-34233.
47. Wagner, S. D., Struck, A. J., Gupta, R., Farnsworth, D. R., Mahady, A. E., Eichinger, K., Thornton, C. A., Wang, E. T. and Berglund, J. A. (2016) Dose-Dependent Regulation of Alternative Splicing by MBNL Proteins Reveals Biomarkers for Myotonic Dystrophy. PLoS Genet., 12, e1006316.
48. Fu, Y., Ramisetty, S. R., Hussain, N. and Baranger, A. M. (2011) MBNL1-RNA Recognition: Contributions of MBNL1 Sequence and RNA Conformation. ChemBioChem, 13, 112-119.
49. Lunde, B. M., Moore, C. and Varani, G. (2007) RNA-binding proteins: modular design for efficient function. Nat Rev Mol Cell Biol, 8, 479-490.
50. Murn, J., Teplova, M., Zarnack, K., Shi, Y. and Patel, D. J. (2016) Recognition of distinct RNA motifs by the clustered CCCH zinc fingers of neuronal protein Unkempt. Nature Structural & Molecular Biology, 23, 16-23.
51. Murn, J., Zarnack, K., Yang, Y. J., Durak, O., Murphy, E. A., Cheloufi, S., Gonzalez, D. M., Teplova, M., Curk, T., Zuber, J., et al. (2015) Control of a neuronal morphology program by an RNA-binding zinc finger protein, Unkempt. Genes Dev., 29, 501-512.
52. Mackay, J. P., Font, J. and Segal, D. J. (2011) The prospects for designer single-stranded RNA-binding proteins. Nature Structural & Molecular Biology, 18, 256-261.
53. Chen, Y. and Varani, G. (2013) Engineering RNA-binding proteins for biology. FEBS J., 280, 3734-3754.
54. Kanadia, R. N., Shin, J., Yuan, Y., Beattie, S. G., Wheeler, T. M., Thornton, C. A. and Swanson, M. S. (2006) Reversal of RNA missplicing and myotonia after muscleblind overexpression in a mouse poly(CUG) model for myotonic dystrophy. Proc. Natl. Acad. Sci. U.S.A., 103, 11748-11753.
55. Chamberlain, C. M. and Ranum, L. P. W. (2012) Mouse model of muscleblind-like 1 overexpression: skeletal muscle effects and therapeutic promise. Human Molecular Genetics, 21, 4645-4654.
56. Edgar, R. C. (2004) MUSCLE: multiple sequence alignment with high accuracy and high throughput. Nucleic Acids Research, 32, 1792-1797.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary or examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A composition comprising a synthetic MBNL1 (Muscleblind-like protein 1) protein, wherein the synthetic MBNL1 protein comprises:
   a first zinc finger (ZF) domain comprising a first ZF motif and a second ZF motif,
   a second ZF domain comprising a third ZF motif and a fourth ZF motif, and nuclear localization signal (NLS);
   wherein the first ZF domain is linked to the second ZF domain by a linker, wherein the amino acid sequence of the first zinc finger domain is the same as the amino acid sequence of the second zinc finger domain; and
   wherein the first ZF domain is positioned towards the N-terminal of the synthetic MBNL1 protein relative to the second ZF domain wherein the amino acid sequence of the first ZF domain is SEQ ID NO: 1 or has at least 80% sequence identity to SEQ ID NO: 1 and the amino acid sequence of the second ZF domain is SEQ ID NO: 1 or has at least 80% sequence identity to SEQ ID NO: 1; or the amino acid sequence of the first ZF domain is SEQ ID NO: 2 or has at least 80% sequence identity to SEQ ID NO: 2 and the amino acid sequence of the second ZF domain is SEQ ID NO: 2 or has at least 80% sequence identity to SEQ ID NO: 2.

2. The composition of claim 1, wherein the synthetic MBNL1 protein is truncated at the C-terminus by 1-122 amino acids.

3. The composition of claim 1, wherein the amino acid sequence of the linker is selected from the group consisting of: SEQ ID NO: 4, SEQ ID NO: 12, SEQ ID NO: 13, and SEQ ID NO: 14, or has at least 80% sequence identity to a sequence selected from the group consisting of: SEQ ID NO: 4, SEQ ID NO: 12, SEQ ID NO: 13, and SEQ ID NO: 14.

4. The composition of claim 1, wherein the synthetic MBNL1 protein is fused to a targeting moiety.

5. The composition of claim 4, wherein the targeting moiety is selected from the group consisting of: a cell penetrating peptide (CPP), an RNA binding domain (RBD), a cell surface receptor binding ligand, a cell penetrating antibody, a mutant cell penetrating antibody, and a cell-penetrating antibody fragment.

6. The composition of claim 5, wherein the CPP is HIV-TAT or 8x Arginine, and wherein the RBD is a RGG box, a double-stranded RNA binding domain (dsRBD), a RBFOX, a RS or a HIV nucleocapsid (HIV NC) domain.

7. The composition of claim 1, wherein the composition comprises a pharmaceutically acceptable carrier, a liposome, a lipid, or a lipid complex.

8. A composition comprising a synthetic MBNL1 protein, wherein the synthetic MBNL1 protein comprises:
   a first zinc finger (ZF) domain comprising a first ZF motif and a second ZF motif, a second ZF domain comprising a third ZF motif and a fourth ZF motif, and a cell penetrating peptide (CPP), or an RNA binding domain (RBD);
   wherein the first ZF domain is linked to the CPP or RBD by a linker sequence that is truncated relative to a wild-type MBNL1 linker sequence;
   wherein the amino acid sequence of the first zinc finger domain is the same as the amino acid sequence of the second zinc finger domain;
   and wherein the amino acid sequence of the first ZF domain is SEQ ID NO: 1 or has at least 80% sequence identity to SEQ ID NO: 1 and the amino acid sequence of the second ZF domain is SEQ ID NO: 1 or has at least 80% sequence identity to SEQ ID NO: 1; or the amino acid sequence of the first ZF domain is SEQ ID NO: 2 or has at least 80% sequence identity to SEQ ID NO: 2 and the amino acid sequence of the second ZF domain is SEQ ID NO: 2 or has at least 80% sequence identity to SEQ ID NO: 2.

9. The composition of claim 8, wherein the synthetic MBNL1 protein further comprises a NLS.

10. The composition of claim 8, wherein the synthetic MBNL1 protein comprises both the CPP and RBD.

11. The composition of claim 8, wherein the amino acid sequence of the linker is selected from the group consisting of: SEQ ID NO: 12, SEQ ID NO: 13, and SEQ ID NO: 14, or has at least 80% sequence identity to a sequence selected from the group consisting of: SEQ ID NO: 12, SEQ ID NO: 13, and SEQ ID NO: 14.

12. The composition of claim 8, wherein the synthetic MBNL1 protein is fused to a targeting moiety.

13. The composition of claim 12, wherein the targeting moiety is selected from the group consisting of: a cell penetrating peptide (CPP), an RNA binding domain (RBD), a cell surface receptor binding ligand, a cell penetrating antibody, a mutant cell penetrating antibody, and a cell-penetrating antibody fragment.

14. The composition of claim 13, wherein the CPP is HIV-TAT or 8× Arginine, and wherein the RBD is a RGG box, a double-stranded RNA binding domain (dsRBD), a RBFOX, a RS or a HIV nucleocapsid (HIV NC) domain.

15. The composition of claim 8, wherein the composition comprises a pharmaceutically acceptable carrier, a liposome, a lipid, or a lipid complex.

\* \* \* \* \*

SEQUENCE LISTING

```
<160> NUMBER OF SEQ ID NOS: 92

<210> SEQ ID NO 1
<211> LENGTH: 93
<212> TYPE: PRT
<213> ORGANISM: Artificial Sequence
<220> FEATURE:
<223> OTHER INFORMATION: Synthetic Polypeptide
```

<400> SEQUENCE: 1

Arg Asp Thr Lys Trp Leu Thr Leu Glu Val Cys Arg Glu Phe Gln Arg
1               5                   10                  15

Gly Thr Cys Ser Arg Pro Asp Thr Glu Cys Lys Phe Ala His Pro Ser
            20                  25                  30

Lys Ser Cys Gln Val Glu Asn Gly Arg Val Ile Ala Cys Phe Asp Ser
        35                  40                  45

Leu Lys Gly Arg Cys Ser Arg Glu Asn Cys Lys Tyr Leu His Pro Pro
    50                  55                  60

Pro His Leu Lys Thr Gln Leu Glu Ile Asn Gly Arg Asn Asn Leu Ile
65                  70                  75                  80

Gln Gln Lys Asn Met Ala Met Leu Ala Gln Gln Met Gln
                85                  90

<210> SEQ ID NO 2
<211> LENGTH: 76
<212> TYPE: PRT
<213> ORGANISM: Artificial Sequence
<220> FEATURE:
<223> OTHER INFORMATION: Synthetic Polypeptide

<400> SEQUENCE: 2

Arg Thr Asp Arg Leu Glu Val Cys Arg Glu Tyr Gln Arg Gly Asn Cys
1               5                   10                  15

Asn Arg Gly Glu Asn Asp Cys Arg Phe Ala His Pro Ala Asp Ser Thr
            20                  25                  30

Met Ile Asp Thr Asn Asp Asn Thr Val Thr Val Cys Met Asp Tyr Ile
        35                  40                  45

Lys Gly Arg Cys Ser Arg Glu Lys Cys Lys Tyr Phe His Pro Pro Ala
    50                  55                  60

His Leu Gln Ala Lys Ile Lys Ala Ala Gln Tyr Gln
65                  70                  75

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

Pro Lys Lys Lys Arg Lys Val Glu
1               5

<210> SEQ ID NO 4
<211> LENGTH: 76
<212> TYPE: PRT
<213> ORGANISM: Artificial Sequence
<220> FEATURE:
<223> OTHER INFORMATION: Synthetic Polypeptide

<400> SEQUENCE: 4

Leu Ala Asn Ala Met Met Pro Gly Ala Pro Leu Gln Pro Val Pro Met
1               5                   10                  15

Phe Ser Val Ala Pro Ser Leu Ala Thr Asn Ala Ser Ala Ala Ala Phe
            20                  25                  30

Asn Pro Tyr Leu Gly Pro Val Ser Pro Ser Leu Val Pro Ala Glu Ile
        35                  40                  45

Leu Pro Thr Ala Pro Met Leu Val Thr Gly Asn Pro Gly Val Pro Val

```
                    50                  55                  60
Pro Ala Ala Ala Ala Ala Ala Gln Lys Leu Met
 65                  70                  75

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 5

Tyr Pro Tyr Asp Val Pro Asp Tyr Ala
 1               5

<210> SEQ ID NO 6
<211> LENGTH: 280
<212> TYPE: PRT
<213> ORGANISM: Artificial Sequence
<220> FEATURE:
<223> OTHER INFORMATION: Synthetic Polypeptide

<400> SEQUENCE: 6

Met Glu Tyr Pro Tyr Asp Val Pro Asp Tyr Ala Gly Ser Ala Val Ser
 1               5                  10                  15

Val Thr Pro Ile Arg Asp Thr Lys Trp Leu Thr Leu Glu Val Cys Arg
                20                  25                  30

Glu Phe Gln Arg Gly Thr Cys Ser Arg Pro Asp Thr Glu Cys Lys Phe
            35                  40                  45

Ala His Pro Ser Lys Ser Cys Gln Val Glu Asn Gly Arg Val Ile Ala
        50                  55                  60

Cys Phe Asp Ser Leu Lys Gly Arg Cys Ser Arg Glu Asn Cys Lys Tyr
 65                  70                  75                  80

Leu His Pro Pro His Leu Lys Thr Gln Leu Glu Ile Asn Gly Arg
                85                  90                  95

Asn Asn Leu Ile Gln Gln Lys Asn Met Ala Met Leu Ala Gln Gln Met
                100                 105                 110

Gln Leu Ala Asn Ala Met Met Pro Gly Ala Pro Leu Gln Pro Val Pro
            115                 120                 125

Met Phe Ser Val Ala Pro Ser Leu Ala Thr Asn Ala Ser Ala Ala Ala
        130                 135                 140

Phe Asn Pro Tyr Leu Gly Pro Val Ser Pro Ser Leu Val Pro Ala Glu
145                 150                 155                 160

Ile Leu Pro Thr Ala Pro Met Leu Val Thr Gly Asn Pro Gly Val Pro
                165                 170                 175

Val Pro Ala Ala Ala Ala Ala Ala Gln Lys Leu Met Arg Thr Asp
                180                 185                 190

Arg Leu Glu Val Cys Arg Glu Tyr Gln Arg Gly Asn Cys Asn Arg Gly
            195                 200                 205

Glu Asn Asp Cys Arg Phe Ala His Pro Ala Asp Ser Thr Met Ile Asp
        210                 215                 220

Thr Asn Asp Asn Thr Val Thr Val Cys Met Asp Tyr Ile Lys Gly Arg
225                 230                 235                 240

Cys Ser Arg Glu Lys Cys Lys Tyr Phe His Pro Pro Ala His Leu Gln
                245                 250                 255

Ala Lys Ile Lys Ala Ala Gln Tyr Gln Val Asn Gln Ala Ala Ala Ala
                260                 265                 270
```

```
Pro Lys Lys Lys Arg Lys Val Glu
        275             280
```

<210> SEQ ID NO 7
<211> LENGTH: 296
<212> TYPE: PRT
<213> ORGANISM: Artificial Sequence
<220> FEATURE:
<223> OTHER INFORMATION: Synthetic Polypeptide

<400> SEQUENCE: 7

```
Met Glu Tyr Pro Tyr Asp Val Pro Asp Tyr Ala Met Ala Val Ser Val
1               5                   10                  15

Thr Pro Ile Arg Asp Thr Lys Trp Leu Thr Leu Glu Val Cys Arg Glu
            20                  25                  30

Phe Gln Arg Gly Thr Cys Ser Arg Pro Asp Thr Glu Cys Lys Phe Ala
        35                  40                  45

His Pro Ser Lys Ser Cys Gln Val Glu Asn Gly Arg Val Ile Ala Cys
    50                  55                  60

Phe Asp Ser Leu Lys Gly Arg Cys Ser Arg Glu Asn Cys Lys Tyr Leu
65                  70                  75                  80

His Pro Pro Pro His Leu Lys Thr Gln Leu Glu Ile Asn Gly Arg Asn
                85                  90                  95

Asn Leu Ile Gln Gln Lys Asn Met Ala Met Leu Ala Gln Gln Met Gln
            100                 105                 110

Leu Ala Asn Ala Met Met Pro Gly Ala Pro Leu Gln Pro Val Pro Met
        115                 120                 125

Phe Ser Val Ala Pro Ser Leu Ala Thr Asn Ala Ser Ala Ala Ala Phe
    130                 135                 140

Asn Pro Tyr Leu Gly Pro Val Ser Pro Ser Leu Val Pro Ala Glu Ile
145                 150                 155                 160

Leu Pro Thr Ala Pro Met Leu Val Thr Gly Asn Pro Gly Val Pro Val
                165                 170                 175

Pro Ala Ala Ala Ala Ala Ala Gln Lys Leu Met Arg Asp Thr Lys
            180                 185                 190

Trp Leu Thr Leu Glu Val Cys Arg Glu Phe Gln Arg Gly Thr Cys Ser
        195                 200                 205

Arg Pro Asp Thr Glu Cys Lys Phe Ala His Pro Ser Lys Ser Cys Gln
    210                 215                 220

Val Glu Asn Gly Arg Val Ile Ala Cys Phe Asp Ser Leu Lys Gly Arg
225                 230                 235                 240

Cys Ser Arg Glu Asn Cys Lys Tyr Leu His Pro Pro Pro His Leu Lys
                245                 250                 255

Thr Gln Leu Glu Ile Asn Gly Arg Asn Asn Leu Ile Gln Gln Lys Asn
            260                 265                 270

Met Ala Met Leu Ala Gln Gln Met Gln Val Asn Gln Ala Ala Ala Ala
        275                 280                 285

Pro Lys Lys Lys Arg Lys Val Glu
    290                 295
```

<210> SEQ ID NO 8
<211> LENGTH: 262
<212> TYPE: PRT
<213> ORGANISM: Artificial Sequence
<220> FEATURE:
<223> OTHER INFORMATION: Synthetic Polypeptide

<400> SEQUENCE: 8

Met Glu Tyr Pro Tyr Asp Val Pro Asp Tyr Ala Met Ala Val Ser Val
1               5                   10                  15

Thr Pro Ile Arg Thr Asp Arg Leu Glu Val Cys Arg Glu Tyr Gln Arg
            20                  25                  30

Gly Asn Cys Asn Arg Gly Glu Asn Asp Cys Arg Phe Ala His Pro Ala
            35                  40                  45

Asp Ser Thr Met Ile Asp Thr Asn Asp Asn Thr Val Thr Val Cys Met
50                  55                  60

Asp Tyr Ile Lys Gly Arg Cys Ser Arg Glu Lys Cys Lys Tyr Phe His
65                  70                  75                  80

Pro Pro Ala His Leu Gln Ala Lys Ile Lys Ala Ala Gln Tyr Gln Leu
                85                  90                  95

Ala Asn Ala Met Met Pro Gly Ala Pro Leu Gln Pro Val Pro Met Phe
            100                 105                 110

Ser Val Ala Pro Ser Leu Ala Thr Asn Ala Ser Ala Ala Ala Phe Asn
            115                 120                 125

Pro Tyr Leu Gly Pro Val Ser Pro Ser Leu Val Pro Ala Glu Ile Leu
            130                 135                 140

Pro Thr Ala Pro Met Leu Val Thr Gly Asn Pro Gly Val Pro Val Pro
145                 150                 155                 160

Ala Ala Ala Ala Ala Ala Gln Lys Leu Met Arg Thr Asp Arg Leu
                165                 170                 175

Glu Val Cys Arg Glu Tyr Gln Arg Gly Asn Cys Asn Arg Gly Glu Asn
            180                 185                 190

Asp Cys Arg Phe Ala His Pro Ala Asp Ser Thr Met Ile Asp Thr Asn
            195                 200                 205

Asp Asn Thr Val Thr Val Cys Met Asp Tyr Ile Lys Gly Arg Cys Ser
210                 215                 220

Arg Glu Lys Cys Lys Tyr Phe His Pro Pro Ala His Leu Gln Ala Lys
225                 230                 235                 240

Ile Lys Ala Ala Gln Tyr Gln Val Asn Gln Ala Ala Ala Ala Pro Lys
                245                 250                 255

Lys Lys Arg Lys Val Glu
            260

<210> SEQ ID NO 9
<211> LENGTH: 261
<212> TYPE: PRT
<213> ORGANISM: Artificial Sequence
<220> FEATURE:
<223> OTHER INFORMATION: Synthetic Polypeptide

<400> SEQUENCE: 9

Met Glu Tyr Pro Tyr Asp Val Pro Asp Tyr Ala Gly Ser Ala Val Ser
1               5                   10                  15

Val Thr Pro Ile Arg Asp Thr Lys Trp Leu Thr Leu Glu Val Cys Arg
            20                  25                  30

Glu Phe Gln Arg Gly Thr Cys Ser Arg Pro Asp Thr Glu Cys Lys Phe
            35                  40                  45

Ala His Pro Ser Lys Ser Cys Gln Val Glu Asn Gly Arg Val Ile Ala
50                  55                  60

Cys Phe Asp Ser Leu Lys Gly Arg Cys Ser Arg Glu Asn Cys Lys Tyr
65                  70                  75                  80

Leu His Pro Pro Pro His Leu Lys Thr Gln Leu Glu Ile Asn Gly Arg
                85                  90                  95

```
Asn Asn Leu Ile Gln Gln Lys Asn Met Ala Met Leu Ala Gln Gln Met
            100                 105                 110

Gln Leu Ala Asn Ala Met Met Pro Gly Ala Pro Leu Gln Pro Val Pro
            115                 120                 125

Met Phe Ser Val Ala Pro Ser Leu Ala Thr Asn Ala Ser Ile Leu Pro
        130                 135                 140

Thr Ala Pro Met Leu Val Thr Gly Asn Pro Gly Val Pro Val Pro Ala
145                 150                 155                 160

Ala Ala Ala Ala Ala Gln Lys Leu Met Arg Thr Asp Arg Leu Glu
                165                 170                 175

Val Cys Arg Glu Tyr Gln Arg Gly Asn Cys Asn Arg Gly Glu Asn Asp
                180                 185                 190

Cys Arg Phe Ala His Pro Ala Asp Ser Thr Met Ile Asp Thr Asn Asp
            195                 200                 205

Asn Thr Val Thr Val Cys Met Asp Tyr Ile Lys Gly Arg Cys Ser Arg
        210                 215                 220

Glu Lys Cys Lys Tyr Phe His Pro Pro Ala His Leu Gln Ala Lys Ile
225                 230                 235                 240

Lys Ala Ala Gln Tyr Gln Val Asn Gln Ala Ala Ala Pro Lys Lys
                245                 250                 255

Lys Arg Lys Val Glu
            260

<210> SEQ ID NO 10
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 10

Met Glu Tyr Pro Tyr Asp Val Pro Asp Tyr Ala Gly Ser Ala Val Ser
1               5                   10                  15

Val Thr Pro Ile Arg Asp Thr Lys Trp Leu Thr Leu Glu Val Cys Arg
            20                  25                  30

Glu Phe Gln Arg Gly Thr Cys Ser Arg Pro Asp Thr Glu Cys Lys Phe
        35                  40                  45

Ala His Pro Ser Lys Ser Cys Gln Val Glu Asn Gly Arg Val Ile Ala
    50                  55                  60

Cys Phe Asp Ser Leu Lys Gly Arg Cys Ser Arg Glu Asn Cys Lys Tyr
65                  70                  75                  80

Leu His Pro Pro His Leu Lys Thr Gln Leu Glu Ile Asn Gly Arg
                85                  90                  95

Asn Asn Leu Ile Gln Gln Lys Asn Met Ala Met Leu Ala Gln Gln Met
            100                 105                 110

Gln Leu Ala Asn Ala Met Met Pro Gly Ala Pro Leu Gln Pro Val Pro
            115                 120                 125

Met Phe Ser Val Gly Asn Pro Gly Val Pro Val Pro Ala Ala Ala
        130                 135                 140

Ala Ala Ala Gln Lys Leu Met Arg Thr Asp Arg Leu Glu Val Cys Arg
145                 150                 155                 160

Glu Tyr Gln Arg Gly Asn Cys Asn Arg Gly Glu Asn Asp Cys Arg Phe
                165                 170                 175

Ala His Pro Ala Asp Ser Thr Met Ile Asp Thr Asn Asp Asn Thr Val
            180                 185                 190
```

```
Thr Val Cys Met Asp Tyr Ile Lys Gly Arg Cys Ser Arg Glu Lys Cys
        195                 200                 205

Lys Tyr Phe His Pro Ala His Leu Gln Ala Lys Ile Lys Ala Ala
    210                 215                 220

Gln Tyr Gln Val Asn Gln Ala Ala Ala Pro Lys Lys Arg Lys
225                 230                 235                 240

Val Glu

<210> SEQ ID NO 11
<211> LENGTH: 223
<212> TYPE: PRT
<213> ORGANISM: Artificial Sequence
<220> FEATURE:
<223> OTHER INFORMATION: Synthetic Polypeptide

<400> SEQUENCE: 11

Met Glu Tyr Pro Tyr Asp Val Pro Asp Tyr Ala Gly Ser Ala Val Ser
1               5                   10                  15

Val Thr Pro Ile Arg Asp Thr Lys Trp Leu Thr Leu Glu Val Cys Arg
                20                  25                  30

Glu Phe Gln Arg Gly Thr Cys Ser Arg Pro Asp Thr Glu Cys Lys Phe
            35                  40                  45

Ala His Pro Ser Lys Ser Cys Gln Val Glu Asn Gly Arg Val Ile Ala
        50                  55                  60

Cys Phe Asp Ser Leu Lys Gly Arg Cys Ser Arg Glu Asn Cys Lys Tyr
65                  70                  75                  80

Leu His Pro Pro His Leu Lys Thr Gln Leu Glu Ile Asn Gly Arg
                85                  90                  95

Asn Asn Leu Ile Gln Gln Lys Asn Met Ala Met Leu Ala Gln Gln Met
                100                 105                 110

Gln Leu Ala Asn Ala Met Met Pro Gly Ala Ala Ala Ala Ala Ala
            115                 120                 125

Gln Lys Leu Met Arg Thr Asp Arg Leu Glu Val Cys Arg Glu Tyr Gln
        130                 135                 140

Arg Gly Asn Cys Asn Arg Gly Glu Asn Asp Cys Arg Phe Ala His Pro
145                 150                 155                 160

Ala Asp Ser Thr Met Ile Asp Thr Asn Asp Asn Thr Val Thr Val Cys
                165                 170                 175

Met Asp Tyr Ile Lys Gly Arg Cys Ser Arg Glu Lys Cys Lys Tyr Phe
            180                 185                 190

His Pro Pro Ala His Leu Gln Ala Lys Ile Lys Ala Ala Gln Tyr Gln
        195                 200                 205

Val Asn Gln Ala Ala Ala Ala Pro Lys Lys Lys Arg Lys Val Glu
    210                 215                 220

<210> SEQ ID NO 12
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 12

Leu Ala Asn Ala Met Met Pro Gly Ala Pro Leu Gln Pro Val Pro Met
1               5                   10                  15

Phe Ser Val Ala Pro Ser Leu Ala Thr Asn Ala Ser Ile Leu Pro Thr
                20                  25                  30
```

```
Ala Pro Met Leu Val Thr Gly Asn Pro Gly Val Pro Val Pro Ala Ala
        35                  40                  45

Ala Ala Ala Ala Ala Gln Lys Leu Met
 50                  55
```

<210> SEQ ID NO 13
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 13

```
Leu Ala Asn Ala Met Met Pro Gly Ala Pro Leu Gln Pro Val Pro Met
 1                5                  10                  15

Phe Ser Val Gly Asn Pro Gly Val Pro Val Pro Ala Ala Ala Ala Ala
                 20                  25                  30

Ala Ala Gln Lys Leu Met
         35
```

<210> SEQ ID NO 14
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 14

```
Leu Ala Asn Ala Met Met Pro Gly Ala Ala Ala Ala Ala Ala Ala Gln
 1                5                  10                  15

Lys Leu Met
```

<210> SEQ ID NO 15
<211> LENGTH: 388
<212> TYPE: PRT
<213> ORGANISM: Homo sapiens

<400> SEQUENCE: 15

```
Met Ala Val Ser Val Thr Pro Ile Arg Asp Thr Lys Trp Leu Thr Leu
 1                5                  10                  15

Glu Val Cys Arg Glu Phe Gln Arg Gly Thr Cys Ser Arg Pro Asp Thr
                 20                  25                  30

Glu Cys Lys Phe Ala His Pro Ser Lys Ser Cys Gln Val Glu Asn Gly
             35                  40                  45

Arg Val Ile Ala Cys Phe Asp Ser Leu Lys Gly Arg Cys Ser Arg Glu
     50                  55                  60

Asn Cys Lys Tyr Leu His Pro Pro His Leu Lys Thr Gln Leu Glu
 65                  70                  75                  80

Ile Asn Gly Arg Asn Asn Leu Ile Gln Gln Lys Asn Met Ala Met Leu
                 85                  90                  95

Ala Gln Gln Met Gln Leu Ala Asn Ala Met Met Pro Gly Ala Pro Leu
                100                 105                 110

Gln Pro Val Pro Met Phe Ser Val Ala Pro Ser Leu Ala Thr Asn Ala
            115                 120                 125

Ser Ala Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160
```

Pro Gly Val Pro Val Pro Ala Ala Ala Ala Ala Ala Gln Lys Leu
            165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
            195                 200                 205

Thr Met Ile Asp Thr Asn Asp Asn Thr Val Thr Val Cys Met Asp Tyr
            210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
            245                 250                 255

Ala Ala Ala Ala Gln Ala Ala Ala Thr Ala Ala Ala Met Thr Gln Ser
            260                 265                 270

Ala Val Lys Ser Leu Lys Arg Pro Leu Glu Ala Thr Phe Asp Leu Gly
            275                 280                 285

Ile Pro Gln Ala Val Leu Pro Pro Leu Pro Lys Arg Pro Ala Leu Glu
            290                 295                 300

Lys Thr Asn Gly Ala Thr Ala Val Phe Asn Thr Gly Ile Phe Gln Tyr
305                 310                 315                 320

Gln Gln Ala Leu Ala Asn Met Gln Leu Gln Gln His Thr Ala Phe Leu
            325                 330                 335

Pro Pro Val Pro Met Val His Gly Ala Thr Pro Ala Thr Val Ser Ala
            340                 345                 350

Ala Thr Thr Ser Ala Thr Ser Val Pro Phe Ala Ala Thr Ala Thr Ala
            355                 360                 365

Asn Gln Ile Pro Ile Ile Ser Ala Glu His Leu Thr Ser His Lys Tyr
            370                 375                 380

Val Thr Gln Met
385

<210> SEQ ID NO 16
<211> LENGTH: 279
<212> TYPE: DNA
<213> ORGANISM: Artificial Sequence
<220> FEATURE:
<223> OTHER INFORMATION: Synthetic Polynucleotide

<400> SEQUENCE: 16
cgggacacaa atggctaac actggaagta tgtagagagt tccagagggg gacttgctca      60
cggccagaca cggaatgtaa atttgcacat ccttcgaaaa gctgccaagt tgaaaatgga     120
cgagtaatcg cctgctttga ttcattgaaa ggccgttgct ccaggagaa ctgcaaatat     180 cttcatccac ccccacattt aaaaacgcag ttggagataa atggacgcaa taacttgatt    240
cagcagaaga acatggccat gttggcccag caaatgcaa                          279

<210> SEQ ID NO 17
<211> LENGTH: 228
<212> TYPE: DNA
<213> ORGANISM: Artificial Sequence
<220> FEATURE:
<223> OTHER INFORMATION: Synthetic Polynucleotide

<400> SEQUENCE: 17
cgaacagaca gacttgaggt atgtcgagag taccaacgtg gcaattgcaa ccgaggagaa     60
aatgattgtc ggtttgctca tcctgctgac agcacaatga ttgacaccaa tgacaacaca    120

| | |
|---|---|
| gtcactgtgt gtatggatta catcaaaggg agatgctctc gggaaaagtg caaatacttt | 180 |
| catcccctg cacatttaca agccaagatc aaggctgccc aataccag | 228 |

<210> SEQ ID NO 18
<211> LENGTH: 228
<212> TYPE: DNA
<213> ORGANISM: Artificial Sequence
<220> FEATURE:
<223> OTHER INFORMATION: Synthetic Polynucleotide

<400> SEQUENCE: 18

| | |
|---|---|
| ctagccaatg ccatgatgcc tggtgcccca ttacaacccg tgccaatgtt ttcagttgca | 60 |
| ccaagcttag ccaccaatgc atcagcagcc gcctttaatc cctatctggg acctgtttct | 120 |
| ccaagcctgg tcccggcaga gatcttgccg actgcaccaa tgttggttac agggaatccg | 180 |
| ggtgtccctg tacctgcagc tgctgcagct gctgcacaga aattaatg | 228 |

<210> SEQ ID NO 19
<211> LENGTH: 843
<212> TYPE: DNA
<213> ORGANISM: Artificial Sequence
<220> FEATURE:
<223> OTHER INFORMATION: Synthetic Polynucleotide

<400> SEQUENCE: 19

| | |
|---|---|
| atggagtacc catacgacgt accagattac gctggatccg ctgttagtgt cacaccaatt | 60 |
| cgggacacaa aatggctaac actggaagta tgtagagagt tccagagggg gacttgctca | 120 |
| cggccagaca cggaatgtaa atttgcacat ccttcgaaaa gctgccaagt tgaaaatgga | 180 |
| cgagtaatcg cctgctttga ttcattgaaa ggccgttgct ccagggagaa ctgcaaatat | 240 |
| cttcatccac ccccacattt aaaaacgcag ttggagataa atggacgcaa taacttgatt | 300 |
| cagcagaaga acatggccat gttggcccag caaatgcaac tagccaatgc catgatgcct | 360 |
| ggtgccccat tacaacccgt gccaatgttt tcagttgcac caagcttagc caccaatgca | 420 |
| tcagcagccg cctttaatcc ctatctggga cctgtttctc aagcctggt cccggcagag | 480 |
| atcttgccga ctgcaccaat gttggttaca gggaatccgg gtgtccctgt acctgcagct | 540 |
| gctgcagctg ctgcacagaa attaatgcga acagacagac ttgaggtatg tcgagagtac | 600 |
| caacgtggca attgcaaccg aggagaaaat gattgtcggt ttgctcatcc tgctgacagc | 660 |
| acaatgattg acaccaatga caacacagtc actgtgtgta tggattacat caagggagaa | 720 |
| tgctctcggg aaaagtgcaa atactttcat ccccctgcac atttacaagc caagatcaag | 780 |
| gctgcccaat accaggtcaa ccaggctgca gctgcaccaa aaaagaagag aaaggtcgaa | 840 |
| tga | 843 |

<210> SEQ ID NO 20
<211> LENGTH: 891
<212> TYPE: DNA
<213> ORGANISM: Artificial Sequence
<220> FEATURE:
<223> OTHER INFORMATION: Synthetic Polynucleotide

<400> SEQUENCE: 20

| | |
|---|---|
| atggagtacc catacgacgt accagattac gctatggctg ttagtgtcac accaattcgg | 60 |
| gacacaaaat ggctaacact ggaagtatgt agagagttcc agagggggac ttgctcacgg | 120 |
| ccagacacga atgtaaattt gcacatcctt cgaaaagct gccaagttga aaatggacga | 180 |
| gtaatcgcct gctttgattc attgaaaggc cgttgctcca gggagaactg caaatatctt | 240 |

-continued

```
catccacccc cacatttaaa aacgcagttg gagataaatg gacgcaataa cttgattcag      300
cagaagaaca tggccatgtt ggcccagcaa atgcaactag ccaatgccat gatgcctggt      360
gccccattac aacccgtgcc aatgttttca gttgcaccaa gcttagccac caatgcatca      420
gcagccgcct ttaatcccta tctgggacct gtttctccaa gcctggtccc ggcagagatc      480
ttgccgactg caccaatgtt ggttacaggg aatccgggtg tccctgtacc tgcagctgct      540
gcagctgctg cacagaaatt aatgcgggac acaaaatggc taacactgga agtatgtaga      600
gagttccaga ggggacttg ctcacggcca gacacggaat gtaaatttgc acatccttcg       660
aaaagctgcc aagttgaaaa tggacgagta atcgcctgct tgattcattg aaaggccgt       720 tgctccaggg agaactgcaa atatcttcat ccaccccac atttaaaaac gcagttggag       780
ataaatggac gcaataactt gattcagcag aagaacatgg ccatgttggc ccagcaaatg     840
caagtcaacc aggctgcagc tgcaccaaaa aagaagagaa aggtcgaatg a               891
```

<210> SEQ ID NO 21
<211> LENGTH: 789
<212> TYPE: DNA
<213> ORGANISM: Artificial Sequence
<220> FEATURE:
<223> OTHER INFORMATION: Synthetic Polynucleotide

<400> SEQUENCE: 21

```
atggagtacc catacgacgt accagattac gctatggctg ttagtgtcac accaattcga      60
acagacagac ttgaggtatg tcgagagtac caacgtggca attgcaaccg aggagaaaat      120
gattgtcggt ttgctcatcc tgctgacagc acaatgattg acaccaatga caacacagtc      180
actgtgtgta tggattacat caaagggaga tgctctcggg aaaagtgcaa atactttcat      240
ccccctgcac atttacaagc caagatcaag gctgcccaat accagctagc caatgccatg      300
atgcctggtg ccccattaca acccgtgcca atgttttcag ttgcaccaag cttagccacc      360
aatgcatcag cagccgcctt taatccctat ctgggacctg tttctccaag cctggtcccg      420
gcagagatct tgccgactgc accaatgttg gttacaggga atccgggtgt ccctgtacct      480
gcagctgctg cagctgctgc acagaaatta atgcgaacag acagacttga ggtatgtcga      540
gagtaccaac gtggcaattg caaccgagga gaaaatgatt gtcggtttgc tcatcctgct      600
gacagcacaa tgattgacac caatgacaac acagtcactg tgtgtatgga ttacatcaaa      660
gggagatgct ctcgggaaaa gtgcaaatac tttcatcccc ctgcacattt acaagccaag      720
atcaaggctg cccaatacca gctcaaccag gctgcagctg caccaaaaaa gaagagaaag      780
gtcgaatga                                                             789
```

<210> SEQ ID NO 22
<211> LENGTH: 786
<212> TYPE: DNA
<213> ORGANISM: Artificial Sequence
<220> FEATURE:
<223> OTHER INFORMATION: Synthetic Polynucleotide

<400> SEQUENCE: 22

```
atggagtacc catacgacgt accagattac gctggatccg ctgttagtgt cacaccaatt      60
cgggacacaa aatggctaac actggaagta tgtagagagt tccagagggg gacttgctca      120
cggccagaca cggaatgtaa atttgcacat ccttcgaaaa gctgccaagt tgaaaatgga      180
cgagtaatcg cctgctttga ttcattgaaa ggccgttgct ccaggagaa ctgcaaatat       240
```

| | |
|---|---|
| cttcatccac ccccacattt aaaaacgcag ttggagataa atggacgcaa taacttgatt | 300 |
| cagcagaaga acatggccat gttggcccag caaatgcaac tagccaatgc catgatgcct | 360 |
| ggtgccccat tacaacccgt gccaatgttt tcagttgcac caagcttagc caccaatgca | 420 |
| tcaatcttgc cgactgcacc aatgttggtt acagggaatc cgggtgtccc tgtacctgca | 480 |
| gctgctgcag ctgctgcaca gaaattaatg cgaacagaca gacttgaggt atgtcgagag | 540 |
| taccaacgtg gcaattgcaa ccgaggagaa aatgattgtc ggtttgctca tcctgctgac | 600 |
| agcacaatga ttgacaccaa tgacaacaca gtcactgtgt gtatggatta catcaaaggg | 660 |
| agatgctctc gggaaaagtg caaatacttt catcccctg cacatttaca agccaagatc | 720 |
| aaggctgccc aataccaggt caaccaggct gcagctgcac aaaaaagaa gagaaaggtc | 780 |
| gaatga | 786 |

<210> SEQ ID NO 23
<211> LENGTH: 729
<212> TYPE: DNA
<213> ORGANISM: Artificial Sequence
<220> FEATURE:
<223> OTHER INFORMATION: Synthetic Polynucleotide

<400> SEQUENCE: 23

| | |
|---|---|
| atggagtacc catacgacgt accagattac gctggatccg ctgttagtgt cacaccaatt | 60 |
| cgggacacaa aatggctaac actggaagta tgtagagagt tccagagggg gacttgctca | 120 |
| cggccagaca cggaatgtaa atttgcacat ccttcgaaaa gctgccaagt tgaaaatgga | 180 |
| cgagtaatcg cctgctttga ttcattgaaa ggccgttgct ccaggagaa ctgcaaatat | 240 |
| cttcatccac ccccacattt aaaaacgcag ttggagataa atggacgcaa taacttgatt | 300 |
| cagcagaaga acatggccat gttggcccag caaatgcaac tagccaatgc catgatgcct | 360 |
| ggtgccccat tacaacccgt gccaatgttt tcagttggga atccgggtgt ccctgtacct | 420 |
| gcagctgctg cagctgctgc acagaaatta atgcgaacag acagacttga ggtatgtcga | 480 |
| gagtaccaac gtggcaattg caaccgagga gaaaatgatt gtcggtttgc tcatcctgct | 540 |
| gacagcacaa tgattgacac caatgacaac acagtcactg tgtgtatgga ttacatcaaa | 600 |
| gggagatgct ctcgggaaaa gtgcaaatac tttcatcccc ctgcacattt acaagccaag | 660 |
| atcaaggctg cccaatacca ggtcaaccag gctgcagctg caccaaaaaa gaagagaaag | 720 |
| gtcgaatga | 729 |

<210> SEQ ID NO 24
<211> LENGTH: 672
<212> TYPE: DNA
<213> ORGANISM: Artificial Sequence
<220> FEATURE:
<223> OTHER INFORMATION: Synthetic Polynucleotide

<400> SEQUENCE: 24

| | |
|---|---|
| atggagtacc catacgacgt accagattac gctggatccg ctgttagtgt cacaccaatt | 60 |
| cgggacacaa aatggctaac actggaagta tgtagagagt tccagagggg gacttgctca | 120 |
| cggccagaca cggaatgtaa atttgcacat ccttcgaaaa gctgccaagt tgaaaatgga | 180 |
| cgagtaatcg cctgctttga ttcattgaaa ggccgttgct ccaggagaa ctgcaaatat | 240 |
| cttcatccac ccccacattt aaaaacgcag ttggagataa atggacgcaa taacttgatt | 300 |
| cagcagaaga acatggccat gttggcccag caaatgcaac tagccaatgc catgatgcct | 360 |
| ggtgccgctg ctgcagctgc tgcacagaaa ttaatgcgaa cagacagact tgaggtatgt | 420 |

```
cgagagtacc aacgtggcaa ttgcaaccga ggagaaaatg attgtcggtt tgctcatcct    480
gctgacagca caatgattga caccaatgac aacacagtca ctgtgtgtat ggattacatc    540
aaagggagat gctctcggga aaagtgcaaa tactttcatc cccctgcaca tttacaagcc    600
aagatcaagg ctgcccaata ccaggtcaac caggctgcag ctgcaccaaa aaagaagaga    660
aaggtcgaat ga                                                        672
```

<210> SEQ ID NO 25
<211> LENGTH: 283
<212> TYPE: PRT
<213> ORGANISM: Artificial Sequence
<220> FEATURE:
<223> OTHER INFORMATION: Synthetic Polypeptide

<400> SEQUENCE: 25

```
Met Glu Tyr Pro Tyr Asp Val Pro Asp Tyr Ala Met Ala Val Ser Val
1               5                   10                  15

Thr Pro Ile Arg Asp Thr Lys Trp Leu Thr Leu Glu Val Cys Arg Glu
            20                  25                  30

Phe Gln Arg Gly Thr Cys Ser Arg Pro Asp Thr Glu Cys Lys Phe Ala
        35                  40                  45

His Pro Ser Lys Ser Cys Gln Val Glu Asn Gly Arg Val Ile Ala Cys
    50                  55                  60

Phe Asp Ser Leu Lys Gly Arg Cys Ser Arg Glu Asn Cys Lys Tyr Leu
65                  70                  75                  80

His Pro Pro Pro His Leu Lys Thr Gln Leu Glu Ile Asn Gly Arg Asn
                85                  90                  95

Asn Leu Ile Gln Gln Lys Asn Met Ala Met Leu Ala Gln Gln Met Gln
            100                 105                 110

Leu Ala Asn Ala Met Met Pro Gly Ala Pro Leu Gln Pro Val Pro Met
        115                 120                 125

Phe Ser Val Ala Pro Ser Leu Ala Thr Asn Ala Ser Ala Ala Ala Phe
    130                 135                 140

Asn Pro Tyr Leu Gly Pro Val Ser Pro Ser Leu Val Pro Ala Glu Ile
145                 150                 155                 160

Leu Pro Thr Ala Pro Met Leu Val Thr Gly Asn Pro Gly Val Pro Val
                165                 170                 175

Pro Ala Ala Ala Ala Ala Ala Gln Lys Leu Met Ser Pro Gln Gln
            180                 185                 190

Ser Glu Cys Asn Pro Val Gly Ala Leu Gln Glu Leu Val Val Gln Lys
        195                 200                 205

Gly Trp Arg Leu Pro Glu Tyr Thr Val Thr Gln Glu Ser Gly Pro Ala
    210                 215                 220

His Arg Lys Glu Phe Thr Met Thr Cys Arg Val Glu Arg Phe Ile Glu
225                 230                 235                 240

Ile Gly Ser Gly Thr Ser Lys Lys Leu Ala Lys Arg Asn Ala Ala Ala
                245                 250                 255

Lys Met Leu Leu Arg Val His Thr Val Pro Leu Asp Ala Arg Asp Gly
            260                 265                 270

Tyr Gly Arg Lys Lys Arg Gln Arg Arg
        275                 280
```

<210> SEQ ID NO 26
<211> LENGTH: 272
<212> TYPE: PRT

<213> ORGANISM: Artificial Sequence
<220> FEATURE:
<223> OTHER INFORMATION: Synthetic Polypeptide

<400> SEQUENCE: 26

```
Met Glu Tyr Pro Tyr Asp Val Pro Asp Tyr Ala Met Ala Val Ser Val
1               5                   10                  15

Thr Pro Ile Arg Asp Thr Lys Trp Leu Thr Leu Glu Val Cys Arg Glu
            20                  25                  30

Phe Gln Arg Gly Thr Cys Ser Arg Pro Asp Thr Glu Cys Lys Phe Ala
        35                  40                  45

His Pro Ser Lys Ser Cys Gln Val Glu Asn Gly Arg Val Ile Ala Cys
    50                  55                  60

Phe Asp Ser Leu Lys Gly Arg Cys Ser Arg Glu Asn Cys Lys Tyr Leu
65                  70                  75                  80

His Pro Pro Pro His Leu Lys Thr Gln Leu Glu Ile Asn Gly Arg Asn
                85                  90                  95

Asn Leu Ile Gln Gln Lys Asn Met Ala Met Leu Ala Gln Gln Met Gln
            100                 105                 110

Leu Ala Asn Ala Met Met Pro Gly Ala Pro Leu Gln Pro Val Pro Met
        115                 120                 125

Phe Ser Val Ala Pro Ser Leu Ala Thr Asn Ala Ser Ala Ala Ala Phe
    130                 135                 140

Asn Pro Tyr Leu Gly Pro Val Ser Pro Ser Leu Val Pro Ala Glu Ile
145                 150                 155                 160

Leu Pro Thr Ala Pro Met Leu Val Thr Gly Asn Pro Gly Val Pro Val
                165                 170                 175

Pro Ala Ala Ala Ala Ala Ala Gln Lys Leu Met Gln Glu Asn Pro
            180                 185                 190

Val Gly Ser Leu Gln Glu Leu Ala Val Gln Lys Gly Trp Arg Leu Pro
        195                 200                 205

Glu Tyr Thr Val Ala Gln Glu Ser Gly Pro Pro His Lys Arg Glu Phe
    210                 215                 220

Thr Ile Thr Cys Arg Val Glu Thr Phe Val Glu Thr Gly Ser Gly Thr
225                 230                 235                 240

Ser Lys Gln Val Ala Lys Arg Val Ala Ala Glu Lys Leu Leu Thr Lys
                245                 250                 255

Phe Lys Thr Ile Ser Tyr Gly Arg Lys Lys Arg Gln Arg Arg Arg
            260                 265                 270
```

<210> SEQ ID NO 27
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 27

```
Met His His His His His His Ala Asn Val Val Asn Met Asn Ser Leu
1               5                   10                  15

Leu Asn Gly Lys Asp Ser Arg Trp Leu Gln Leu Glu Val Cys Arg Glu
            20                  25                  30

Phe Gln Arg Asn Lys Cys Ser Arg Gln Asp Thr Glu Cys Lys Phe Ala
        35                  40                  45

His Pro Pro Ala Asn Val Glu Val Gln Asn Gly Lys Val Thr Ala Cys
    50                  55                  60
```

```
Tyr Asp Ser Ile Lys Gly Arg Cys Asn Arg Asp Lys Pro Pro Cys Lys
 65                  70                  75                  80

Tyr Phe His Pro Pro Gln His Leu Lys Asp Gln Leu Leu Ile Asn Gly
                 85                  90                  95

Arg Asn His Leu Ala Leu Lys Asn Ala Leu Met Gln Gln Met Gly Tyr
            100                 105                 110

Gly Arg Lys Lys Arg Gln Arg Arg
        115                 120

<210> SEQ ID NO 28
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 28

Met His His His His His Ala Asn Val Val Asn Met Asn Ser Leu
 1               5                  10                  15

Leu Asn Gly Lys Asp Ser Arg Trp Leu Gln Leu Glu Val Cys Arg Glu
                20                  25                  30

Phe Gln Arg Asn Lys Cys Ser Arg Gln Asp Thr Glu Cys Lys Phe Ala
            35                  40                  45

His Pro Pro Ala Asn Val Glu Val Gln Asn Gly Lys Val Thr Ala Cys
        50                  55                  60

Tyr Asp Ser Ile Lys Gly Arg Cys Asn Arg Asp Lys Pro Pro Cys Lys
 65                  70                  75                  80

Tyr Phe His Pro Pro Gln His Leu Lys Asp Gln Leu Leu Ile Asn Gly
                 85                  90                  95

Arg Asn His Leu Ala Leu Lys Asn Ala Leu Met Gln Gln Met Gly Arg
            100                 105                 110

Arg Arg Arg Arg Arg Arg Arg
        115

<210> SEQ ID NO 29
<211> LENGTH: 98
<212> TYPE: PRT
<213> ORGANISM: Artificial Sequence
<220> FEATURE:
<223> OTHER INFORMATION: Synthetic Polypeptide

<400> SEQUENCE: 29

Met His His His His His Met Ala Val Ser Val Thr Pro Ile Arg
 1               5                  10                  15

Asp Thr Lys Trp Leu Thr Leu Glu Val Cys Arg Glu Phe Gln Arg Gly
                20                  25                  30

Thr Cys Ser Arg Pro Asp Thr Glu Cys Lys Phe Ala His Pro Ser Lys
            35                  40                  45

Ser Cys Gln Val Glu Asn Gly Arg Val Ile Ala Cys Phe Asp Ser Leu
        50                  55                  60

Lys Gly Arg Cys Ser Arg Glu Asn Cys Lys Tyr Leu His Pro Pro Pro
 65                  70                  75                  80

His Leu Lys Thr Gln Leu Glu Tyr Gly Arg Lys Lys Arg Arg Gln Arg
                85                  90                  95

Arg Arg

<210> SEQ ID NO 30
<211> LENGTH: 116
```

<212> TYPE: PRT
<213> ORGANISM: Artificial Sequence
<220> FEATURE:
<223> OTHER INFORMATION: Synthetic Polypeptide

<400> SEQUENCE: 30

Met His His His His His His Met Ala Val Ser Val Thr Pro Ile Arg
1               5                   10                  15

Asp Thr Lys Trp Leu Thr Leu Glu Val Cys Arg Glu Phe Gln Arg Gly
            20                  25                  30

Thr Cys Ser Arg Pro Asp Thr Glu Cys Lys Phe Ala His Pro Ser Lys
        35                  40                  45

Ser Cys Gln Val Glu Asn Gly Arg Val Ile Ala Cys Phe Asp Ser Leu
    50                  55                  60

Lys Gly Arg Cys Ser Arg Glu Asn Cys Lys Tyr Leu His Pro Pro Pro
65                  70                  75                  80

His Leu Lys Thr Gln Leu Glu Ile Asn Gly Arg Asn Asn Leu Ile Gln
                85                  90                  95

Gln Lys Asn Met Ala Met Leu Ala Gln Gln Met Gln Arg Arg Arg Arg
            100                 105                 110

Arg Arg Arg Arg
        115

<210> SEQ ID NO 31
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 31

Pro Ala Ala Lys Arg Val Lys Leu Asp
1               5

<210> SEQ ID NO 32
<211> LENGTH: 94
<212> TYPE: PRT
<213> ORGANISM: Artificial Sequence
<220> FEATURE:
<223> OTHER INFORMATION: Synthetic Polypeptide

<400> SEQUENCE: 32

Arg Asp Thr Lys Trp Leu Thr Leu Glu Val Cys Arg Gln Phe Gln Arg
1               5                   10                  15

Gly Thr Cys Ser Arg Ser Asp Glu Glu Cys Lys Phe Ala His Pro Pro
            20                  25                  30

Lys Ser Cys Gln Val Glu Asn Gly Arg Val Ile Ala Cys Phe Asp Ser
        35                  40                  45

Leu Lys Gly Arg Cys Ser Arg Glu Asn Cys Lys Tyr Leu His Pro Pro
    50                  55                  60

Thr His Leu Lys Thr Gln Leu Glu Ile Asn Gly Arg Asn Asn Leu Ile
65                  70                  75                  80

Gln Gln Lys Thr Ala Ala Ala Met Leu Ala Gln Gln Met Gln
            85                  90

<210> SEQ ID NO 33
<211> LENGTH: 94
<212> TYPE: PRT
<213> ORGANISM: Artificial Sequence
<220> FEATURE:
<223> OTHER INFORMATION: Synthetic Polypeptide

<400> SEQUENCE: 33

Arg Asp Thr Lys Trp Leu Thr Leu Glu Val Cys Arg Glu Phe Gln Arg
1               5                   10                  15

Gly Thr Cys Ser Arg Ala Asp Ala Asp Cys Lys Phe Ala His Pro Pro
            20                  25                  30

Arg Val Cys His Val Glu Asn Gly Arg Val Val Ala Cys Phe Asp Ser
        35                  40                  45

Leu Lys Gly Arg Cys Thr Arg Glu Asn Cys Lys Tyr Leu His Pro Pro
    50                  55                  60

Pro His Leu Lys Thr Gln Leu Glu Ile Asn Gly Arg Asn Asn Leu Ile
65                  70                  75                  80

Gln Gln Lys Thr Ala Ala Ala Met Phe Ala Gln Gln Met Gln
                85                  90

<210> SEQ ID NO 34
<211> LENGTH: 76
<212> TYPE: PRT
<213> ORGANISM: Artificial Sequence
<220> FEATURE:
<223> OTHER INFORMATION: Synthetic Polypeptide

<400> SEQUENCE: 34

Arg Thr Asp Lys Leu Glu Val Cys Arg Glu Phe Gln Arg Gly Asn Cys
1               5                   10                  15

Ala Arg Gly Glu Thr Asp Cys Arg Phe Ala His Pro Ala Asp Ser Thr
            20                  25                  30

Met Ile Asp Thr Ser Asp Asn Thr Val Thr Val Cys Met Asp Tyr Ile
        35                  40                  45

Lys Gly Arg Cys Met Arg Glu Lys Cys Lys Tyr Phe His Pro Pro Ala
    50                  55                  60

His Leu Gln Ala Lys Ile Lys Ala Ala Gln His Gln
65                  70                  75

<210> SEQ ID NO 35
<211> LENGTH: 76
<212> TYPE: PRT
<213> ORGANISM: Artificial Sequence
<220> FEATURE:
<223> OTHER INFORMATION: Synthetic Polypeptide

<400> SEQUENCE: 35

Arg Ser Asp Lys Leu Glu Val Cys Arg Glu Phe Gln Arg Gly Asn Cys
1               5                   10                  15

Thr Arg Gly Glu Asn Asp Cys Arg Tyr Ala His Pro Thr Asp Ala Ser
            20                  25                  30

Met Ile Glu Ala Ser Asp Asn Thr Val Thr Ile Cys Met Asp Tyr Ile
        35                  40                  45

Lys Gly Arg Cys Ser Arg Glu Lys Cys Lys Tyr Phe His Pro Pro Ala
    50                  55                  60

His Leu Gln Ala Arg Leu Lys Ala Ala His His Gln
65                  70                  75

<210> SEQ ID NO 36
<211> LENGTH: 17
<212> TYPE: RNA
<213> ORGANISM: Artificial Sequence
<220> FEATURE:
<223> OTHER INFORMATION: Synthetic Polypeptide

```
<400> SEQUENCE: 36
gcugcuguuc gcugcug                                                    17

<210> SEQ ID NO 37
<211> LENGTH: 17
<212> TYPE: RNA
<213> ORGANISM: Artificial Sequence
<220> FEATURE:
<223> OTHER INFORMATION: Synthetic Polypeptide

<400> SEQUENCE: 37
gcagcaguuc gcagcag                                                    17

<210> SEQ ID NO 38
<211> LENGTH: 23
<212> TYPE: RNA
<213> ORGANISM: Artificial Sequence
<220> FEATURE:
<223> OTHER INFORMATION: Synthetic Polypeptide

<400> SEQUENCE: 38
uuuugcuuuu uuuuuugcu uuu                                              23

<210> SEQ ID NO 39
<211> LENGTH: 23
<212> TYPE: RNA
<213> ORGANISM: Artificial Sequence
<220> FEATURE:
<223> OTHER INFORMATION: Synthetic Polypeptide

<400> SEQUENCE: 39
uuuuccuuuu uuuuuuccu uuu                                              23

<210> SEQ ID NO 40
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 40

Pro Lys Lys Lys Arg Lys Val
1               5

<210> SEQ ID NO 41
<211> LENGTH: 125
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (34)..(73)
<223> OTHER INFORMATION: n is a, c, g, or t

<400> SEQUENCE: 41
acactctttc cctacacgac gctcttccga tctnnnnnnn nnnnnnnnnn nnnnnnnnnn     60
nnnnnnnnnn nnngatcgga agagcacacg tctgaactcc agtcacccta tagtgagtcg    120
tatta                                                                125

<210> SEQ ID NO 42
<211> LENGTH: 20
<212> TYPE: DNA
<213> ORGANISM: Artificial Sequence
<220> FEATURE:
```

<223> OTHER INFORMATION: Synthetic Polynucleotide

<400> SEQUENCE: 42
taatacgact cactataggg                                          20

<210> SEQ ID NO 43
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 43
actgacctca agtctgcaca cgagaaggct ag                            32

<210> SEQ ID NO 44
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 44
aatgatacgg cgaccaccga gatctacact ctttccctac acgacgctct tccgatct   58

<210> SEQ ID NO 45
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 45
agagaaaggt cgaatgagcg g                                        21

<210> SEQ ID NO 46
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 46
tgcattctag ttgtggtttg tcc                                      23

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 47
aatcccatca ccatcttcca                                          20

<210> SEQ ID NO 48
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 48
tggactccac gacgtactca                                          20

```
<210> SEQ ID NO 49
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 49
caagcagaag acggcatacg agatcactgt gtgactggag ttcagacgtg tgctcttccg      60
atc                                                                   63

<210> SEQ ID NO 50
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 50
caagcagaag acggcatacg agatattggc gtgactggag ttcagacgtg tgctcttccg      60
atc                                                                   63

<210> SEQ ID NO 51
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 51
caagcagaag acggcatacg agatgatctg gtgactggag ttcagacgtg tgctcttccg      60
atc                                                                   63

<210> SEQ ID NO 52
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 52
caagcagaag acggcatacg agattcaagt gtgactggag ttcagacgtg tgctcttccg      60
atc                                                                   63

<210> SEQ ID NO 53
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 53
caagcagaag acggcatacg agatctgatc gtgactggag ttcagacgtg tgctcttccg      60
atc                                                                   63

<210> SEQ ID NO 54
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 54
```

```
caagcagaag acggcatacg agataagcta gtgactggag ttcagacgtg tgctcttccg    60
atc                                                                  63

<210> SEQ ID NO 55
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 55
caagcagaag acggcatacg agatgtagcc gtgactggag ttcagacgtg tgctcttccg    60
atc                                                                  63

<210> SEQ ID NO 56
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 56
caagcagaag acggcatacg agattacaag gtgactggag ttcagacgtg tgctcttccg    60
atc                                                                  63

<210> SEQ ID NO 57
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 57
caagcagaag acggcatacg agatggacgg gtgactggag ttcagacgtg tgctcttccg    60
atc                                                                  63

<210> SEQ ID NO 58
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 58
caagcagaag acggcatacg agattgacat gtgactggag ttcagacgtg tgctcttccg    60
atc                                                                  63

<210> SEQ ID NO 59
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 59
caagcagaag acggcatacg agatggaact gtgactggag ttcagacgtg tgctcttccg    60
atc                                                                  63

<210> SEQ ID NO 60
<211> LENGTH: 63
<212> TYPE: DNA
<213> ORGANISM: Artificial Sequence
```

```
<220> FEATURE:
<223> OTHER INFORMATION: Synthetic Polynucleotide

<400> SEQUENCE: 60
caagcagaag acggcatacg agatttgact gtgactggag ttcagacgtg tgctcttccg      60
atc                                                                   63

<210> SEQ ID NO 61
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 61
caagcagaag acggcatacg agatcgtgat gtgactggag ttcagacgtg tgctcttccg      60
atc                                                                   63

<210> SEQ ID NO 62
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 62
caagcagaag acggcatacg agatacatcg gtgactggag ttcagacgtg tgctcttccg      60
atc                                                                   63

<210> SEQ ID NO 63
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 63
caagcagaag acggcatacg agatgcctaa gtgactggag ttcagacgtg tgctcttccg      60
atc                                                                   63

<210> SEQ ID NO 64
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 64
caagcagaag acggcatacg agattggtca gtgactggag ttcagacgtg tgctcttccg      60
atc                                                                   63

<210> SEQ ID NO 65
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 65
caagcagaag acggcatacg agatctctac gtgactggag ttcagacgtg tgctcttccg      60
atc                                                                   63
```

```
<210> SEQ ID NO 66
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 66
caagcagaag acggcatacg agatgcggac gtgactggag ttcagacgtg tgctcttccg      60
atc                                                                    63

<210> SEQ ID NO 67
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 67
caagcagaag acggcatacg agattttcac gtgactggag ttcagacgtg tgctcttccg      60
atc                                                                    63

<210> SEQ ID NO 68
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 68
caagcagaag acggcatacg agatggccac gtgactggag ttcagacgtg tgctcttccg      60
atc                                                                    63

<210> SEQ ID NO 69
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 69
caagcagaag acggcatacg agatcgaaac gtgactggag ttcagacgtg tgctcttccg      60
atc                                                                    63

<210> SEQ ID NO 70
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 70
caagcagaag acggcatacg agatcgtacg gtgactggag ttcagacgtg tgctcttccg      60
atc                                                                    63

<210> SEQ ID NO 71
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 71
```

```
caagcagaag acggcatacg agatccactc gtgactggag ttcagacgtg tgctcttccg    60
atc                                                                  63

<210> SEQ ID NO 72
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 72
caagcagaag acggcatacg agatgctacc gtgactggag ttcagacgtg tgctcttccg    60
atc                                                                  63

<210> SEQ ID NO 73
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 73
caagcagaag acggcatacg agatatcagt gtgactggag ttcagacgtg tgctcttccg    60
atc                                                                  63

<210> SEQ ID NO 74
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 74

His His His His His His
1               5

<210> SEQ ID NO 75
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 75

Tyr Gly Arg Lys Lys Arg Arg Gln Arg Arg Arg
1               5                   10

<210> SEQ ID NO 76
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 76

Arg Arg Arg Arg Arg Arg Arg Arg
1               5

<210> SEQ ID NO 77
<211> LENGTH: 84
<212> TYPE: PRT
<213> ORGANISM: Artificial Sequence
<220> FEATURE:
<223> OTHER INFORMATION: Synthetic Polypeptide
```

<400> SEQUENCE: 77

Ser Pro Gln Gln Ser Glu Cys Asn Pro Val Gly Ala Leu Gln Glu Leu
1               5                   10                  15

Val Val Gln Lys Gly Trp Arg Leu Pro Glu Tyr Thr Val Thr Gln Glu
            20                  25                  30

Ser Gly Pro Ala His Arg Lys Glu Phe Thr Met Thr Cys Arg Val Glu
        35                  40                  45

Arg Phe Ile Glu Ile Gly Ser Gly Thr Ser Lys Lys Leu Ala Lys Arg
    50                  55                  60

Asn Ala Ala Ala Lys Met Leu Leu Arg Val His Thr Val Pro Leu Asp
65                  70                  75                  80

Ala Arg Asp Gly

<210> SEQ ID NO 78
<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 78

Gln Glu Asn Pro Val Gly Ser Leu Gln Glu Leu Ala Val Gln Lys Gly
1               5                   10                  15

Trp Arg Leu Pro Glu Tyr Thr Val Ala Gln Glu Ser Gly Pro Pro His
            20                  25                  30

Lys Arg Glu Phe Thr Ile Thr Cys Arg Val Gly Thr Phe Val Glu Thr
        35                  40                  45

Gly Ser Gly Thr Ser Lys Gln Val Ala Lys Arg Val Ala Ala Glu Lys
    50                  55                  60

Leu Leu Thr Lys Phe Lys Thr Ile Ser
65                  70

<210> SEQ ID NO 79
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 79

Ala Asn Val Val Asn Met Asn Ser Leu Leu Asn Gly Lys Asp Ser Arg
1               5                   10                  15

Trp Leu Gln Leu Glu Val Cys Arg Glu Phe Gln Arg Asn Lys Cys Ser
            20                  25                  30

Arg Gln Asp Thr Glu Cys Lys Phe Ala His Pro Pro Ala Asn Val Glu
        35                  40                  45

Val Gln Asn Gly Lys Val Thr Ala Cys Tyr Asp Ser Ile Lys Gly Arg
    50                  55                  60

Cys Asn Arg Asp Lys Pro Pro Cys Lys Tyr Phe His Pro Pro Gln His
65                  70                  75                  80

Leu Lys Asp Gln Leu Leu Ile Asn Gly Arg Asn His Leu Ala Leu Lys
                85                  90                  95

Asn Ala Leu Met Gln Gln Met Gly
            100

<210> SEQ ID NO 80
<211> LENGTH: 4

```
<212> TYPE: PRT
<213> ORGANISM: Artificial Sequence
<220> FEATURE:
<223> OTHER INFORMATION: Synthetic Polypeptide

<400> SEQUENCE: 80

Cys Cys Cys His
1

<210> SEQ ID NO 81
<211> LENGTH: 105
<212> TYPE: DNA
<213> ORGANISM: Artificial Sequence
<220> FEATURE:
<223> OTHER INFORMATION: Synthetic Polynucleotide

<400> SEQUENCE: 81
attcaaaaag ggaacttcag gaaccaacgg aaaactgtca aatgctttaa ttgtggaaag      60
gaaggccata tagcaaaaaa ttgtagagca ccaagaaaaa agggg                    105

<210> SEQ ID NO 82
<211> LENGTH: 300
<212> TYPE: DNA
<213> ORGANISM: Artificial Sequence
<220> FEATURE:
<223> OTHER INFORMATION: Synthetic Polynucleotide

<400> SEQUENCE: 82
aacacggaaa acaagtctca gcccaagcgg ctgcatgtct ccaatatccc cttcaggttc      60
cgggatccgg acctcagaca atgtttggt caatttggta aaatcttaga tgttgaaatt     120
atttttaatg agcgaggctc aaagggattt ggtttcgtaa cttcgaaaa tagtgccgat     180 gcggacaggg cgagggagaa attacacggc accgtggtag agggccgtaa aatcgaggta     240
aataatgcca cagcacgtgt aatgacaaat aaaaagaccg tcaaccctta tacaaatggc     300

<210> SEQ ID NO 83
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 83
agaagtagaa atcgtggccc acctccctct tggggtcgtc gccctcgaga tgattatcgt      60
aggaggagtc ctccacctcg tcgcagatct ccaagaagga gaagcttctc tcgcagccgg     120
agcaggtccc tttctagaga taggagaaga gagagatcgc tgtctcggga gagaaatcac     180
aagccgtccc gatccttctc taggtctcgt agtcgatcta ggtcaaatga aaggaaa       237

<210> SEQ ID NO 84
<211> LENGTH: 705
<212> TYPE: DNA
<213> ORGANISM: Artificial Sequence
<220> FEATURE:
<223> OTHER INFORMATION: Synthetic Polynucleotide

<400> SEQUENCE: 84
atggagtacc catacgacgt accagattac gctatggctg ttagtgtcac accaattcgg      60
gacacaaaat ggctaacact ggaagtatgt agagagttcc agaggggac ttgctcacgg     120 ccagacacgg aatgtaaatt tgcacatcct tcgaaaagct gccaagttga aaatggacga     180
gtaatcgcct gctttgattc attgaaaggc cgttgctcca gggagaactg caaatatctt     240
```

| catccacccc cacatttaaa aacgcagttg gagataaatg gacgcaataa cttgattcag | 300 |
| cagaagaaca tggccatgtt ggcccagcaa atgcaactag ccaatgccat gatgcctggt | 360 |
| gccccattac aacccgtgcc aatgttttca gttgcaccaa gcttagccac caatgcatca | 420 |
| gcagccgcct ttaatcccta tctgggacct gtttctccaa gcctggtccc ggcagagatc | 480 |
| ttgccgactg caccaatgtt ggttacaggg aatcccgggg tccctgtacc tgcagctgct | 540 |
| gcagctgctg cacagaaatt aatgattcaa aagggaact tcaggaacca acggaaaact | 600 |
| gtcaaatgct taattgtgg aaaggaaggc catatagcaa aaattgtag agcaccaaga | 660 |
| aaaaggggt atggtcgtaa aaacgccgc cagcgtcgcc gctga | 705 |

<210> SEQ ID NO 85
<211> LENGTH: 891
<212> TYPE: DNA
<213> ORGANISM: Artificial Sequence
<220> FEATURE:
<223> OTHER INFORMATION: Synthetic Polynucleotide

<400> SEQUENCE: 85

| atggagtacc catacgacgt accagattac gctatggctg ttagtgtcac accaattcgg | 60 |
| gacacaaaat ggctaacact ggaagtatgt agagagttcc agaggggac ttgctcacgg | 120 |
| ccagacacgg aatgtaaatt tgcacatcct tcgaaaagct gccaagttga aatggacga | 180 |
| gtaatcgcct gctttgattc attgaaaggc cgttgctcca gggagaactg caaatatctt | 240 |
| catccacccc cacatttaaa aacgcagttg gagataaatg gacgcaataa cttgattcag | 300 |
| cagaagaaca tggccatgtt ggcccagcaa atgcaactag ccaatgccat gatgcctggt | 360 |
| gccccattac aacccgtgcc aatgttttca gttgcaccaa gcttagccac caatgcatca | 420 |
| gcagccgcct ttaatcccta tctgggacct gtttctccaa gcctggtccc ggcagagatc | 480 |
| ttgccgactg caccaatgtt ggttacaggg aatcccgggtg tccctgtacc tgcagctgct | 540 |
| gcagctgctg cacagaaatt aatgaacacg gaaacaagt ctcagcccaa gcggctgcat | 600 |
| gtctccaata tccccttcag gttccgggat ccggacctca gacaaatgtt tggtcaattt | 660 |
| ggtaaaatct tagatgttga aattattttt aatgagcgag gctcaaaggg atttggttc | 720 |
| gtaactttcg aaaatagtgc cgatgcggac agggcgaggg agaaattaca cggcaccgtg | 780 |
| gtagagggcc gtaaaatcga ggtaaataat gccacagcac gtgtaatgac aaataaaaag | 840 |
| accgtcaacc cttatacaaa tggcccaaaa agaagagaa aggtcgaatg a | 891 |

<210> SEQ ID NO 86
<211> LENGTH: 804
<212> TYPE: DNA
<213> ORGANISM: Artificial Sequence
<220> FEATURE:
<223> OTHER INFORMATION: Synthetic Polynucleotide

<400> SEQUENCE: 86

| atggagtacc catacgacgt accagattac gctatggctg ttagtgtcac accaattcgg | 60 |
| gacacaaaat ggctaacact ggaagtatgt agagagttcc agaggggac ttgctcacgg | 120 |
| ccagacacgg aatgtaaatt tgcacatcct tcgaaaagct gccaagttga aatggacga | 180 |
| gtaatcgcct gctttgattc attgaaaggc cgttgctcca gggagaactg caaatatctt | 240 |
| catccacccc cacatttaaa aacgcagttg gagataaatg gacgcaataa cttgattcag | 300 |
| cagaagaaca tggccatgtt ggcccagcaa atgcaactag ccaatgccat gatgcctggt | 360 |

```
gccccattac aacccgtgcc aatgttttca gttgcaccaa gcttagccac caatgcatca    420
gcagccgcct ttaatcccta tctgggacct gtttctccaa gcctggtccc ggcagagatc    480
ttgccgactg caccaatgtt ggttacaggg aatccgggtg tccctgtacc tgcagctgct    540
gcagctgctg cacagaaatt aatgagaagt agaaatcgtg gcccacctcc ctcttggggt    600
cgtcgccctc gagatgatta tcgtaggagg agtcctccac ctcgtcgcag atctccaaga    660
aggagaagct tctctcgcag ccggagcagg tccctttcta gagataggag aagagagaga    720
tcgctgtctc gggagagaaa tcacaagccg tcccgatcct tctctaggtc tcgtagtcga    780
tctaggtcaa atgaaaggaa atga                                           804
```

```
<210> SEQ ID NO 87
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 87

Ile Gln Lys Gly Asn Phe Arg Asn Gln Arg Lys Thr Val Lys Cys Phe
1               5                   10                  15

Asn Cys Gly Lys Glu Gly His Ile Ala Lys Asn Cys Arg Ala Pro Arg
            20                  25                  30

Lys Lys Gly
        35

<210> SEQ ID NO 88
<211> LENGTH: 100
<212> TYPE: PRT
<213> ORGANISM: Artificial Sequence
<220> FEATURE:
<223> OTHER INFORMATION: Synthetic Polypeptide

<400> SEQUENCE: 88

Asn Thr Glu Asn Lys Ser Gln Pro Lys Arg Leu His Val Ser Asn Ile
1               5                   10                  15

Pro Phe Arg Phe Arg Asp Pro Asp Leu Arg Gln Met Phe Gly Gln Phe
            20                  25                  30

Gly Lys Ile Leu Asp Val Glu Ile Ile Phe Asn Glu Arg Gly Ser Lys
        35                  40                  45

Gly Phe Gly Phe Val Thr Phe Glu Asn Ser Ala Asp Ala Asp Arg Ala
    50                  55                  60

Arg Glu Lys Leu His Gly Thr Val Val Glu Gly Arg Lys Ile Glu Val
65                  70                  75                  80

Asn Asn Ala Thr Ala Arg Val Met Thr Asn Lys Lys Thr Val Asn Pro
                85                  90                  95

Tyr Thr Asn Gly
            100

<210> SEQ ID NO 89
<211> LENGTH: 79
<212> TYPE: PRT
<213> ORGANISM: Artificial Sequence
<220> FEATURE:
<223> OTHER INFORMATION: Synthetic Polypeptide

<400> SEQUENCE: 89

Arg Ser Arg Asn Arg Gly Pro Pro Pro Ser Trp Gly Arg Arg Pro Arg
1               5                   10                  15
```

```
Asp Asp Tyr Arg Arg Ser Pro Pro Pro Arg Arg Ser Pro Arg
            20                  25                  30

Arg Arg Ser Phe Ser Arg Ser Arg Ser Arg Ser Leu Ser Arg Asp Arg
        35                  40                  45

Arg Arg Glu Arg Ser Leu Ser Arg Glu Arg Asn His Lys Pro Ser Arg
    50                  55                  60

Ser Phe Ser Arg Ser Arg Ser Arg Ser Asn Glu Arg Lys
65                  70                  75
```

<210> SEQ ID NO 90
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 90

```
Met Glu Tyr Pro Tyr Asp Val Pro Asp Tyr Ala Met Ala Val Ser Val
1               5                   10                  15

Thr Pro Ile Arg Asp Thr Lys Trp Leu Thr Leu Glu Val Cys Arg Glu
            20                  25                  30

Phe Gln Arg Gly Thr Cys Ser Arg Pro Asp Thr Glu Cys Lys Phe Ala
        35                  40                  45

His Pro Ser Lys Ser Cys Gln Val Glu Asn Gly Arg Val Ile Ala Cys
    50                  55                  60

Phe Asp Ser Leu Lys Gly Arg Cys Ser Arg Glu Asn Cys Lys Tyr Leu
65                  70                  75                  80

His Pro Pro Pro His Leu Lys Thr Gln Leu Glu Ile Asn Gly Arg Asn
                85                  90                  95

Asn Leu Ile Gln Gln Lys Asn Met Ala Met Leu Ala Gln Gln Met Gln
            100                 105                 110

Leu Ala Asn Ala Met Met Pro Gly Ala Pro Leu Gln Pro Val Pro Met
        115                 120                 125

Phe Ser Val Ala Pro Ser Leu Ala Thr Asn Ala Ser Ala Ala Ala Phe
    130                 135                 140

Asn Pro Tyr Leu Gly Pro Val Ser Pro Ser Leu Val Pro Ala Glu Ile
145                 150                 155                 160

Leu Pro Thr Ala Pro Met Leu Val Thr Gly Asn Pro Gly Val Pro Val
                165                 170                 175

Pro Ala Ala Ala Ala Ala Ala Gln Lys Leu Met Ile Gln Lys Gly
            180                 185                 190

Asn Phe Arg Asn Gln Arg Lys Thr Val Lys Cys Phe Asn Cys Gly Lys
        195                 200                 205

Glu Gly His Ile Ala Lys Asn Cys Arg Ala Pro Arg Lys Lys Gly Tyr
    210                 215                 220

Gly Arg Lys Lys Arg Gln Arg Arg Arg
225                 230
```

<210> SEQ ID NO 91
<211> LENGTH: 296
<212> TYPE: PRT
<213> ORGANISM: Artificial Sequence
<220> FEATURE:
<223> OTHER INFORMATION: Synthetic Polypeptide

<400> SEQUENCE: 91

```
Met Glu Tyr Pro Tyr Asp Val Pro Asp Tyr Ala Met Ala Val Ser Val
1               5                   10                  15
```

```
Thr Pro Ile Arg Asp Thr Lys Trp Leu Thr Leu Glu Val Cys Arg Glu
            20                  25                  30

Phe Gln Arg Gly Thr Cys Ser Arg Pro Asp Thr Glu Cys Lys Phe Ala
        35                  40                  45

His Pro Ser Lys Ser Cys Gln Val Glu Asn Gly Arg Val Ile Ala Cys
    50                  55                  60

Phe Asp Ser Leu Lys Gly Arg Cys Ser Arg Glu Asn Cys Lys Tyr Leu
65                  70                  75                  80

His Pro Pro Pro His Leu Lys Thr Gln Leu Glu Ile Asn Gly Arg Asn
                85                  90                  95

Asn Leu Ile Gln Gln Lys Asn Met Ala Met Leu Ala Gln Gln Met Gln
            100                 105                 110

Leu Ala Asn Ala Met Met Pro Gly Ala Pro Leu Gln Pro Val Pro Met
        115                 120                 125

Phe Ser Val Ala Pro Ser Leu Ala Thr Asn Ala Ser Ala Ala Ala Phe
    130                 135                 140

Asn Pro Tyr Leu Gly Pro Val Ser Pro Ser Leu Val Pro Ala Glu Ile
145                 150                 155                 160

Leu Pro Thr Ala Pro Met Leu Val Thr Gly Asn Pro Gly Val Pro Val
                165                 170                 175

Pro Ala Ala Ala Ala Ala Ala Gln Lys Leu Met Asn Thr Glu Asn
            180                 185                 190

Lys Ser Gln Pro Lys Arg Leu His Val Ser Asn Ile Pro Phe Arg Phe
        195                 200                 205

Arg Asp Pro Asp Leu Arg Gln Met Phe Gly Gln Phe Gly Lys Ile Leu
    210                 215                 220

Asp Val Glu Ile Ile Phe Asn Glu Arg Gly Ser Lys Gly Phe Gly Phe
225                 230                 235                 240

Val Thr Phe Glu Asn Ser Ala Asp Ala Asp Arg Ala Arg Glu Lys Leu
                245                 250                 255

His Gly Thr Val Val Glu Gly Arg Lys Ile Glu Val Asn Asn Ala Thr
            260                 265                 270

Ala Arg Val Met Thr Asn Lys Lys Thr Val Asn Pro Tyr Thr Asn Gly
        275                 280                 285

Pro Lys Lys Lys Arg Lys Val Glu
    290                 295

<210> SEQ ID NO 92
<211> LENGTH: 267
<212> TYPE: PRT
<213> ORGANISM: Artificial Sequence
<220> FEATURE:
<223> OTHER INFORMATION: Synthetic Polypeptide

<400> SEQUENCE: 92

Met Glu Tyr Pro Tyr Asp Val Pro Asp Tyr Ala Met Ala Val Ser Val
1               5                   10                  15

Thr Pro Ile Arg Asp Thr Lys Trp Leu Thr Leu Glu Val Cys Arg Glu
            20                  25                  30

Phe Gln Arg Gly Thr Cys Ser Arg Pro Asp Thr Glu Cys Lys Phe Ala
        35                  40                  45

His Pro Ser Lys Ser Cys Gln Val Glu Asn Gly Arg Val Ile Ala Cys
    50                  55                  60

Phe Asp Ser Leu Lys Gly Arg Cys Ser Arg Glu Asn Cys Lys Tyr Leu
65                  70                  75                  80
```

```
His Pro Pro Pro His Leu Lys Thr Gln Leu Glu Ile Asn Gly Arg Asn
                85                  90                  95

Asn Leu Ile Gln Gln Lys Asn Met Ala Met Leu Ala Gln Gln Met Gln
            100                 105                 110

Leu Ala Asn Ala Met Met Pro Gly Ala Pro Leu Gln Pro Val Pro Met
            115             120                 125

Phe Ser Val Ala Pro Ser Leu Ala Thr Asn Ala Ser Ala Ala Ala Phe
            130             135                 140

Asn Pro Tyr Leu Gly Pro Val Ser Pro Ser Leu Val Pro Ala Glu Ile
145                 150             155                     160

Leu Pro Thr Ala Pro Met Leu Val Thr Gly Asn Pro Gly Val Pro Val
                165             170                 175

Pro Ala Ala Ala Ala Ala Ala Gln Lys Leu Met Arg Ser Arg Asn
            180             185                 190

Arg Gly Pro Pro Pro Ser Trp Gly Arg Arg Pro Arg Asp Asp Tyr Arg
        195             200                 205

Arg Arg Ser Pro Pro Pro Arg Arg Arg Ser Pro Arg Arg Arg Ser Phe
        210             215             220

Ser Arg Ser Arg Ser Arg Ser Leu Ser Arg Asp Arg Arg Arg Glu Arg
225                 230                 235                 240

Ser Leu Ser Arg Glu Arg Asn His Lys Pro Ser Arg Ser Phe Ser Arg
                245             250                 255

Ser Arg Ser Arg Ser Arg Ser Asn Glu Arg Lys
                260             265
```